(12) United States Patent
Webb et al.

(10) Patent No.: US 8,703,913 B2
(45) Date of Patent: Apr. 22, 2014

(54) SENSOR

(75) Inventors: Martin Webb, London (GB); Simone Kunzelmann, London (GB)

(73) Assignee: Medical Research Council (GB)

( * ) Notice: Subject to any disclaimer, the term of this patent is extended or adjusted under 35 U.S.C. 154(b) by 0 days.

(21) Appl. No.: 13/119,112

(22) PCT Filed: Sep. 15, 2009

(86) PCT No.: PCT/GB2009/002208
§ 371 (c)(1),
(2), (4) Date: Jun. 23, 2011

(87) PCT Pub. No.: WO2010/032001
PCT Pub. Date: Mar. 25, 2010

(65) Prior Publication Data
US 2011/0294137 A1 Dec. 1, 2011

(30) Foreign Application Priority Data
Sep. 19, 2008 (GB) .................................. 0817166.2

(51) Int. Cl.
| | | |
|---|---|---|
| *A61K 38/00* | (2006.01) | |
| *C07K 2/00* | (2006.01) | |
| *C07K 4/00* | (2006.01) | |
| *C07K 5/00* | (2006.01) | |
| *C07K 7/00* | (2006.01) | |
| *C07K 14/00* | (2006.01) | |
| *C07K 16/00* | (2006.01) | |
| *C07K 17/00* | (2006.01) | |

(52) U.S. Cl.
USPC .............................. 530/350; 435/7.6; 435/7.9

(58) Field of Classification Search
None
See application file for complete search history.

(56) References Cited

U.S. PATENT DOCUMENTS 6,610,836 B1   8/2003   Breton

FOREIGN PATENT DOCUMENTS

| WO | 00/68418 A1 | 11/2000 | | |
|---|---|---|---|---|
| WO | 03/014731 A2 | 2/2003 | | |
| WO | 2004/027421 A2 | 4/2004 | | |
| WO | WO2004027421 A1 * | 4/2004 | ............ | C07K 16/44 |
| WO | 2007/026155 B1 | 3/2007 | | |

OTHER PUBLICATIONS

Martin R. Webb, Development of fluorescent biosensors for probing the function of motor proteins, Mol. BioSyst, 2007, 3, 249-256.*
Roeben et al. "Crystal structure of an archaeal actin homolog" J. Mol. Biol. 358(1): 145-156 (Apr. 21, 2006).
Harald Schmidt "Written Opinion of the International Searching Authority" Dec. 1, 2009.

* cited by examiner

*Primary Examiner* — Maury Audet
*Assistant Examiner* — Joseph Fischer
(74) *Attorney, Agent, or Firm* — Thomas G. Peterson; Nicholas J. Landau; Bradley Arant Boult Cummings LLP

(57) ABSTRACT

The invention relates to an ADP binding molecule comprising a polypeptide, said polypeptide comprising amino acid sequence corresponding to at least amino acids 11 to 310 of SEQ ID NO:1, wherein said polypeptide comprises a substitution relative to SEQ ID NO:1 at amino acid C287, and wherein said polypeptide comprises a further cysteine residue for attachment of at least one reporter moiety, and wherein said polypeptide has at least 68% sequence identity to SEQ ID NO:1 at the amino acid residues corresponding to those shown in column III of table A.

15 Claims, 15 Drawing Sheets ures. One advantage of this
SENSOR

FIELD OF THE INVENTION

The invention is in the field of adenosine diphosphate (ADP) monitoring. In particular the invention relates to ADP binding molecules comprising polypeptides from the bacterial ParM protein and one or more fluorophores.

BACKGROUND TO THE INVENTION

Adenosine triphosphate (ATP) conversion to ADP is a central process in all living organisms and is catalyzed by a vast number of different enzymes. The energy generated by ATP hydrolysis can drive metabolic processes, directed transport, force-generation and movement as well as signal transduction and regulation. Kinases transfer the terminal phosphate of ATP yielding ADP as a product and phosphorylate a wide variety of substrates, from metabolic intermediates to proteins, so controlling their activity. Hence, assays to monitor ADP concentrations have wide applications in biochemical and biomedical research, ranging from detailed understanding of mechanochemical coupling in motor proteins to screening for ATPase and kinase inhibitors.

Despite the importance of ADP detection in biological systems only few methods for monitoring ADP concentrations are available to date. Most widely applied is a coupled enzyme assay using pyruvate kinase and lactate dehydrogenase, which couples ADP generation to the oxidation of NADH and a concomitant absorbance or fluorescence decrease. Although frequently used to study steady-state kinetics of ATPases and kinases, this approach is generally not suitable for mechanistic studies based on transient kinetics, since it lacks fast response and high sensitivity, which are drawbacks of this system. The fact that several components must be present for the assay is also problematic, and adds complexity and cost, especially for high throughput applications. Some compounds may interfere with one of the assay components and/or with UV detection. With a large number of components, the risks of such interference problems are correspondingly large.

Recently, the assay has been modified to generate a fluorescence by coupling the pyruvate kinase reaction with pyruvate oxidase and horseradish peroxidase (1). Amplex Red is converted to Resorufin by peroxidase, yielding a fluorescence increase at 590 nm. The fluorescence detection at high wavelength provides improvements, both in enhanced sensitivity as well as in separating the optical signal from the absorbance of many compounds. However, this assay does not circumvent the problem of interference with one of the several assay components. Moreover, the assay is still an enzyme-coupled assay which imposes requirements on the system to be permissive of the differing enzyme activities required, and involves numerous interdependent components to the assay, which remain problems even with this improved version.

Aimed at the development of high throughput assays for kinases, two ADP-specific sensors have been reported, which are based on ADP recognition by RNA molecules (2). The first relies on an RNA aptamer which selectively binds ADP and can be used to monitor ADP generation in a (radiometric) scintillation proximity assay. Although this method can be used for real time measurements, it is again a complex multi-component system and involves radiometric scintillation, which is hazardous and costly. The second sensor creates a fluorescence readout based on ADP dependent self-cleavage of a fluorescently labeled ribozyme. This method cannot be used for real time measurements, which is a hindrance.

An alternative approach is to take advantage of the highly specific interaction of a binding protein with the target molecule. By attaching a fluorophore in a suitable position on the protein, ligand recognition can be coupled to an optical signal. Such fluorescent protein-based biosensors have been reported for a number of biomolecules such as sugars, amino acids, metal ions and phosphate (3-7). One advantage of this type of sensor is that the signal change can be very fast, only limited by the speed of ligand binding or the associated conformational change. Furthermore, only a single component, the labeled protein, is needed for detection, so they are also classified as reagentless biosensors. Such a biosensor for ADP has been developed previously, based on a nucleoside diphosphate kinase labeled with the coumarin dye IDCC (8). The biosensor responds to the ADP/ATP concentration ratio and thus can detect a wide range of ADP concentrations, from sub-micromolar to millimolar. However, the fluorescence decreases with ADP and this is unfavourable. Moreover, decreasing fluorescence with ADP binding causes the sensitivity to be low, particularly when measuring initial rates, which is a problem. In addition, the fluorescence intensity is not linearly dependent on the ADP concentration, which is a drawback of this system.

The present invention seeks to overcome problem(s) associated with the prior art.

SUMMARY OF THE INVENTION

Phosphate sensor proteins are known in the art. Typically, the focus in the prior art has been binding of inorganic phosphate (Pi). To this end, sensor proteins from the prior art have been based on phosphate binding proteins.

The present inventors have taken a markedly different approach. They have surprisingly taken a protein from the field of bacterial plasmid partitioning, and have engineered this for use as an ADP sensor. This has been very technically demanding, since the protein upon which the ADP sensing molecules of the invention is based (ParM) has an intrinsic ATPase activity, and is known to bind guanine nucleotide as well as ADP. Notwithstanding the apparent unsuitability on this protein for use as an ADP sensing molecule, the inventors have successfully created a robust reagentless sensor for ADP.

The invention provides numerous technical benefits. These include the avoidance of nucleic acid based sensors such as ribozymes. Furthermore, by focusing on ADP rather than inorganic phosphate (Pi), a more biologically relevant molecule is being assayed. Moreover, by monitoring ADP rather than Pi, the molecules of the invention find application in a range of assays which do not in fact generate Pi. An important example is the application to the monitoring of kinase assays, in which phosphate is of course incorporated into the target substrate rather than being released as Pi. These and other advantages of the invention are discussed in more detail below.

In one aspect the invention relates to an ADP binding molecule comprising a polypeptide, said polypeptide comprising amino acid sequence corresponding to at least amino acids 11 to 310 of SEQ ID NO:1, wherein said polypeptide comprises a substitution relative to SEQ ID NO:1 at amino acid C287, and wherein said polypeptide comprises a further cysteine residue for attachment of at least one reporter moiety, and wherein said polypeptide has at least 68% sequence identity to SEQ ID NO:1 at the amino acid residues corresponding to those shown in column III of table A. Suitably said polypeptide may comprise one or more substitutions relative to SEQ ID NO:1 at one or more amino acid residues selected from D6, G8, S9, T10, K13, N69, T101, E148, D170, G172, G173, T174, T175, D177, D223, I227, E284, or Q308.

In another aspect, the invention relates to an ADP binding molecule as described above wherein said polypeptide comprises a substitution or substitutions selected from:
(i) I27C; or
(ii) D63C and K216C; or
(iii) D63C and D224C.

In another aspect the invention provides an ADP binding molecule comprising a polypeptide, said polypeptide comprising amino acid sequence corresponding to at least amino acids 11 to 310 of SEQ ID NO:1, wherein said polypeptide comprises a substitution relative to SEQ ID NO:1 at amino acid C287, and wherein said polypeptide comprises a further substitution or substitutions selected from:
(i) I27C; or
(ii) D63C and K216C; or
(iii) D63C and D224C.

Thus the invention provides a sensor molecule which has the advantage of attachment sites for one or more fluorophores at a position which enables positive increase in fluorescence upon ADP binding. This is in contrast to attachment of fluorophores at the wild-type C287 residue, which results in a decrease of fluorescence on ADP binding.

A further advantage is that by attachment of fluorophore at one or more of the substituted sites mentioned (I27C, D63C, K216C or D224C), efficient function of the fluorophore is achieved, including enablement of rhodamine stacking when more than one rhodamine type fluorophore is used.

In another aspect, the invention relates to an ADP binding molecule as described above, wherein said polypeptide comprises a further substitution or substitutions selected from:
(iv) T175N; or
(v) T174A and T175A; or
(vi) T174A and T175N; or
(vii) T175L.
These substitutions provide the advantage of increased ADP selectivity.

In another aspect, the invention relates to an ADP binding molecule as described above, wherein said polypeptide comprises a further substitution or substitutions selected from:
(iv) T175N; or
(v) T174A and T175A; or
(vi) T174A and T175N.
In addition to the advantage of increased ADP selectivity, these specific substitutions provide the further advantage of increasing the $K_d$ for ADP.

Suitably said molecule further comprises at least one fluorophore attached thereto.

Thus, in another aspect, the invention relates to an ADP binding molecule as described above further comprising at least one flurophore attached thereto, wherein said fluorophore is attached at a position on the polypeptide such that conformational change of the polypeptide upon ADP binding causes a corresponding change in fluorescence of said fluorophore. Suitably the or each fluorophore is attached to the polypeptide via an amino acid residue corresponding to one or more of I27C, D63C, K216C or D224C.

Suitably the or each fluorophore is attached to said polypeptide at an amino acid residue selected from:
(i) I27C; or
(ii) D63C and K216C; or
(iii) D63C and D224C.

Suitably said molecule comprises at least one N-[2-(1-maleimidyl)ethyl]-7-diethylaminocoumarin-3-carboxamide (MDCC) moiety attached thereto.

Suitably said molecule comprises at least two 6-iodoacetamidotetramethylrhodamine (6-IATR) moieties attached thereto.

Suitably said molecule comprises at least two 5-iodoacetamidotetramethylrhodamine (5-IATR) moieties attached thereto.

In another aspect, the invention relates to an ADP binding molecule as described above, said molecule comprising the amino acid sequence of SEQ ID NO:2 or SEQ ID NO:5. (Sometimes referred to as MDCC-ParM).

In another aspect, the invention relates to an ADP binding molecule as described above, said molecule comprising the amino acid sequence of SEQ ID NO:3 or SEQ ID NO:4 or SEQ ID NO:6 or SEQ ID NO:7. (Sometimes referred to as 5-ATR-ParM or 6-ATR-ParM).

In another aspect, the invention relates to a nucleic acid having a nucleotide sequence encoding the polypeptide portion of an ADP binding molecule as described above.

In another aspect, the invention relates to a method for monitoring changes in ADP concentration in a sample comprising contacting said sample with an ADP binding molecule according to any preceding claim and determining changes in conformation of said ADP binding molecule, wherein changes in conformation of said ADP binding molecule indicate changes in the concentration of ADP in said sample.

The methods of the invention can be performed in vitro or in vivo. Suitably assays are in vitro assays.

The sample may be from any source, including serum, urine, saliva, sweat, tissue culture, cell extracts, cell lines, food, beverages, pharmaceuticals and environmental (e.g. water). Suitably the sample comprises in vitro assay(s) for candidate ATPases or kinases, or assay(s) for the effect of candidate compounds on known ATPases or kinases.

Suitably the conformation of said ADP binding molecule is monitored by measurement of changes in fluorescence of a fluorophore comprised by said ADP binding molecule.

Suitably the sample comprises an ATPase. This enables the ATPase activity to be directly measured via the ADP binding molecule. Suitably this is conducted in real time, allowing the reaction status to be dynamically monitored.

Suitably the sample comprises a helicase or a kinase, most suitably a kinase. In particular, it is advantageous to monitor kinase reactions in accordance with the present invention since kinases are important drug targets and the opportunity to monitor their activity in real time and independent of the identity of the kinase and/or substrate is a beneficial feature of the invention.

DETAILED DESCRIPTION OF THE INVENTION

The inventors disclose the development of an ADP-specific sensor using the prokaryotic actin homologue, ParM, as the binding protein. ParM is encoded on the *Escherichia coli* plasmid R1 and is required for segregation of this low-copy number plasmid (9). The partition locus of R1 contains three elements, the genes encoding ParM and ParR and the centromere-like DNA region ParC, which together constitute the complete machinery necessary for plasmid partitioning (10-12). The DNA binding protein ParR specifically recognizes the ParC region of R1 and the formation of the ParR/ParC complex mediates plasmid pairing (13). Plasmid segregation is driven by the ParM ATPase forming actin-like filaments (14, 15), which are stabilized by the interaction with ParR/ParC (16-18). The exact mechanism of how ParM polymerisation drives plasmid transport is subject of many investigations (18-23).

The selection of ParM for use in the ADP binding molecule of the invention provides a number of advantages. First, due to its prokaryotic origin and relatively small size it can be strongly overexpressed in E. coli and therefore is straightforward to manufacture in large quantities. Second, there are crystal structures available, evidencing that ParM undergoes a large conformation change upon ADP binding (15). Following from these structures, the inventors were able to rationally design labeling positions, where fluorophores are likely to respond to ADP binding, and then through experimental insights select those which provided the desired function. Thirdly, ParM has a high affinity for ADP: a dissociation constant of 2.4 µM has been reported for the fluorescent analogue ethenoADP (19). A high affinity is advantageous for ADP detection with high sensitivity.

The invention provides a reagentless biosensor for ADP based on a fluorescently labeled variant of the bacterial actin homologue, ParM. A preferred embodiment of the sensor, MDCC-ParM (His$_6$/I27C/T174A/T175N/C287A), contains a single coumarin label attached to Cys27. The labeled protein binds ADP tightly ($K_d$=0.6 µM) and fast ($k_{on}$=0.6 µM$^{-1}$ s$^{-1}$), associated with a fourfold increase in fluorescence intensity. The biosensor shows strong discrimination against ATP: the interaction with ATP is more than 300-fold weaker than the interaction with ADP. As we have demonstrated in steady-state assays on a DNA helicase and a protein kinase, the sensors are suitable for real-time monitoring of ADP generation in ATPase and kinase reactions.

As described, in this embodiment the MDCC is positioned on the b-sheet of one subdomain and brought into close proximity to a second subdomain upon ADP-triggered cleft closure (15). The large fluorescence change is likely to originate from the interaction of the fluorophore with the second domain, thus reporting the conformational change. However, since the label is in the vicinity of the bound nucleotide base (~10 Å shortest distance), a direct interaction of the MDCC with ADP might possibly also contribute to the observed signal change. Such an induced-fit mechanism is common to many ligand binding proteins and can often be detected in kinetic measurements of ligand association. The rate of the conformational change has important implications for the performance of the MDCC-ParM sensor as it defines how fast the sensor can respond and thus how suitable it is for transient kinetic experiments. The association kinetics of MDCC-ParM and ADP show a linear dependence of the observed rate constant on ADP concentrations up to 200 µM. At higher ADP concentrations than reported, there is some indication that values of $k_{obs}$ are approaching a limit. This may be due to a conformational change becoming rate limiting and most likely this would represent the cleft closure. However, at 20° C. rates were too fast to characterize the two step binding mechanism fully.

As outlined above, a major challenge in the development of an ADP sensor is to achieve discrimination against ATP. Wild-type ParM binds the triphosphate analogue ethenoATP 60-fold tighter than the diphosphate ethenoADP with dissociation constants of 0.04 and 2.4 µM, respectively (19). The MDCC-labeled ParM (I27C/C287A) had 60-fold binding preference for ADP over ATP. This is in part due to an increased ADP affinity ($K_d$=0.31 µM), but mainly due to a strongly (470-fold) weakened ATP binding ($K_d$=18.7 µM). The large difference might be caused by the two point mutations or by the MDCC attached to Cys27. The two mutated residues do not contact the bound nucleotide and the MDCC, although close to the base, is far from the phosphates, so a direct effect on the nucleotide interactions seems unlikely. Instead the modifications may change ParM conformation and so indirectly affect nucleotide affinities. As mentioned above, the MDCC may interact with the opposite subdomain, when ADP is bound, which could stabilise the closed (ADP-bound) conformation. Orlova et al. (14) suggested a more open conformation of ParM in ATP-bound filaments, deduced from 3D reconstructions of cryo-EM images of AMPPNP-bound ParM filaments. Thus, stabilization of a closed conformation of ParM by MDCC might reduce ATP affinity. Alternatively, the difference in nucleotide affinities may be directly due to the etheno-analogues used by Garner et al. (19). The nucleotide complex structures of ParM show an interaction of Glu284 with the N1 of the purine base, which is modified in the etheno-analogues and thus could influence the affinity. However, without wishing to be bound by theory, the modification is far away from the phosphates and thus it is difficult to explain a differential affect on diphosphate and triphosphate binding.

A preferred sensor MDCC-ParM (His$_6$/I27C/T174A/T175N/C287A) contains two additional active site mutations, T174A and T175N, which further reduced ATP binding affinity. The resultant molecule binds ATP more than 300-fold weaker than ADP with a dissociation constant of ~200 µM. The fluorescence change upon ATP binding is similar to ADP-binding.

Associated with ATP binding are two other potential problems of filament formation and ATP hydrolysis. ParM is able to form an actin-like filament, which is required for its function in plasmid segregation (14-16, 18). Filament formation may influence the fluorescence signal and/or nucleotide affinity. The critical concentration in presence of ADP is high, ~100 µM (19) and will not be reached under normal assay conditions. In contrast, ParM filaments are easily formed in presence of ATP with a critical concentration of 2.3 µM (19). In our experiments, we have not observed any effects of filament formation, e.g. titrations are well described by simple (non-cooperative) binding models and calibration curves show linear dependence on the ADP concentration also in the presence of ATP. Thus, this potential theoretical problem does not adversely affect working of the invention.

Nevertheless, for certain applications it may be advantageous to eliminate filament formation, for example at high sensor concentration, high ATP concentration or other conditions which might otherwise promote filament formation. For this reason the inventors used an optional K33A mutation to suppress filament formation. In particular, MDCC-ParM (His$_6$/I27C/T174A/T175N/C287A) was analysed for filament formation and indeed was shown to be able to polymerise, albeit slowly and at high ATP concentrations. The additional optional mutation introduced to address this is suitably a K33 substitution; most suitably K33A. The K33A substitution completely abolished filament formation (see examples section).

Filament formation was analysed for 5-ATR- and 6-ATR-ParM (His$_6$/D63C/T174A/T175N/D224C/C287A). Both were shown to be able to form filaments. However, since the rhodamine-ParM sensors are often most suitably used below the critical concentration for filament formation, again it is not essential to introduce any mutation(s) to ameliorate this. Nevertheless, it may be advantageous to introduce an additional mutation to address this; said mutation is suitably a K33 substitution; most suitably K33A. The K33A substitution completely abolished filament formation (see examples section).

Thus suitably the sensor polypeptide of the invention comprises a K33 substitution, most suitably a K33A substitution, which has the advantage of reducing or eliminating filament formation.

A second potential problem is ParM-catalyzed ATP hydrolysis. The intrinsic ATPase activity of ParM is low, but is strongly accelerated by polymerization to ~3 min$^{-1}$ at 37° C. (16). We have not directly measured the hydrolysis activity of MDCC-ParM at this stage, but an upper limit can be estimated from control experiments of the helicase and kinase assays, where only MDCC-ParM and ATP were present. The hydrolysis rate is low, 0.004 min$^{-1}$ at 5 µM ATP, 20° C. Therefore, in practice MDCC-ParM polymerisation and ATP hydrolysis do not seem to cause any serious problem in working the invention.

In contrast to eukaryotic actin, which specifically binds adenine nucleotides, its prokaryotic and archeabacterial homologues, MreB, FtsA and Ta00583, show a rather low specificity for the base (37-41). ParM binds guanine nucleotides in addition to adenine nucleotides and since GTP induces more rapid filament formation than ATP it has been proposed to be the physiological substrate of ParM (21). However, the affinities for GDP and GTP have not been determined. The fluorescence of MDCC-ParM slightly decreases (by ~30%) upon addition of GDP (1 mM), as opposed to a four-fold fluorescence increase when ADP binds. This result was surprising, since the ParM conformations observed in the ADP and GDP-bound structures are virtually identical and thus can not explain the observed difference in fluorescence response. It is also possible that GDP does not bind to the MDCC-ParM variant under the experimental conditions used. This may be further examined in competition experiments with ADP, to determine if guanine nucleotides might inhibit the biosensor response with ADP.

There are a number of advantages of MDCC-ParM for use in time-resolved ADP assays. MDCC-ParM is used in stoichiometric amounts, detecting every molecule of ADP generated, and is therefore likely to be useful for detection of submicromolar to ~10 µM ADP. The range of ATP concentrations to be used in the assays is <200 µM, mainly due to the loss of sensitivity: At 200 µM ATP half of the MDCC-ParM molecules are nucleotide bound and thus the fluorescence level is already half of the maximal change obtainable. However, for this type of sensitive assay, ADP contamination may become significant, whatever assay method. Commercial ATP contains 0.1-1% ADP, so that 100 µM ATP may already contain 1 µM ADP. Careful purification can take this to <0.1% for non-routine use. The maximum measurable rates are a compromise between sensitivity and protein use. At very high biosensor concentration, ADP binds at >100 s$^{-1}$. However, for routine use, the assay is most suitable for rate constants <10 s$^{-1}$.

The MDCC-ParM sensor provides several advantages in comparison to the current ADP assays described in the Introduction. As a reagentless sensor it is a one component system where only the labelled protein (apart from Mg$^{2+}$ as a cofactor) is required for the assay. Normally Mg$^{2+}$ would also be required for the reaction being studied. The sensitivity is submicromolar and the fluorescence increase means that it can measure initial reaction rates readily. Suitably assays of the invention comprise Mg$^{2+}$.

In addition to the coumarin-labeled ParM sensor described, other embodiments include two ParM mutants which were doubly labeled with the rhodamine probes S— and 6-IATR, exploiting the rhodamine stacking interaction as the basis for a fluorescence change. The largest signal change was obtained with 6-ATR-ParM (D63C/D224C), which responds to ADP binding with a 10-fold fluorescence increase. However, the ADP affinity is strongly reduced ($K_d$=140 µM).

This reduced affinity could be due to the larger size of the rhodamines, along with the two cysteine mutations affecting the binding. Alternatively the binding of ADP requires the cleft closure and hence the disruption of the rhodamine stacking interaction. A second rhodamine labeled double mutant (D63C/K216C) has only twofold reduced ADP affinity suggesting that weakened ADP binding is at least in part due to the mutation D224C. Also, in a previous use of rhodamine stacking sensing a protein conformation change with the phosphate binding protein, the rhodamine had little affect on the affinity for inorganic phosphate (30). The low affinity makes the rhodamine version less sensitive in comparison to the MDCC sensor, but more suitable for high ATP concentrations.

The rhodamine-labeled biosensor may advantageously be used in a different manner than MDCC-ParM, that is at lower concentration than the ADP to be detected. Because of the weak binding, the degree of saturation and thus the fluorescence will vary with ADP in the range of the dissociation constant. While this results in loss of sensitivity, it may extend the potential use to higher ATP concentrations and mean that ADP contamination in ATP is less problematic than with MDCC-ParM. In addition, rhodamine is generally more photostable than coumarin. These properties are likely to make 6-ATR-ParM more suitable for applications like high throughput assays.

ParM

The ParM structure has been solved in four different states, the nucleotide-free form as well as the complexes with ADP, GDP and GMPPNP (15, 21). ParM consists of two domains (I and II), which are both further divided into subdomains A and B. The nucleotide binding site is located in a cleft between the domains with residues from both domains contributing to the interaction. In the absence of nucleotide, ParM is in an open conformation. The structure of the ADP complex shows a large (25°) rigid body movement of the two domains relative to each other, leading to cleft closure (15). The ParM conformation in the GDP and GMPPNP complexes is virtually identical to the ADP structure with no striking difference between the domain orientation of ParM bound to the triphosphate analogue or the diphosphates (21).

Although the choice of ParM for use in a reagentless biosensor provides several advantageous properties as outlined above, the choice also presented several problems that are potentially disadvantageous or deleterious. One problem in the development of a specific ADP assay system is that the assays are likely to be performed in the presence of ATP as substrate, which may bind or at least inhibit assay components. In the case of a biosensor based on binding, there must be discrimination against ATP. ParM binds the triphosphate analogue ethenoATP ~60-fold tighter ($K_d$=40 nM) than ethenoADP (19). ParM has the potential for filament formation, which may affect the fluorescence signal and/or nucleotide binding. Finally, ParM has ATPase activity. Since biosensor is likely to be present in the assay solution at relatively high concentration, this ATPase activity may interfere. The inventors disclose how these problems are addressed by manipulation of the protein, particularly by mutation (such as substitution) of certain amino acids.

ParM Polypeptides

The polypeptide components of the molecules of the invention are based on ParM. In particular, amino acid addresses given in the application correspond to the numbering of the ParM reference sequence of SEQ ID NO:1. Where truncated or extended forms of ParM are used as polypeptides in molecules of the invention (e.g. where a 6his tag is added or where a section of the polypeptide is deleted) then the amino acid numbering should be treated as corresponding to the equivalent section of the full length ParM reference sequence and not as an 'absolute' or rigidly inflexible numeric address. By way of explanation, if the description mentions a substitution of C287, this means amino acid 287 of the ParM reference sequence of SEQ ID NO: 1. If the polypeptide used is truncated by deletion of the first 10 amino acids, the address given will still be C287 (rather than e.g. C277)—this will be easily understood by the skilled reader to refer to the amino acid of the corresponding context with reference to the full length ParM sequence of SEQ ID NO:1, as is conventional in the art.

Clearly there are elements of the ParM wild type sequence which we teach are important to mutate, such as by substitution, to achieve certain advantages. However, there are also numerous residues which may or may not be mutated depending on operator choice. Clearly there are also numerous residues which should not be mutated in case such mutation would interfere with the function of the polypeptide. Typically it would be expected that if the skilled operator had a concern whether or not a particular residue could be mutated or not, they could make the mutation and then test the resulting polypeptide to ensure that the desired property was retained in the mutated version. However, in order to provide further guidance on this point, the following comments are made:

The ParM polypeptide has been studied in detail and each residue has been classified as set out in Table A below. The classification is as follows:

Buried: ParM residues in the core of the structure where mutations are likely to affect the function of the sensor.
Exposed: ParM residues on the surface of the protein. Mutations of these residues are likely to retain the sensor function.
Intermediate: Change in sensor function when mutating these residues is possible, but may be difficult to predict e.g. routine testing of resulting mutants is particularly preferred when mutating these residues. Most of these are partially buried.

Residues marked with an asterisk (*) designate active site residues which are suitably specifically mutated in order to improve or alter the sensor functions (such as enhanced ADP selectivity, impaired ATP hydrolysis). These are discussed in more detail in the text. These active site amino acids are shown in the table to be intermediate-changeable. In particular, embodiments of the invention involving rhodamine as the reporter moiety of the sensor may comprise further mutation(s) at one or more of these residues.

It is surprising to note the high number of surface amino acids. (Of course, it will be borne in mind that the extent of accessibility does vary.)

TABLE A

| ParM residues | | | | | |
|---|---|---|---|---|---|
| buried (I) | exposed (II) | intermediate (III) | buried (I) | exposed (II) | intermediate (III) |
| Val 3 | Met 1 | Asp 6* | Thr 137 | Asn 111 | Glu 284* |
| Phe 4 | Leu 2 | Gly 8* | Phe 138 | Gln 113 | Cys 287 |
| Ile 5 | Gln 17 | Ser 9* | Ile 140 | Pro 114 | Thr 294 |
| Asp 7 | Glu 18 | Thr 10* | Val 143 | Thr 116 | Ile 296 |
| Asn 11 | Ser 19 | Lys 13* | Val 145 | Glu 117 | Phe 302 |
| Ile 12 | Asp 20 | His 26 | Met 146 | Glu 120 | Thr 304 |
| Leu 14 | Gly 21 | Val 45 | Pro 147 | Arg 121 | Gln 308* |
| Gln 15 | Thr 22 | Asn 47 | Ser 149 | Ala 124 | Asp 310 |
| Trp 16 | Ile 23 | Phe 57 | Ile 150 | Arg 127 | |
| Ser 28 | Lys 24 | Ile 60 | Pro 151 | Lys 129 | |
| Pro 29 | Gln 25 | Pro 62 | Ala 152 | Thr 131 | |
| Asn 30 | Ile 27 | Asn 69* | Gly 153 | Asn 133 | |
| Ser 31 | Lys 33 | Ser 75 | Val 156 | Gly 134 | |
| Phe 32 | Arg 34 | Asp 76 | Leu 157 | Gly 135 | |
| Phe 46 | Glu 35 | Val 77 | Leu 160 | Asp 136 | |
| Tyr 48 | Trp 36 | Leu 87 | Ser 165 | Thr 139 | |

TABLE A-continued

| ParM residues | | | | | |
|---|---|---|---|---|---|
| buried (I) | exposed (II) | intermediate (III) | buried (I) | exposed (II) | intermediate (III) |
| Leu 50 | Ala 37 | Thr 88 | Leu 166 | Lys 141 | |
| Tyr 55 | Val 38 | Thr 101* | Leu 167 | Asp 142 | |
| Ser 56 | Ser 39 | Glu 106 | Ile 168 | Lys 144 | |
| Trp 72 | Phe 40 | Asp 109 | Ile 169 | Glu 155 | |
| Gln 73 | Gly 41 | Asn 112 | Leu 171 | Gln 158 | |
| Tyr 74 | Asp 42 | Asn 115 | Leu 176 | Glu 159 | |
| Asn 78 | Lys 43 | Asn 118 | Ile 178 | Asp 161 | |
| Val 79 | Lys 44 | Lys 123 | Ser 179 | Glu 162 | |
| Val 80 | Thr 49 | Lys 128 | Gln 180 | Leu 163 | |
| Ala 81 | Asn 51 | Glu 148* | Val 181 | Asp 164 | |
| Val 82 | Gly 52 | Tyr 154 | Gly 183 | Lys 184 | |
| His 83 | Glu 53 | Asp 170* | Leu 197 | Leu 185 | |
| His 84 | Gln 54 | Gly 172* | Gly 198 | Ser 186 | |
| Ala 85 | Asp 58 | Gly 173* | Val 199 | Gly 187 | |
| Leu 86 | Pro 59 | Thr 174* | Val 202 | Ser 189 | |
| Ser 89 | Ser 61 | Thr 175* | Thr 203 | Lys 190 | |
| Leu 91 | Asp 63 | Asp 177* | Val 206 | Tyr 192 | |
| Val 96 | Ala 64 | Met 182 | Lys 207 | Gly 193 | |
| Ile 98 | Val 65 | Ile 188 | Leu 210 | Ser 195 | |
| Val 99 | Val 66 | Ile 191 | Ser 219 | Ser 196 | |
| Cys 100 | Thr 67 | Asp 194 | Ala 222 | Ser 204 | |
| Leu 102 | Thr 68 | Ser 200 | Ile 225 | Asp 208 | |
| Pro 103 | Ile 70 | Leu 201 | Ile 226 | Ser 211 | |
| Leu 104 | Ala 71 | Ala 205 | Arg 229 | Leu 212 | |
| Tyr 107 | Gly 90 | Ala 209 | Leu 235 | Ala 213 | |
| Tyr 108 | Pro 92 | Ser 218 | Ile 239 | Arg 214 | |
| Ile 119 | Val 93 | Leu 221 | Ile 245 | Thr 215 | |
| Lys 122 | Ser 94 | Asp 223* | Val 248 | Lys 216 | |
| Asn 125 | Glu 95 | Ile 227* | Met 252 | Gly 217 | |
| Phe 126 | Asp 97 | Ala 251 | Ala 255 | Tyr 220 | |
| Ile 130 | Thr 105 | Tyr 273 | Leu 256 | Asp 224 | |
| Leu 132 | Arg 110 | Thr 274 | Leu 259 | His 228 | |
| Val 263 | Lys. 230 | | | Asn 265 | |
| Thr 266 | Asp 231 | | | Asn 268 | |
| Leu 267 | Asn 232 | | | Glu 269 | |
| Phe 270 | Asn 233 | | | Ser 271 | |
| His 275 | Tyr 234 | | | Gly 272 | |
| Val 276 | Lys 236 | | | Asp 288 | |
| Met 277 | Gln 237 | | | Lys 291 | |
| Val 278 | Arg 238 | | | Lys 292 | |
| Ile 279 | Asn 240 | | | His 293 | |
| Gly 280 | Asp 241 | | | Gln 295 | |
| Gly 281 | Glu 242 | | | Arg 297 | |
| Gly 282 | Asn 243 | | | Asp 298 | |
| Ala 283 | Lys 244 | | | Glu 299 | |
| Leu 285 | Ser 246 | | | Arg 300 | |
| Ile 286 | Ile 247 | | | Lys 303 | |
| Ala 289 | Thr 249 | | | Asn 305 | |
| Val 290 | Glu 250 | | | Asn 306 | |
| Phe 301 | Asn 253 | | | Asn 313 | |
| Ser 307 | Glu 254 | | | Leu 317 | |
| Tyr 309 | Arg 257 | | | Ile 318 | |
| Leu 311 | Lys 258 | | | Gly 319 | |
| Val 312 | Glu 260 | | | Asn 320 | |
| Gly 314 | Gln 261 | | | | |
| Met 315 | Arg 262 | | | | |
| Tyr 316 | Leu 264 | | | | |

Buried Residues

Suitably residues shown as 'buried' in table A are not mutated. Thus suitably residues in the polypeptide part of an ADP binding molecule of the invention which correspond to ParM residues shown as 'buried' in table A are not mutated relative to ParM (SEQ ID NO:1). In other words, suitably residues in the polypeptide part of an ADP binding molecule of the invention shown as 'buried' in table A comprise the same residue as at the corresponding position in ParM (SEQ ID NO:1).

Thus in some embodiments, the polypeptide component of the ADP binding molecule of the invention suitably comprises amino acid sequence having 100% sequence identity to those residues shown as 'buried' in table A.

Intermediate Residues

Suitably residues shown as 'intermediate' in table A may be mutated. Thus suitably residues in the polypeptide part of an ADP binding molecule of the invention which correspond to ParM residues shown as 'intermediate' in table A may be mutated relative to ParM (SEQ ID NO:1). In other words, suitably residues in the polypeptide part of an ADP binding molecule of the invention shown as 'intermediate' in table A may comprise a different residue (or no residue) from the corresponding position in ParM (SEQ ID NO:1).

In some embodiments, the polypeptide component of the ADP binding molecule of the invention suitably comprises amino acid sequence having at least 68% sequence identity to those residues shown as 'intermediate' in table A. This is because, of the 56 residues disclosed as 'intermediate', suitably at least about 18 residues are considered to be useful to mutate with regard to enhanced function as discussed herein. Not all of the mutations taught herein may be needed in each setting, depending on the eventual use of the ADP binding molecule as explained herein. Therefore, in some embodiments, fewer than 18 of the residues shown as 'intermediate' in table A might be mutated. Thus, in some embodiments, the polypeptide component of the ADP binding molecule of the invention suitably comprises amino acid sequence having at least 70% sequence identity to those residues shown as 'intermediate' in table A, suitably least 74% sequence identity, suitably least 78% sequence identity, suitably least 82% sequence identity, suitably least 86% sequence identity, suitably least 90% sequence identity, suitably least 94% sequence identity, suitably least 98% sequence identity to those residues shown as 'intermediate' in table A.

However, it should be noted that these 'intermediate' residues are in fact partially buried. Thus, suitably these 'intermediate' residues are only mutated by substitution with a conservative residue relative to ParM. In other words, suitably the non-identical residues noted above comprise only conservative substitutions relative to the corresponding residue in ParM.

Conservative substitutions may be made for example according to the table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

More suitably residues shown as 'intermediate' in table A are not mutated. Thus suitably residues in the polypeptide part of an ADP binding molecule of the invention which correspond to ParM residues shown as 'intermediate' in table A are not mutated relative to ParM (SEQ ID NO:1). In other words, suitably residues in the polypeptide part of an ADP binding molecule of the invention shown as 'intermediate' in table A comprise the same residue as at the corresponding position in ParM (SEQ ID NO:1).

Exposed Residues

Suitably residues shown as 'exposed' in table A may be mutated. Thus suitably residues in the polypeptide part of an ADP binding molecule of the invention which correspond to ParM residues shown as 'exposed' in table A may be mutated relative to ParM (SEQ ID NO:1). In other words, suitably residues in the polypeptide part of an ADP binding molecule of the invention shown as 'exposed' in table A may comprise a different residue (or no residue) from the corresponding position in ParM (SEQ ID NO:1).

In some embodiments, the polypeptide component of the ADP binding molecule of the invention suitably comprises amino acid sequence having at least 30% sequence identity to those residues shown as 'exposed' in table A, suitably at least 40% sequence identity, suitably at least 50% sequence identity, suitably at least 60% sequence identity, suitably at least 65% sequence identity, suitably at least 70% sequence identity, suitably at least 75% sequence identity, suitably at least 80% sequence identity, suitably at least 85% sequence identity, suitably at least 90% sequence identity, suitably at least 95% sequence identity, suitably at least 98% sequence identity, suitably at least 99% sequence identity, most suitably 100% identity to those residues shown as 'exposed' in table A.

ADP Binding Molecules

In order to construct ADP binding molecules comprising fluorescent ParM variants, which respond to ADP binding, two different strategies were employed. The first relied on the attachment of single fluorophores which are sensitive to environmental changes. Positioned at the edge of the nucleotide binding cleft, the local environment of a fluorophore is altered upon ADP-induced cleft closure and hence the fluorescence may report ADP binding. The second approach takes advantage of the large difference in rhodamine fluorescence depending if the fluorophore is in a monomeric or dimeric state. The basis for this fluorescence change has been described (24-26). This strategy has been used to monitor cleavage of small peptides by proteinases, e.g. elastase and the malaria protease PfSUB-1 (27-29). When attached to both ends of a peptide, rhodamines form a stacking interaction which largely quenches their fluorescence. This interaction is lost upon cleavage of the peptide yielding an up to 30-fold increase in fluorescence intensity (29). This approach can also be used to monitor conformational changes in proteins when the distance or relative orientation of two attached rhodamines is altered. A doubly rhodamine-labeled phosphate binding protein was developed achieving a 20-fold fluorescence increase upon ligand binding (30).

Here we describe the development of ParM variants which respond to ADP binding with a large fluorescence increase, using rhodamine double labeling and/or coumarin single labeling. ADP binding molecules are described that discriminate against ATP and have very low ATPase activity. A preferred ADP binding molecule variant with a coumarin fluorophore has high affinity for ADP, such that it is likely to bind every molecule of ADP produced during a kinase or ATPase assay. An example of this is disclosed herein as MDCC-ParM (His6/I27C/T174A/T175N/C287A).

Another variant with rhodamine labeling has weaker binding, so that the labeled ParM can be present at low concentration, but the fraction bound with ADP is dependent on the ADP concentration in the medium. An example of this is disclosed herein as 6-ATR-ParM (D63C/D224C).

Thus, ADP binding molecules with different characteristics which can be selected for, or tailored to, different experimental systems are provided by the present invention.

In a broad aspect the invention relates to a ParM polypeptide for use as an ADP sensor molecule or ADP binding molecule. Such a ParM polypeptide may be full length (i.e. comprising all 320 amino acid residues corresponding to SEQ ID NO:1 (whether or not substitutions relative to SEQ ID NO:1 are made in the particular amino acids present)) or truncated. Suitably truncated forms of the ParM polypeptide are those which lack a small number of amino acid residues from the N- or C-terminus of the polypeptide relative to wild type ParM. Suitably a small number is 10 or fewer. Suitably such a ParM molecule possesses one or more of the features set out below for the ADP binding molecule of the invention.

Suitably the ADP binding molecule has reduced ATPase activity compared to wild type ParM. Suitably said reduced ATPase activity is mediated by mutation of the ATPase active site of ParM.

Suitably the ADP binding molecule has reduced ATP binding compared to wild type ParM. Suitably said reduced ATP binding is mediated by mutation of the ATPase active site of ParM. Suitably said mutation is by substitution of amino acid residue T174 and/or T175 of wild type ParM. Advantageously, the polypeptide part of the molecule of the invention comprises substitutions relative to the ParM sequence shown as SEQ ID NO: 1 in order to enhance selectivity for ADP. Such substitutions may be chosen by any suitable strategy. A first approach is to design mutations which may weaken binding to ATP. Secondly, it may be possible to sterically block the gamma phosphate binding site by choosing appropriate alternative substitutions. Substitutions designed by any of these two strategies or by a further strategy may advantageously be combined for additive or synergistic effect. Throughout this type of substitution, it is preferred not to select substitutions which might decrease the affinity for ADP, or at least to select substitutions which only minimally adversely affect the affinity for ADP. In this regard, suitably mutations such as substitutions are made at one or more of the amino acids corresponding to D6, S9, E148, D170, T174, T175, more suitably substitutions are made at one or more of the amino acids corresponding to T175, T174, E148 or S9. These substitutions find particular application in enhancing ADP selectivity of rhodamine-labelled ParM variants. Most suitably, substitutions are made at acids corresponding to T174 and or T175. Particularly advantageous substitutions include T175L, T175N, T175A and T174A. The substitutions T175N, T174A and T175L are particularly advantageous, since these substitutions actually increase the ADP affinity of the polypeptide as well as reducing the affinity for ATP and therefore they increase the selectivity by both mechanisms. Combinations of these substitutions may also be made. Especially preferred are molecules which comprise a T175N substitution, molecules which comprise a T175L substitution and molecules which comprise a T174A and T175N double substitution.

Most preferably molecules of the invention comprise one or more substitutions for enhanced selectivity for ADP in combination with one or more substitutions for attachment of a reporter moeity such as a fluorophore. In particular, most suitably substitutions for enhanced selectivity for ADP are combined with an I27C substitution.

Thus, in another aspect, the invention relates to an ADP binding molecule comprising a polypeptide, said polypeptide comprising amino acid sequence corresponding to at least amino acids 11 to 310 of SEQ ID NO:1, wherein said polypeptide comprises a substitution or substitutions relative to SEQ ID NO:1 selected from:
(iv) T175N; or
(v) T174A and T175A; or
(vi) T174A and T175N; or
(vii) T174A and T175L; or
(viii) T175L.

Thus, in another aspect, the invention relates to an ADP binding molecule comprising a polypeptide, said polypeptide comprising amino acid sequence corresponding to at least amino acids 11 to 310 of SEQ ID NO:1, wherein said polypeptide comprises a substitution or substitutions relative to SEQ ID NO:1 selected from:
(iv) T175N; or
(v) T174A and T175A; or
(vi) T174A and T175N; or
(vii) T175L.

Suitably the ADP binding molecule shows reduced filament formation compared to wild type ParM. Suitably said reduced filament formation is mediated by mutation of the ATP binding site of ParM. Suitably said mutation is by substitution of one or more amino acid residues corresponding to D58, K33, R34, W36, or F40 of wild type ParM. Mutation (such as substitution) of one or more of these residues has the advantage of being most suitable to inhibit filament formation.

Suitably the ADP binding molecule of the invention is, and may be used as, a reagentless biosensor.

A hexahistidine tag (6his) may be added to the polypeptide part of the ADP binding molecule of the invention to simplify purification; most suitably a C-terminal hexahistidine tag is used.

Moreover, since the ADP binding molecules of the invention are reliant only on ADP binding and not any particular enzymatic activity or peripheral chemical components, they are robust sensors for use in a wide range of buffers or experimental conditions.

Reporter Moieties/Attachment Sites

The ADP binding molecule of the invention suitably comprises one or more reporter moieties. The reporter moiety may be any suitable chemical group or structure capable of reading out change(s) in the conformation of said ADP binding molecule. Most suitably the reporter moiety comprises one or more fluorophore(s) such as coumarin or rhodamine.

Reporter moieties used in the invention can give various signals, but preferred labels are luminescent labels. Luminescent labels include both fluorescent labels and phosphorescent labels. However, the use of other labels is envisaged. For example, electrochemical labels could be used wherein alteration in the environment of the labels will give rise to a change in redox state. Such a change may be detected using an electrode. Most suitably fluorescent labels which may be excited to fluoresce upon exposure to certain wavelengths of light are used. The fluorescent label can be selected from the group consisting of rhodamines, cyanines, pyrenes and derivatives thereof. Preferred fluorescent fluorophores are based on a xanthene nucleus, which can readily undergo stacking to form dimers. Especially suitable are rhodamine fluorophores.

Suitably the reporter moiety comprises any usable fluorescent label. Fluorescent labels with environmentally sensitive fluorescence are likely to be better. When a cysteine is the site of attachment, then the moiety needs thiol-reactivity for attachment. In other embodiments, an amine-sensitive label on the non-Cys protein may be employed.

In some embodiments, reporter moieties may be those that can exhibit molecular stacking, which will thus include aromatic rings. These include the rhodamine labels. In other embodiments labels which do not stack may be used, such as coumarin labels.

Dye stacking is a non-covalent interaction between two chromophores having planar aromatic rings, and it occurs when the rings are separated by a distance that is short enough to allow them to interact e.g. to form dimers or trimers. The detectable signal of the stacked molecules is different from that of the unstacked molecules (e.g. stacking can cause quenching of signals, and so stacked chromophores will typically show a decreased fluorescence signal intensity relative to the individual unstacked chromophores), and this difference can be used to detect the presence or absence of stacking. Stacked chromophores can have absorption spectra with (i) a characteristic decrease in the principal absorption peak as chromophore concentration increases and (ii) a characteristic shoulder peak ('band splitting').

For example, rhodamine chromophores can form dimers at high concentrations in solution. The dimer has a different absorbance spectrum from the monomer, and has little or no fluorescence in comparison with the monomer. Two rhodamine chromophores attached to suitable positions in the protein can form dimers, whose interaction is altered when ligand binds to the protein. The invention can spectroscopically detect the difference between the ADP-free and ADP-bound conformations of ADP binding molecule. Molecular stacking takes place through the physical interaction of ground states of the two moieties. Labels that can undergo molecular stacking are well known in the art. Stacking can occur between identical chromophores, and can also occur between different chromophores.

Suitably fluorophores may include one or more of

MDCC, N-[2-(1-maleimidyl)ethyl]-7-diethylaminocoumarin-3-carboxamide;
IDCC, N-[2-(iodoacetamido)ethyl]-7-diethylaminocoumarin-3-carboxamide);
MIANS, 2-(4'-maleimidylanilino)naphthalene-6-sulfonic acid;
5-IATR, 5-iodoacetamidotetramethylrhodamine;
Alexa 488, AlexaFluor-488-maleimide;
MPrCC, N-[3-(1-maleimidyl)-1-propyl]-7-diethylaminocoumarin-3-carboxamide;
CPM, 7-diethylamino-3-[4'-(1-maleimidyl)phenyl]-4-methylcoumarin;
acrylodan: 6-acryloyl-2-dimethylaminonaphthalene.

Especially suitable fluorophores are mentioned in the examples section, particularly in table 1.

In some embodiments, the ADP binding molecule comprises one or more fluorophore(s) attached via an amino acid corresponding to C287 of ParM. In these embodiments, suitably a decrease in fluorescence indicates an increase in ADP binding.

In other embodiments the polypeptide comprises a C287 substitution such as C287A. In these embodiments an alternative attachment site is used. C287 is a solvent exposed cysteine residue. The inventors teach that this is can be problematic to use as a fluorophore attachment site due to its proximity to other functional elements on the ParM derived polypeptide. Thus an advantage of substituting this residue is a molecule with enhanced functionality. Another advantage of substitution of C287 is improvement of targeting of the fluorophore (or other reporter moiety) attachment since substitution prevents attachment at amino acid 287. Thus, when substituting C287, any amino acid residue unsuitable for (or resistant to) attachment of a fluorophore or other reporter moiety is used; most suitably a C287A substitution is made. Unless otherwise stated, polypeptide components of the ADP binding molecule of the invention comprise a C287 substitution, in particular C287A.

Alternative attachment site(s) may be used. Suitably an amino acid residue suitable for use in attachment, such as a cysteine residue, is introduced elsewhere in the polypeptide (i.e. at one or more position(s) other than the naturally occurring cysteines) for use as an attachment site. Thus, suitably the polypeptide may comprise one or more substitutions selected from amino acids corresponding to I27, D58, D63, S204, T215, K216, or D224 of ParM.

Suitably the polypeptide may comprise combinations of two or more such substitutions. Particularly suitable combinations of substitutions include D63 and K216; D63 and D224. Suitably each substitution intended for attachment is a substitution to cysteine e.g. I27C. Each of these substitutions is suitably combined with a C287 substitution such as C287A. These multiple attachment site embodiments of the invention have the advantage of allowing multiple fluorophores to be attached to the same polypeptide. This permits signal amplification and more suitably permits use of fluorophore stacking to enhance signal and provide more robust readout compared to other techniques. Thus multiple attachment sites such as two or more attachment sites are preferred when fluorophore stacking is used in the readout.

A most preferred substitution is I27C. This is particularly preferred in combination with C287A. This is particularly suitable for single fluorophore embodiments.

Thus, particular substitutions may be especially suitable for different reporter moieties. Examples of such combinations are presented in table 1. This is discussed in more detail below.

Conjugation Chemistry

Reporter moieties or labels such as fluorophores may be attached to the ADP binding molecule of the invention by any suitable means known in the art. Suitably the fluorophores are attached by conventional conjugation techniques such as covalent attachment via a cysteine residue in the polypeptide component of the ADP binding molecule.

The covalent attachment of extrinsic reporter moieties to proteins is well known. Different cysteine residues show different reactivities to labelling reagents, which can be assessed using DTNB (5,5'-dithio-bis(2-nitrobenzoic acid)).

Reporter moieties can be attached via amines or carboxyl residues on amino acid side chains, but it is more suitable to use covalent linkage via thiol groups on a cysteine residue. Where more than one label is attached to a protein, these are suitably attached to separate amino acid residues.

Where a cysteine residue has to be introduced, either by insertion or substitution, a number of factors should be considered. These are discussed in more detail herein. Exemplary sites for introduction of Cys residues and thus for label attachment include one or more of I27C, D63C, K216C or D224C.

If attached chromophores are to interact, the residues must be selected such that they are in proximity to each other, and that the conformational change that occurs on ADP-binding affects one or both of the residues to cause a change in position or orientation or electronic environment of a label attached thereto. Exemplary pairs of attachment sites include D63C and K216C; or D63C and D224C.

Exemplary attachment techniques are presented in the examples section.

Readouts

A key concept of the invention is that the ADP binding molecules (sensor proteins) are configured so that they undergo a conformational change upon ADP binding. It is detection of this conformational change which allows the ADP binding status of the molecules of the invention to be determined. Clearly, where the technology permits, single molecule conformational changes may be determined. However, for most embodiments of the invention, determination of the conformational status of the ADP binding molecule is suitably assessed as a population effect. In other words, assessing the conformational change of an ADP binding molecule of the invention may be carried out by determining the conformational change of a population of ADP binding molecules of the invention. Considering those embodiments where the conformational change is read out or detected by monitoring changes in the behaviour of a reporter moiety coupled to the ADP binding molecule of the invention, this idea may be explained as follows. For the purposes of illustration, the reporter moiety will be considered to be a fluorophore. The fluorophore is attached to the ADP binding molecule of the invention. ADP binding leads to a conformational change of the ADP binding molecule. This conformational change can lead to a change in fluorescence. This change in fluorescence may be an increase or a decrease upon ADP binding depending on the particular labelling strategy used. For any given application having a fixed amount of sensor protein, the change in fluorescence will be consistently associated with the corresponding change in ADP binding. ADP binding is proportional to the concentration of ADP present in the sample being studied. Therefore, changes in ADP binding provide information about changes in the ADP concentration in the sample being studied. Thus, changes in fluorescence which are catalysed by conformational changes in the ADP binding molecule of the invention brought about by ADP binding directly provide information about the concentration of ADP in the sample being studied. For the great majority of applications or embodiments of the invention, conformational changes will be detected for a population of ADP binding molecules according to the invention. In practical terms, this means that a certain amount of the ADP binding molecule of the invention will be added to the sample being studied. The fluorescence of this population of ADP binding molecules of the invention will then be monitored. Thus, changes in the fluorescence of these molecules represents an indication of the ADP binding status of a proportion or a population of those molecules present in the sample.

Thus, it will be clearly understood that the level of fluorescence varies directly with the amount of ADP binding of the ADP binding molecules of the invention. Thus, this will give the effect of an almost continuously variable level of fluorescence depending on the level of ADP binding (and thus the ADP concentration) within the sample. At one extreme, there will be no ADP binding to any of the ADP binding molecules of the invention. At the other extreme, all of the ADP binding molecules of the invention present in the sample will each be bound to ADP such that there is saturation and complete (or near complete) binding and therefore a 100% signal. Thus, within these two extremes, the particular level of fluorescence is directly correlated to a particular concentration of a ADP in the sample. Thus, in some embodiments of the invention, a standard curve may be constructed by measuring the fluorescence of a constant amount of the ADP binding molecule of the invention in the presence of differing known concentrations of ADP. This standard curve may then be used in order to read out or convert measured fluorescence values to absolute concentrations of ADP present in a sample.

In another embodiment, the readout of the invention may be advantageously calibrated by inclusion of samples having known ADP concentrations in the analysis being undertaken. In these embodiments, the samples containing known concentrations of ADP may be regarded as "internal controls". This permits accurate estimation of ADP concentrations in experimental settings where reference to a standard curve is less appropriate, for example in complex reaction mixtures in which other components might perturb the readouts, or might not have been present during the construction of a standard curve, thereby making such comparisons potentially inappropriate.

Definitions

The term 'comprises' (comprise, comprising) should be understood to have its normal meaning in the art, i.e. that the stated feature or group of features is included, but that the term does not exclude any other stated feature or group of features from also being present.

MDCC-PBP is used to refer to the A197C mutant of phosphate binding protein of E. coli labeled with MDCC.

6-ATR-ParM is used to refer to an adduct of ParM with two molecules of 6-IATR.

An ADP binding molecule is a molecule capable of binding ADP. Use of the term ADP binding molecule does not imply or require that ADP is present. ADP binding molecule means molecule capable of binding ADP.

Further Applications

It will be apparent to the skilled reader that the main focus of the invention is in the monitoring or measurement of ADP levels. This may be advantageously applied in the setting of determining ADP concentrations in static or stable samples. Alternatively, due to the fast responding fluorescent mode of measurement in preferred embodiments of the invention, the sensor molecules may be used to follow changes in ADP concentration dynamically in real time. Thus, further applications of the invention may be based on this mode of measurement. For example, it is possible to apply the invention to the monitoring of depletion of ADP. More commonly, and more suitably, the invention is applied in order to monitor increases in the concentration of ADP.

It is a particular advantage of the invention that it may be used to directly interrogate or monitor chemical or biological processes which affect ADP concentration. For example, many biological enzymes use ATP and produce ADP as a secondary product as the reaction progresses. One example of such a system is the study of helicase action. Many helicases consume ATP as they proceed along the nucleic acid which they are acting upon. This consumption of ATP leads to a release of ADP, and therefore the progress of the helicase reaction can be monitored by studying the level of ADP released. The same applies to many different enzymes of this general type, including topoisomerases and the like.

A key application of the invention is in the monitoring of certain biological or chemical processes which consume ATP but do not release inorganic phosphate (Pi). Most prior art systems for monitoring the progress of such processes use the release of inorganic phosphate as the parameter to be assessed. However, such an approach has serious limitations. Many reactions consuming ATP do not lead to the release of inorganic phosphate. Therefore, the present invention finds application in a range of biological or chemical processes which are unable to be studied by existing conventional phosphate monitoring techniques. An important example of such a class of reaction is a kinase reaction. Kinases consume ATP in the course of their catalytic action. However, of course a kinase enzyme does not release inorganic phosphate, but rather incorporates the phosphate into its target or substrate. However, kinase reactions typically produce ADP as a by-product of the catalysis of ATP. Thus, the invention finds particular application in the monitoring of kinase reactions.

The invention finds application in monitoring ADP levels in high throughput screening.

The invention also relates to the use or ParM or a polypeptide based on or derived from ParM as an ADP binding molecule. In particular the invention relates to the use of ParM in the manufacture of an ADP binding molecule such as an ADP sensor molecule. The invention also relates to the use of ParM in determination of ADP concentration.

In another aspect, the invention relates to development of the bacterial actin, ParM, as a reagentless biosensor for fluorescent determination of ADP with high time resolution.

In other aspects the invention finds application in monitoring assays such as DNA helicase, ATPases such as those involved in Fe—S cluster assembly, protein kinase, hexokinase, or any other assays in which ADP levels may change and may therefore usefully be read out using a sensor according to the present invention.

Excitation and emission spectra of 1 µM MDCC-ParM (I27C/C287A) (solid lines) and 1 µM MDCC-ParM (His$_6$/I27C/T174A/T175N/C287A) (dashed lines) were recorded in the absence of ADP (lower intensity) and in presence of 100 µM ADP (high intensity). Excitation and emission wavelength were 431 nm and 474 nm, respectively with 5 nm slit width. Spectra were measured in 30 mM Tris.HCl buffer pH 7.5, 25 mM KCl and 3 mM MgCl$_2$ at 20° C.

Figure 2A:
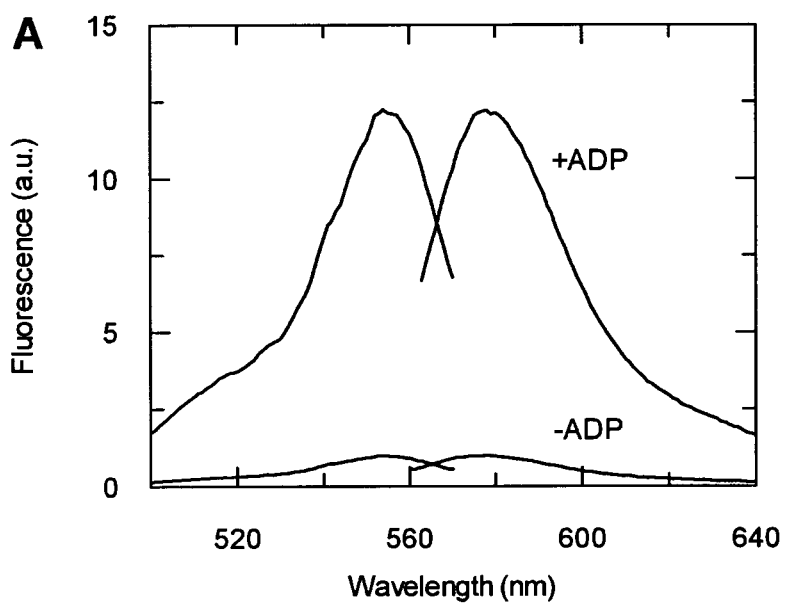

FIG. 2: Fluorescence and Absorbance Spectra of Doubly Rhodamine-Labeled ParM.

(a) Fluorescence excitation and emission spectra of 6-ATR-ParM (D63C/D224C/C287A) alone and in presence of 5 mM ADP. Spectra were recorded at 553 nm and 578 nm excitation and emission wavelengths with 5 nm slit width. (b) Absorbance spectra of 6-ATR-ParM (D63C/D224C/C287A) alone (solid line) and in presence of 0.4 mM (dotted line) and 5 mM (dashed line) ADP. All spectra were measured in 30 mM Tris buffer pH 7.5, 25 mM KCl and 3 mM MgCl$_2$ at 20° C. The spectra show an isosbestic point at 536 nm.

Figure 3:
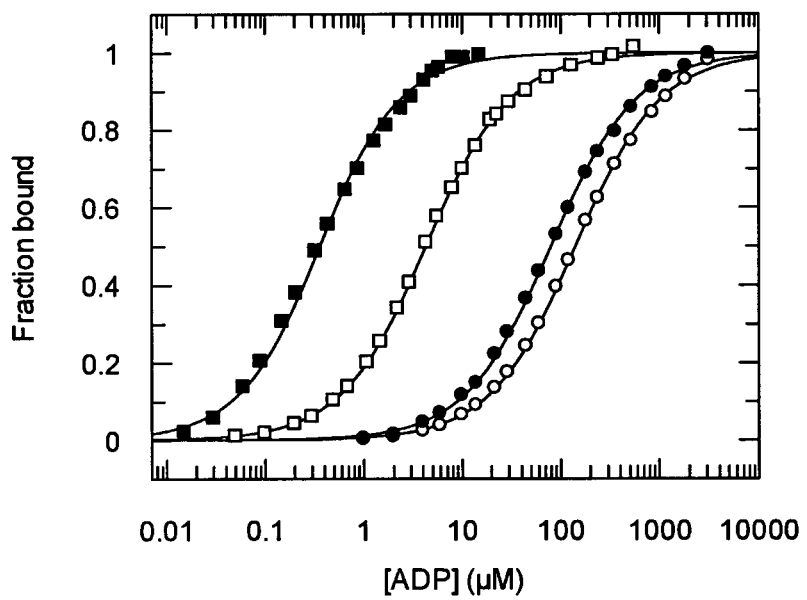

FIG. 3: ADP Affinity of Different ParM Mutants Labeled with MDCC and IATR.

0.1 µM MDCC-ParM (I27C/C287A) (filled squares), 5- and 6-ATR-ParM (D63C/D224C/C287A) (closed and open circles, respectively) and 5-ATR-ParM (D63C/K216C/C287A) (open squares) were titrated with ADP and the fluorescence intensity was recorded. MDCC fluorescence was excited at 431 nm and detected at 474 nm, for the rhodamine-labeled proteins, excitation and emission wavelengths of 553 nm and 578 nm were used. Quadratic binding curves (see Experimental Methods) were fitted to the experimental data yielding the dissociation constants 0.31 µM, 80 µM, 140 µM and 4.2 µM for MDCC-ParM (I27C/C287A), 5- and 6-ATR-ParM (D63C/D224C/C287A) and 5-ATR-ParM (D63C/K216C/C287A), respectively. The fraction of ParM bound to ADP was calculated from the fluorescence intensities. All titrations were performed in 30 mM Tris.HCl buffer pH 7.5, 25 mM KCl, 3 mM MgCl$_2$ and 5 µM BSA at 20° C.

Figure 4:
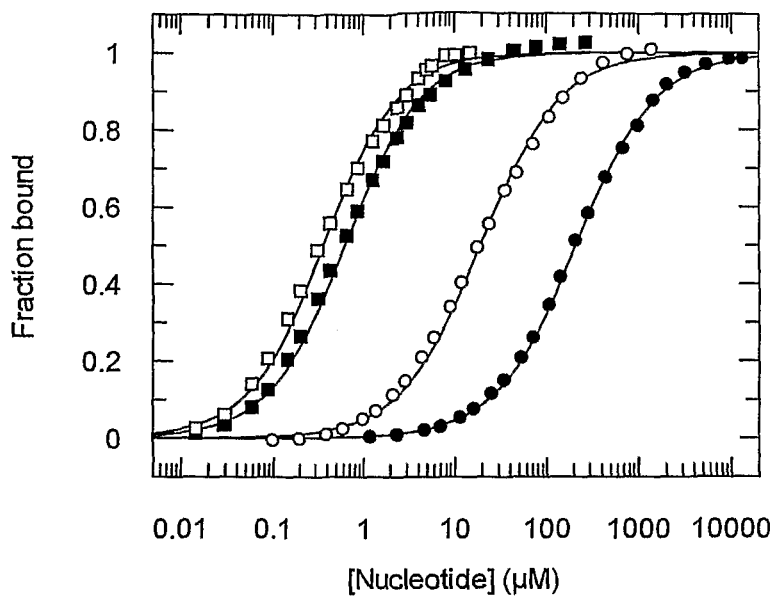

FIG. 4: ADP and ATP BINDING AFFINITY of MDCC-Labelled ParM Mutants.

MDCC-ParM (I27C/C287A) (open symbols) and MDCC-ParM (His$_6$/I27C/T174A/T175N/C287A) (closed symbols), both at a concentration of 0.1 µM, were titrated with ADP (squares) and ATP (circles). The titration data of MDCC-ParM (I27C/C287A) are the same as in FIG. 3. The MDCC fluorescence was excited at 431 nm and emission was recorded at 474 nm. The equilibrium dissociation constants were determined by fitting a quadratic binding curve to the data. The $K_d$-values obtained from the fits are listed in Table 2. For the plot the experimental fluorescence intensities were converted to the nucleotide bound fraction of ParM. The titrations were performed in 50 mM Tris.HCl buffer pH 7.5, 25 mM KCl, 3 mM MgCl$_2$ and 5 µM BSA at 20° C. (except MDCC-ParM (I27C/C287A), titrated with ADP, where 30 mM Tris was used).

Figure 5A:
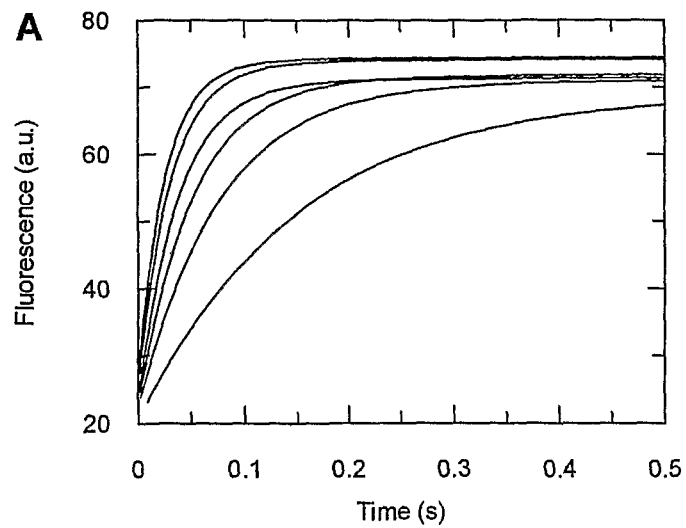

FIG. 5: Kinetics of ADP BINDING to MDCC-ParM Mutants.

Association kinetics were measured under pseudo-first order conditions by mixing 0.5 µM MDCC-ParM with increasing concentrations of ADP in a stopped-flow apparatus. The fluorescence was excited at 436 nm and emission was detected through a 455 nm long-pass filter. (a) Time courses of fluorescence change upon ADP binding to MDCC-ParM (His$_6$/I27C/T174A/T175N/C287A) at different ADP concentrations (10, 20, 30, 40, 50 and 60 µM). Data are well described by single exponential curves (not shown) yielding the observed rate constants, $k_{obs}$. (b) Secondary plot of the $k_{obs}$ versus ADP concentration for the MDCC-ParM (His$_6$/I27C/T175L/C287A) (open circles), (His$_6$/I27C/T174A/T175N/C287A) (closed circles) and (His$_6$/I27C/T174A/T175A/C287A) (triangles). The association rate constants obtained from the slope of linear regression analysis are shown in table 3. (c) Dissociation kinetics of ADP from MDCC-ParM (His$_6$/I27C/T174A/T175N/C287A). The preformed complex of MDCC-ParM and ADP (0.5 and 2 µM) was mixed in the stopped-flow with 100 µM (upper trace) or 200 µM (lower trace) of unlabeled ParM mutant. The fluorescence was recorded as in panel a. The rate constants determined from single exponential fits to the two traces are 0.20 s$^{-1}$ and 0.19 s$^{-1}$. The value obtained from the experiment with 200 µM displacer is listed as dissociation rate constant in Table 3. All stopped-flow measurements were carried out in 30 mM Tris.HCl buffer pH 7.5, 25 mM KCl and 3 mM MgCl$_2$ at 20° C.

FIG. 6: Fluorescence Response of the Final Coumarin Biosensor in the Absence and Presence of ATP.

Figure 1:
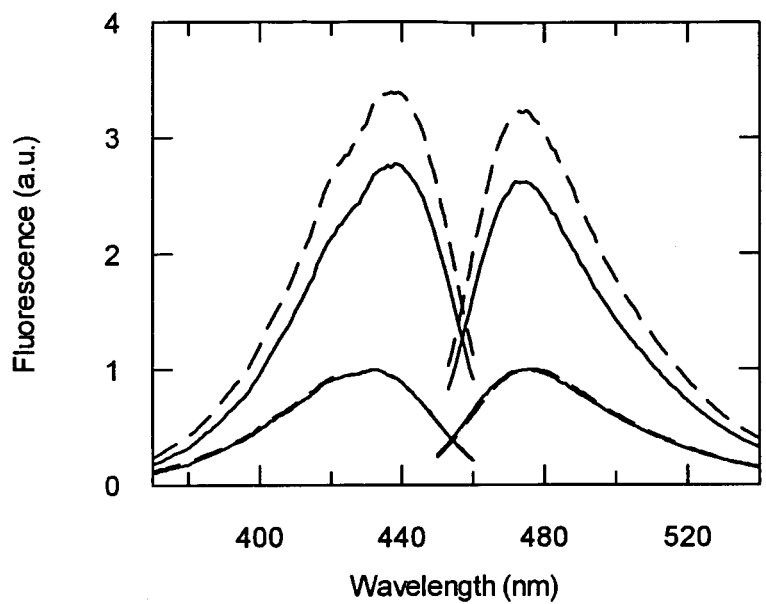
FIG. 1: Fluorescence Spectra of MDCC-Labeled ParM Mutants.
Figure 6A:
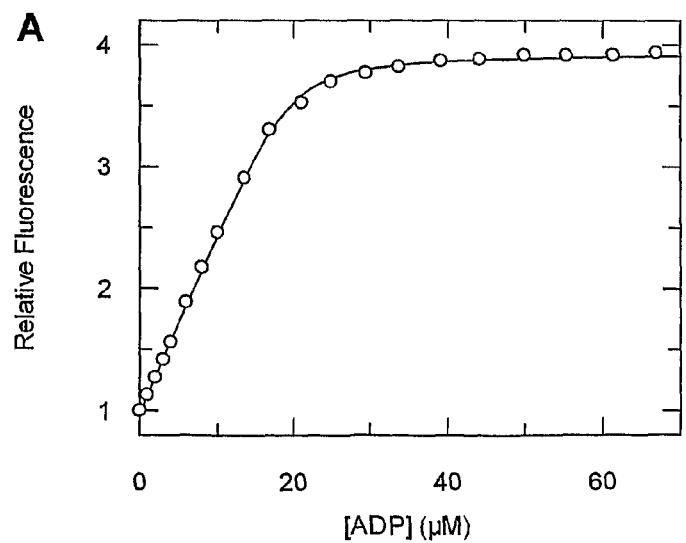
Figure 6B:
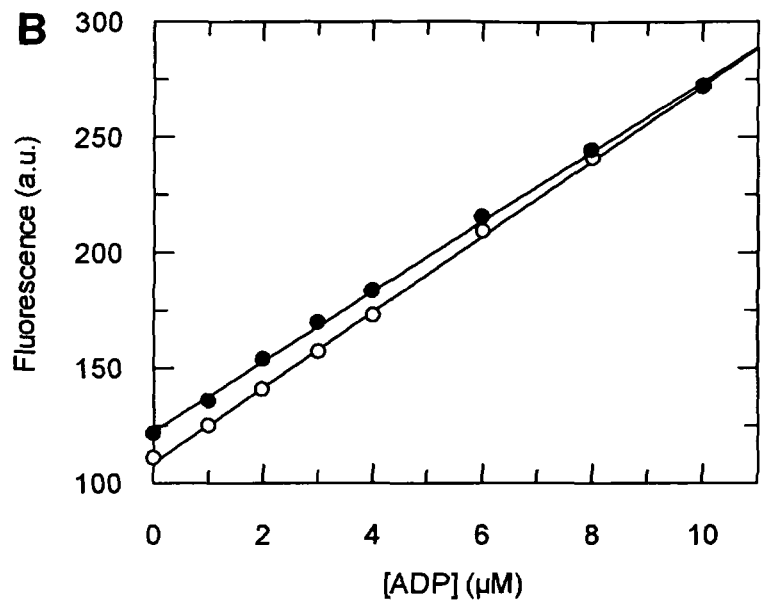
Figure 7A:
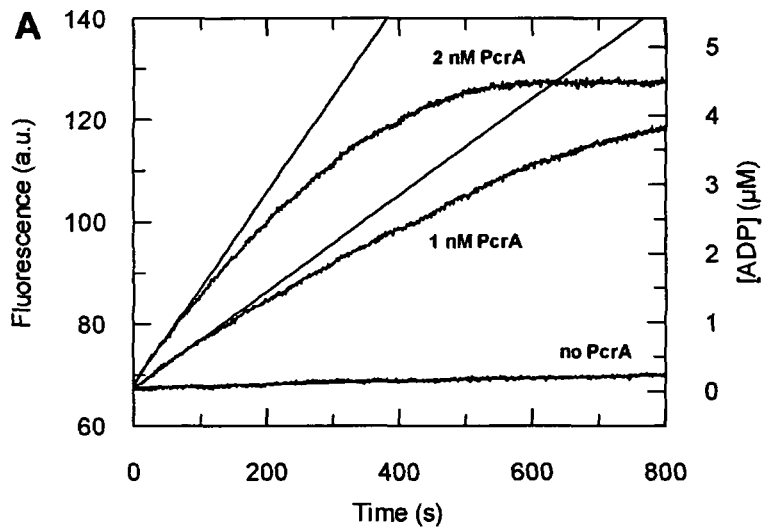
Figure 7B:
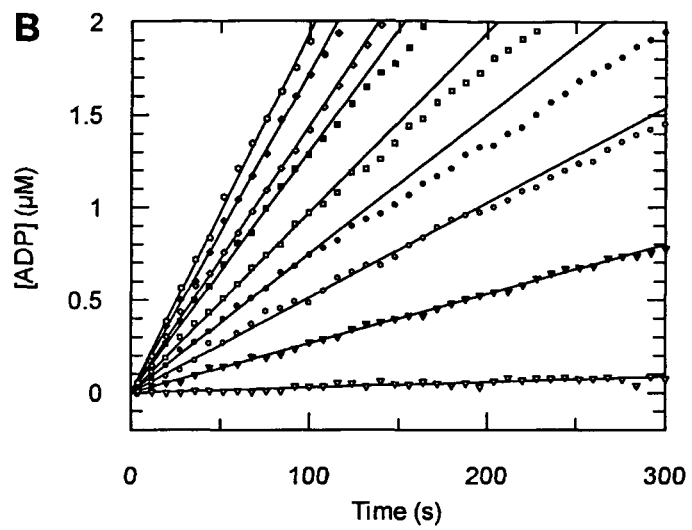
Figure 7C:
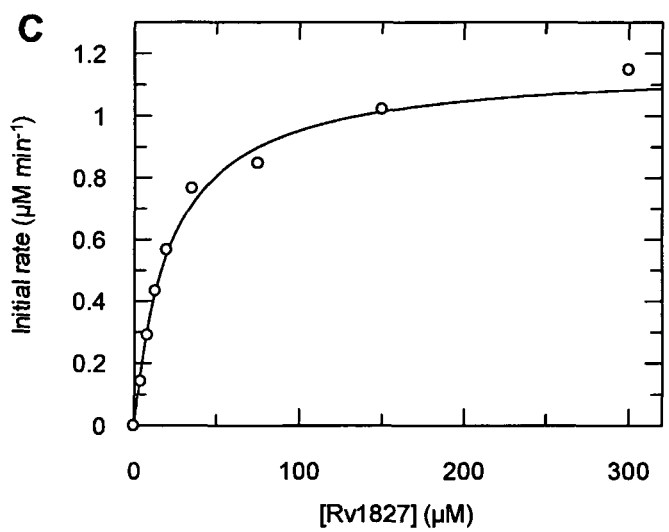

(a) Active site titration of MDCC-ParM (His$_6$/I27C/T174A/T175N/C287A) with ADP. 20 µM MDCC ParM was titrated with ADP and the fluorescence was recorded as in FIG. 1. Data were normalized to the fluorescence intensity observed in the absence of ADP. A quadratic binding curve was fitted to the data, where the dissociation constant was fixed at the value determined before and the ParM concentration was allowed to vary. The resulting concentration of active sites is 19.3 µM conforming to the ParM concentration determined from absorbance spectra. (b) Comparison of the fluorescence response in the absence and presence of ATP. Open circles show part of the titration curve from panel a up to 10 µM, where the signal is linearly dependent on ADP concentration with a slope of 16.3 µM$^{-1}$. In a second experiment (closed circles) the fluorescence intensity of 20 µM MDCC-ParM was measured at different ATP/ADP ratios but a constant nucleotide concentration ([ATP]+[ADP]=10 µM). As with ADP alone, the fluorescence shows a linear dependence on the ADP concentration but the slope of the linear regression, 15.1 µM$^{-1}$, is slightly lower:

FIG. 7: Kinetic Assays Using MDCC-PBP (a) ATP hydrolysis of PcrA helicase moving along single stranded DNA. ADP generation of PcrA when translocating along ssDNA was monitored using the ADP sensor MDCC-ParM. 10 µM MDCC-ParM, 3.8 µM dT$_{16}$ and 1 nM, 2 nM or no PcrA were pre-incubated in the cuvette and the reaction was started by the addition of 5 µM ATP. MDCC fluorescence was excited at 431 nm and emission was detected at 474 nm. The assay was calibrated by measuring the fluorescence intensity of MDCC-ParM at a constant nucleotide (ATP+ADP) concentration of 5 µM and increasing ADP content as shown in FIG. 6b. The initial rates were determined by linear regression to the data points below 10% ATP turnover, resulting in rates of 10.4 and 19.9 nM s$^{-1}$ at 1 nM and 2 nM PcrA, respectively. In the absence of PcrA a rate of 0.633 nM s$^{-1}$ is obtained. The experiment was carried out in 50 mM Tris buffer pH 7.4, 150 mM NaCl and 3 mM MgCl$_2$ at 20° C. (b) Phosphorylation of Rv1827 by the protein kinase PknB. Time courses of ADP generation during phosphorylation of Rv1827 by PknB. The kinetics were measured with 0.2 µM PknB, 40 µM ATP, 10 µM MDCC-ParM and different concentrations of the substrate Rv1827 in 30 mM Tris buffer pH 7.5, 150 mM NaCl, 3 mM MgCl$_2$ and 2 mM DTT at 20° C. The MDCC fluorescence was monitored as before. Calibration was performed analogous to FIG. 6 with 40 µM total nucleotide concentration and increasing ADP concentration up to 5 µM. Solid lines show the linear fits to determine the initial rates. A control measurement was performed without the substrate Rv1827 and initial rates were corrected for this background activity. (c) Dependence of the initial rate on the Rv1827 concentration. Data were analysed according to the Michaelis-Menten equation, yielding $K_M$=22 µM and $V_{max}$=1.2 µM min$^{-1}$.

Figure 8:
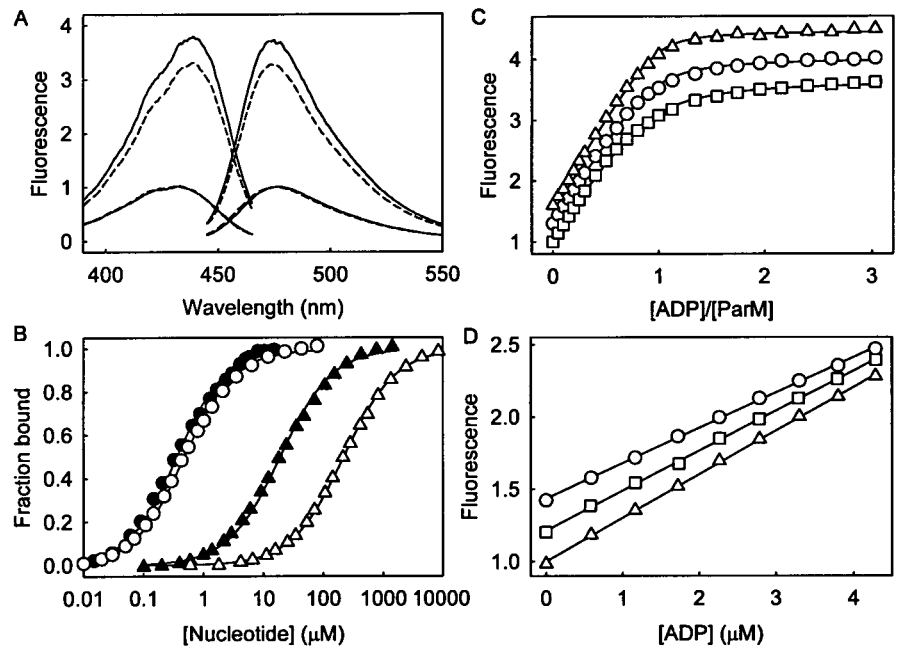

FIG. 8: Development of the MDCC-ParM based ADP sensor.

A, Fluorescence excitation and emission spectra of 1 µM MDCC-ParM (I27C/C287A) (dashed lines) and 1 µM MDCC-ParM (His6/I27C/K33A/T174A/T175N/C287A) (solid lines) in the absence of ADP (lower intensity) and in presence of 200 µM ADP (high intensity). Spectra were recorded at excitation and emission wavelength of 436 nm and 474 nm, respectively, with 5 nm slit width. B, Titration of MDCC-ParM (I27C/C287A) (solid symbols) and MDCC-ParM (His6/I27C/K33A/T174A/T175N/C287A) (open symbols), both at a concentration of 0.1 µM, with ADP (circles) and ATP (triangles). Data were analyzed using a quadratic binding curve (Equation 1 in Experimental Procedures). The dissociation constants obtained from these fits are shown in Table Z. C, Active site titrations of 5 µM (squares), 10 µM (circles) and 20 µM (triangles) MDCC-ParM (His6/I27C/K33A/T174A/T175N/C287A) with ADP. Curve fitting was performed as in B, but Kd was fixed to the value obtained in B and only the ParM concentration was allowed to vary. The results for the active site concentrations were 4.5 µM, 9.7 µM and 19.8 µM. D, Comparison of the fluorescence response in the absence and presence of ATP. 10 µM MDCC-ParM only (triangles) and MDCC-ParM plus 20 µM ATP (squares) or 40 µM ATP (circles) were titrated with ADP. In the last two experiments the total nucleotide concentration [ATP]+[ADP] was held constant at 20 µM or 40 µM and only the proportion of ADP was changed. The fluorescence response is linear with slopes of 0.305, 0.283 and 0.252 µM-1 at 0, 20 and 40 µM ATP, respectively.

Figure 9:
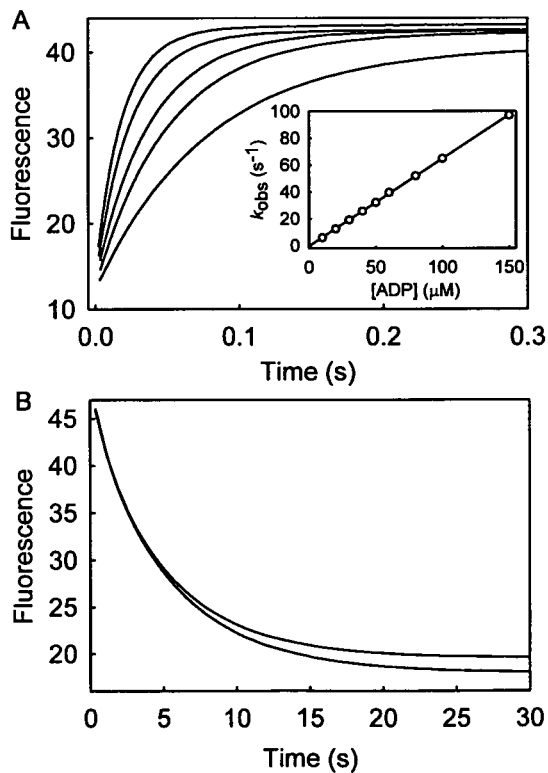

FIG. 9: Association and Dissociation Kinetics of ADP with MDCC-ParM

A, Association kinetics were measured under pseudo-first order conditions by mixing MDCC-ParM with ADP in a stopped-flow apparatus. Time courses of fluorescence change upon ADP binding to 0.25 µM MDCC-ParM are shown at different ADP concentrations (20, 30, 40, 50, 60 and 80 µM). The time courses shown are the average of three individual stopped-flow traces. Data are well described by single exponential curves yielding the observed rate constants, kobs. Inset: Secondary plot of the observed rate constants versus ADP concentration. The association rate constant, 0.65±0.01 µM-1 s-1, was obtained from the slope of a linear regression analysis. B, Dissociation kinetics of ADP from MDCC-ParM. The preformed complex of MDCC-ParM and ADP (0.5 and 2 µM) was mixed in the stopped-flow with 100 µM (upper trace) or 200 µM (lower trace) of unlabeled ParM mutant. Three individual traces were averaged to obtain the time courses shown. The rate constants determined from single exponential fits to the experimental data with 100 µM and 200 µM displacer are 0.20±0.01 s-1 and 0.18±0.01 s-1, respectively.

Figure 10:
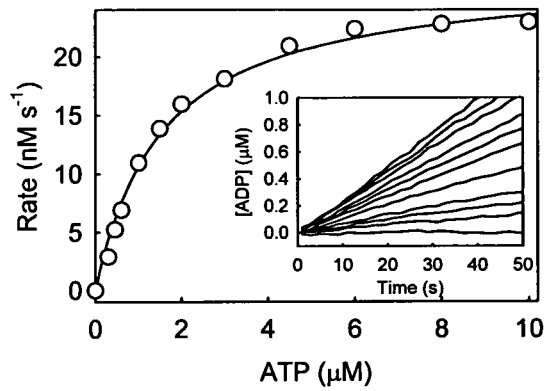

FIG. 10: ATP Hydrolysis by PcrA Helicase During Translocation Along Single Stranded DNA ADP generation of PcrA when translocating along ssDNA was monitored using the ADP sensor MDCC-ParM. 5 µM MDCC-ParM, 0.5 µM dT20 and different concentrations of ATP were pre-incubated in the cuvette and the reaction was started by the addition of 2 nM PcrA. ADP concentrations were calculated from the fluorescence signal using the calibration method described in the text. Time courses of ADP generation at different ATP concentrations (from bottom to top 0, 0.3, 0.45, 0.6, 1, 1.5, 2, 3, 4.5, 8 and 15 µM) are in the inset. The initial rates were determined by linear regression to data points below 10% ATP turnover and plotted versus ATP concentration. The parameters KM, 1.6 µM, and kcat, 13.7 s-1, were obtained from a curve fit according to the Michaelis-Menten equation.

Figure 11:
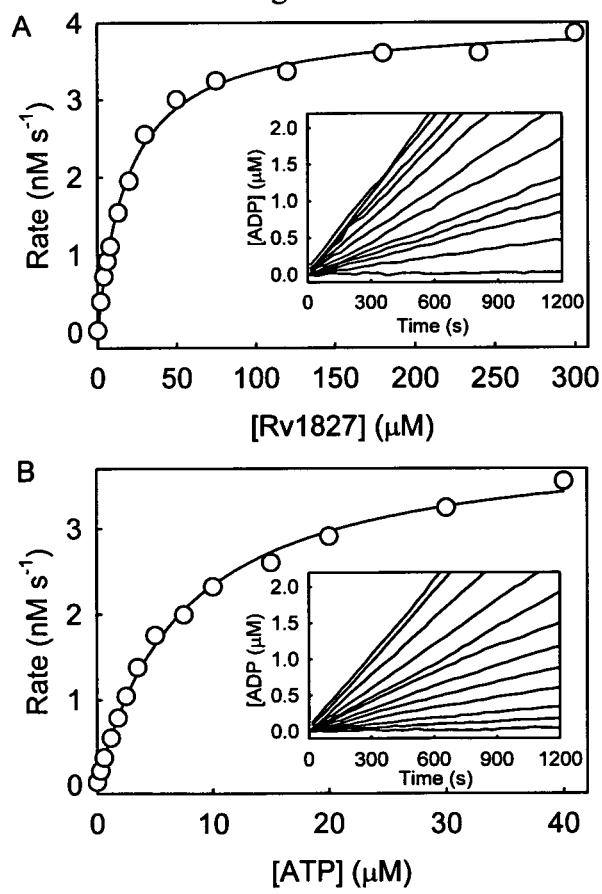

FIG. 11: Phosphorylation of Rv1827 by the Protein Kinase PknB.

Phosphorylation of Rv1827 by the protein kinase PknB was measured using the MDCC-ParM biosensor to monitor the kinetics of ADP generation. The experiments were carried out as described for the helicase assay with 50 nM PknB, 10 µM MDCC-ParM and constant 40 µM ATP or 300 µM Rv1827, varying the concentration of the second substrate Rv1827 or ATP. A, Plot of initial rates against the concentration of Rv1827. Data were analyzed according to the Michaelis-Menten equation, yielding KMRv1827 20 µM and kcat 4.7 min-1. Inset: Time courses of ADP generation during phosphorylation of Rv1827 by PknB measured at different concentrations of the protein substrate Rv1827 (from bottom to top 0, 2, 4, 6, 8, 13, 20, 30, 50, 75, 180 and 300 µM). B, Plot of initial rates against the concentration of ATP. Curve fitting results in the Michaelis-Menten parameters KMATP 7.5 µM and kcat 4.9 min-1. Inset: Time courses of ADP generation measured at different concentrations of the ATP (from bottom to top 0, 0.3, 0.6, 1.2, 1.8, 2.5, 3.5, 5, 7.5, 15, 30 and 40 µM).

Figure 12:
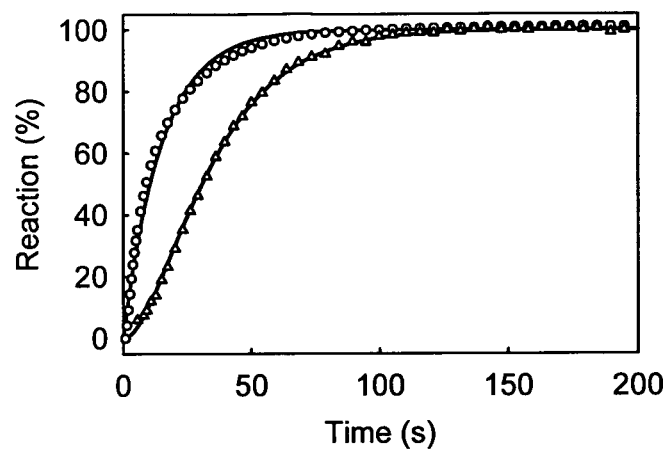

FIG. 12: Phosphate and ADP Release During a Single Turnover of ATP Hydrolysis by SufBC Phosphate release (circles) and ADP release (triangles) were measured using the biosensors MDCC-PBP and MDCC-ParM, respectively. In a stopped-flow apparatus 13 µM SufBC and either 20 µM MDCC-PBP or 80 µM MDCC-ParM were mixed with 4 µM ATP and the fluorescence was recorded. Data represent averages of three individual stopped-flow traces. Single exponential curve fitting to the phosphate release data (solid line) gives a rate constant of 0.066±0.001 s-1. ADP release data were analyzed using a double exponential function (solid line), assuming a reaction sequence of two irreversible steps, where ADP is released in the second step. This results in the first order rate constants of the two steps, 0.058±0.001 s-1 and 0.050±0.002 s-1.

Figure 13:
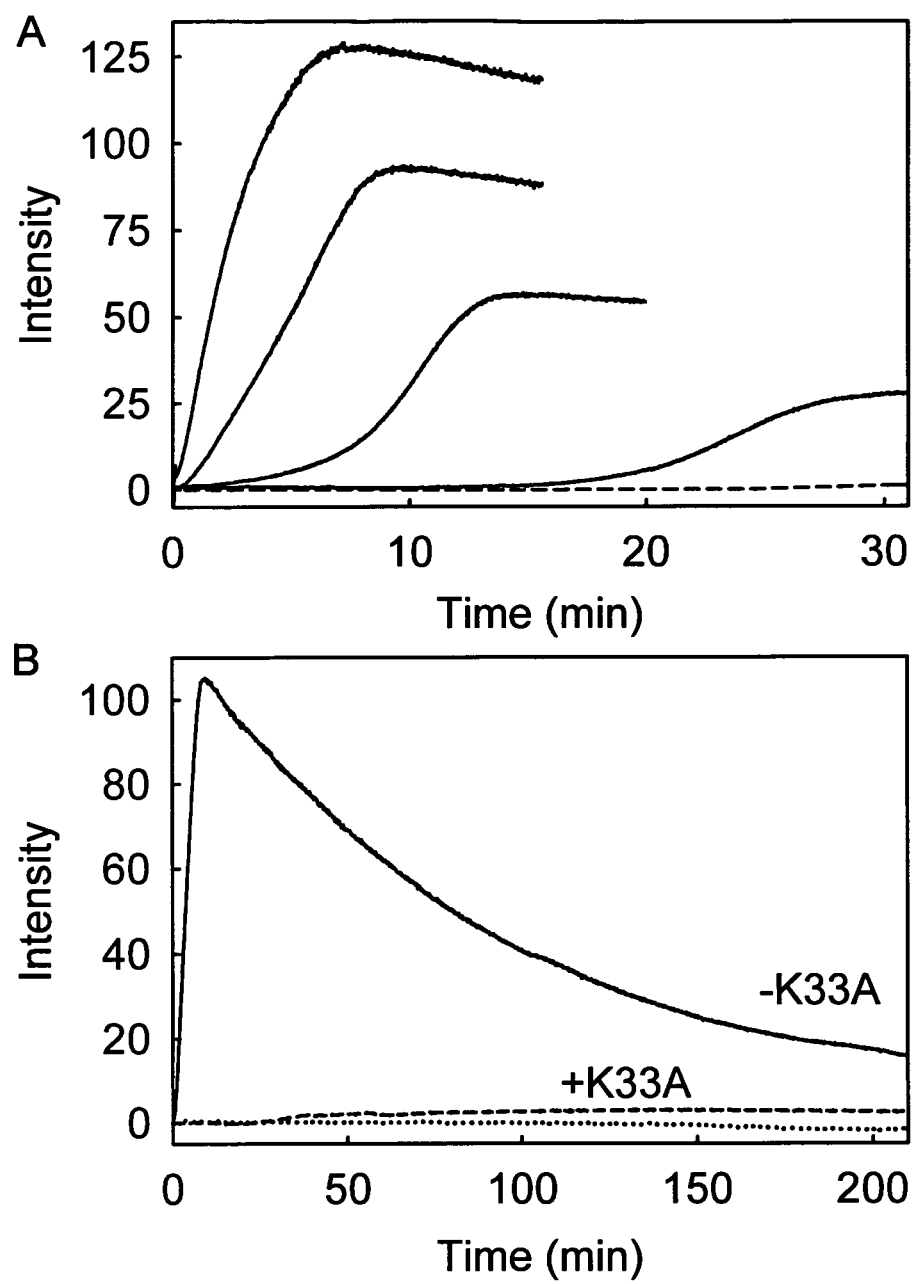

FIG. 13: Filament Formation of MDCC-Labeled ParM Mutants.

Polymerization of ParM was monitored by measuring right angle light scattering at 340 nm in a spectrofluorimeter. A, Change in light scattering observed in solutions of 10, 20, 30 and 40 µM MDCC-ParM (His$_6$/I27C/T174A/T175N/C287A) after addition of 4 mM ATP (solid lines) or 4 mM ADP (dashed line). From the maximum scattering intensities at different ParM concentrations the critical concentration in presence of ATP was determined to 2.5 µM. B, Comparison of the polymerization behavior of 40 µM MDCC-ParM (His$_6$/I27C/T174A/T175N/C287A) (solid line) with 40 µM (dotted line) or 120 µM (dashed line) MDCC-ParM (His$_6$/I27C/K33A/T174A/T175N/C287A) after addition of 4 mM ATP. The additional K33A mutation effectively blocks filament formation. Light scattering assays were carried out in 30 mM Tris.HCl pH 7.5, 25 mM KCl and 3 mM MgCl$_2$ at 20° C.

Figure 14:
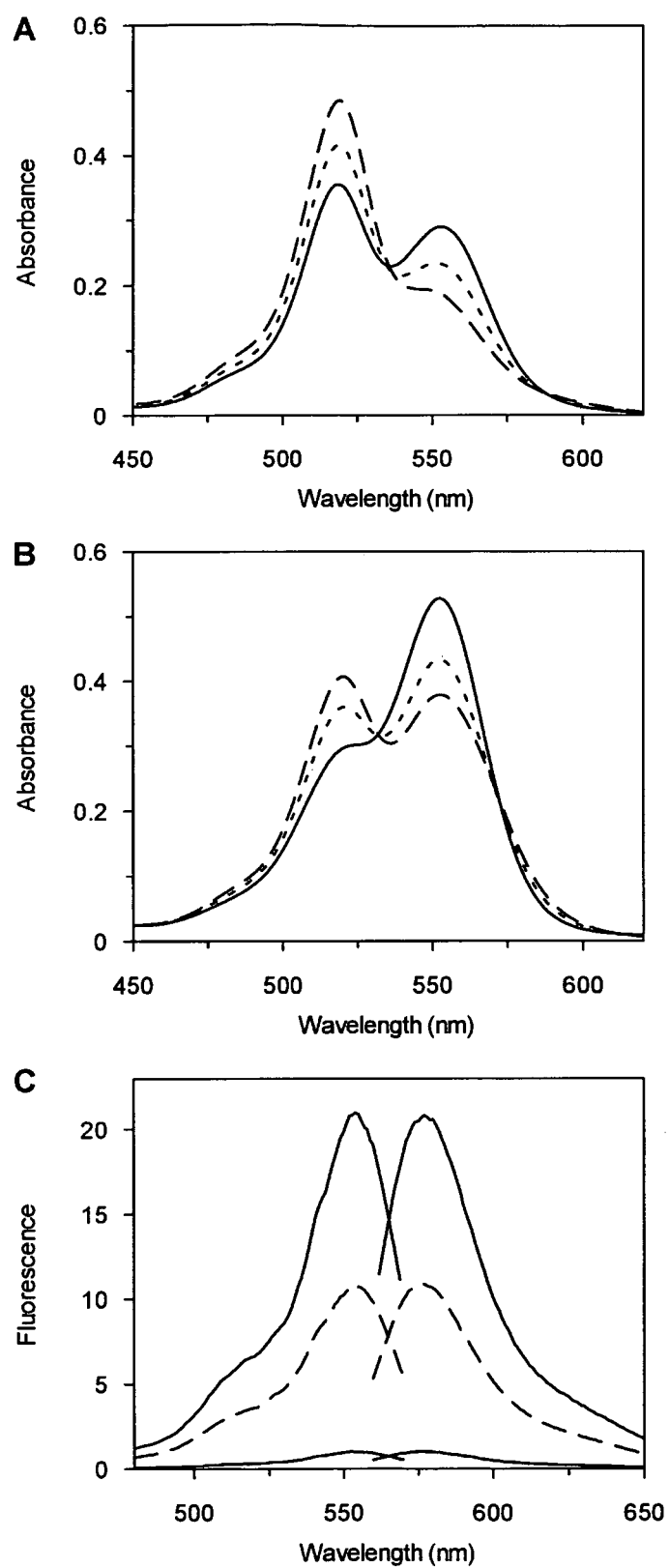

FIG. 14: Absorbance and Fluorescence Spectra of Rhodamine Labeled ParM Mutants.

(A, B) Absorbance spectra of 6-IATR (A) and 5-IATR (B) labeled ParM (His$_6$/K33A/D63C/T174A/T175N/D224C/C287A) alone (solid line) and in presence of 40 µM (A) or 30 µM (B) ADP (dotted line) and 4 mM ADP (dashed line). The spectra show isosbestic points at 536 nm (A) and 532 nm (B). Spectra of the original IATR-labeled ParM mutant (D63C/D224C/C287A) are virtually identical to those shown. (C) Fluorescence excitation and emission spectra of 5-IATR-labeled ParM (His$_6$/D63C/T174A/T175N/D224C/C287A) (solid lines) and ParM (His$_6$/K33A/D63C/T174A/T175N/D224C/C287A) (dashed lines) at 1 µM in the absence of ADP (lower intensity) and in presence of 4 mM ADP (higher intensity). Spectra were recorded at 553 nm and 578 nm excitation and emission wavelengths. Spectra were normalized by dividing the measured intensities by the maximum fluorescence in the absence of ADP. Fluorescence spectra of 6-IATR-labeled ParM mutants have essentially the same shape as the 5-IATR-labeled ParM spectra shown. Absorbance and fluorescence spectra were measured in 30 mM Tris.HCl pH 7.5, 25 mM KCl and 3 mM MgCl$_2$ at 20° C.

Figure 15:
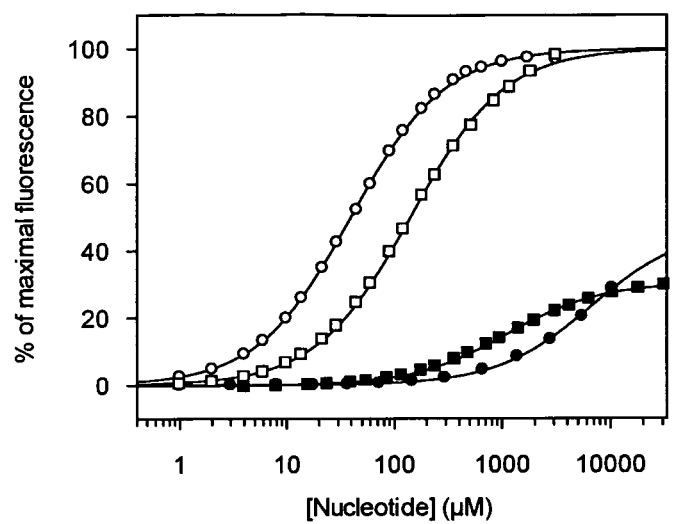

FIG. 15: ADP and ATP Binding Affinity

6-IATR-labeled ParM (D63C/D224C/C287A) (open symbols) and ParM (His$_6$/K33A/D63C/T174A/T175N/D224C/C287A) (closed symbols), both at a concentration of 0.1 µM, were titrated with ADP (circles) and ATP (squares). The rhodamine fluorescence was excited at 553 nm and emission was recorded at 578 nm. The equilibrium dissociation constants were determined by fitting a quadratic binding curve to the data and are listed in Table Y. For the plot the experimental fluorescence intensities were normalized to the maximal fluorescence change obtained at saturation with ADP. Titrations were performed in 30 mM Tris.HCl pH 7.5, 25 mM KCl, 3 mM MgCl$_2$ and 5 µM BSA at 20° C.

Figure 16:
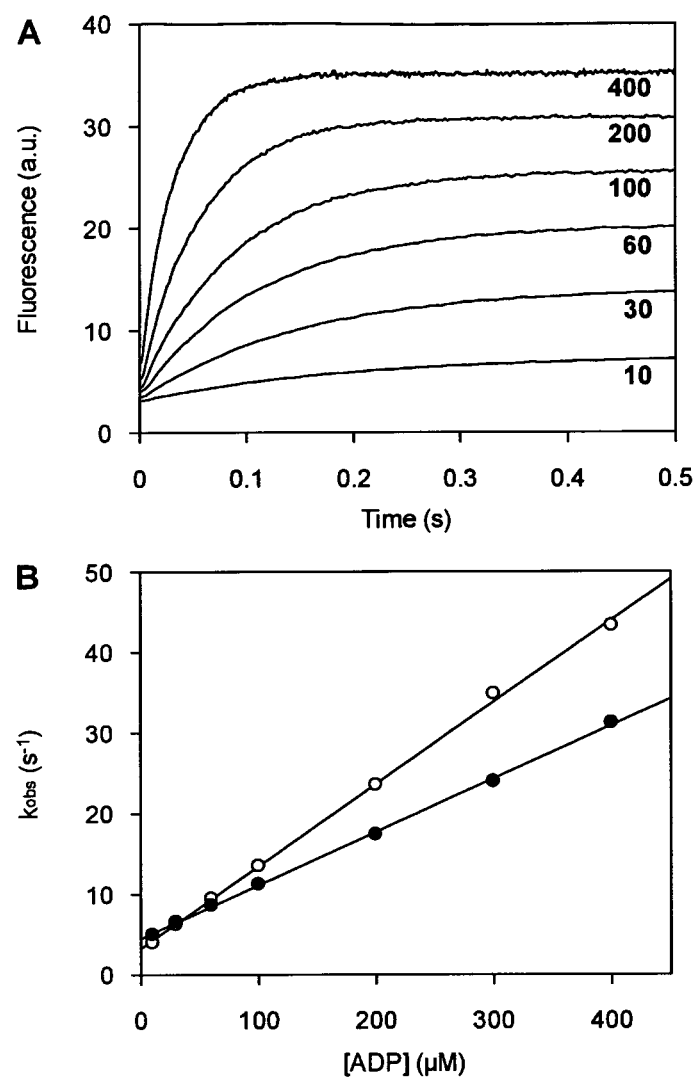

FIG. 16: ADP Binding Kinetics of Rhodamine-Labeled ParM Mutants.

(A) Time courses of the fluorescence change after mixing of 5-ATR-ParM (His$_6$/D63C/T174A/T175N/D224C/C287A) with an excess of ADP in the stopped-flow. The final concentration of 5-ATR ParM was 0.1 µM and the ADP concentrations in µM are indicated in the graph. The data shown are averages of three individual stopped-flow traces. The fluorescence traces are well described by single exponential curves yielding the observed rate constants $k_{obs}$. (B) Plot of the observed rate constants versus ADP concentration for 5-ATR ParM (His$_6$/D63C/T174A/T175N/D224C/C287A) without (closed circles) and with the K33A mutation (open circles). Association and dissociation rate constants obtained from the slope and intercept of linear regression analysis are summarized in Table Y. All experiments were carried out 30 mM Tris.HCl pH 7.5, 25 mM KCl, 3 mM MgCl$_2$ and 5 µM BSA at 20° C.

Figure 17:
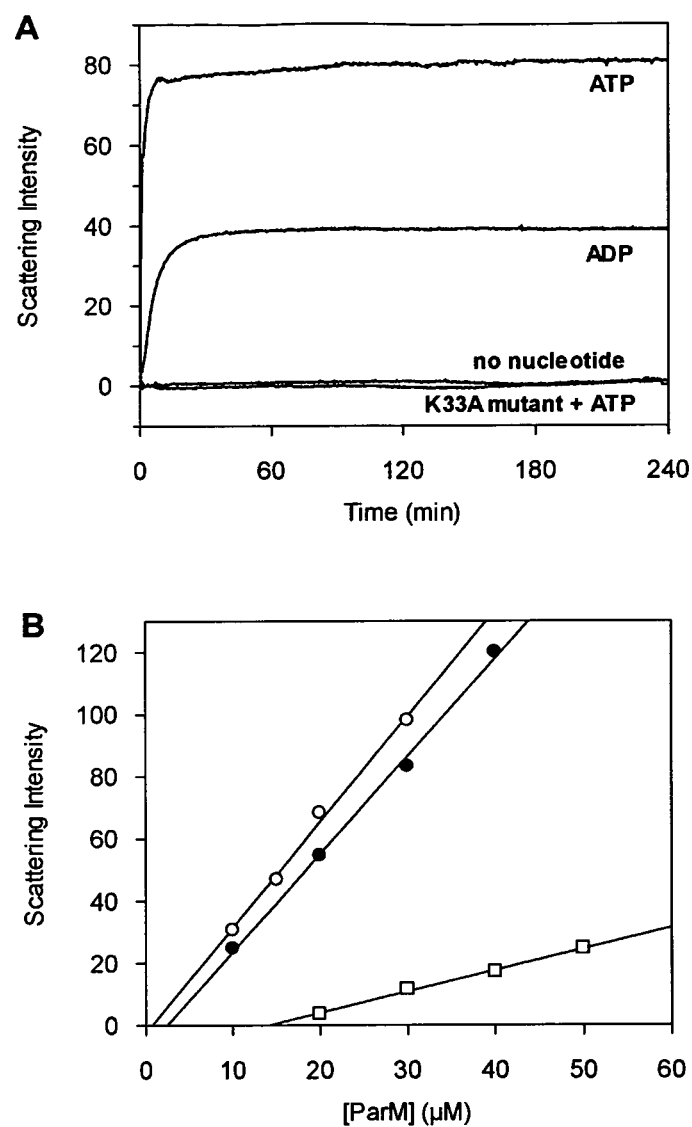

FIG. 17: Filament Formation of Rhodamine-ParM Mutants

Filament formation or ParM was measured in 30 mM Tris.HCl pH 7.5, 25 mM KCl, 3 mM MgCl$_2$ at 20° C. using right angle light scattering at 340 nm. (A) Change in light scattering of a 20 µM solution of 5-ATR ParM (His$_6$/D63C/T174A/T175N/D224C/C287A) after addition of 4 mM ATP, 4 mM ADP or buffer only as indicated in the figure. Data are also shown for 20 µM 5-ATR-ParM (His$_6$/K33A/D63C/T174A/T175N/D224C/C287A) after addition of 4 mM ATP indicating that the K33A mutation efficiently blocks filament formation. (B) Plot of the maximal scattering intensity observed in presence of 4 mM ATP versus concentration of 5-ATR ParM (His$_6$/D63C/T174A/T175N/D224C/C287A) (open circles), 6-ATR ParM (His$_6$/D63C/T174A/T175N/D224C/C287A) (open squares) and wild-type ParM (solid circles). Linear extrapolation to the x-intercept yields the critical concentrations 0.8 µM, 14 µM and 2.5 µM, respectively.

Figure 18:
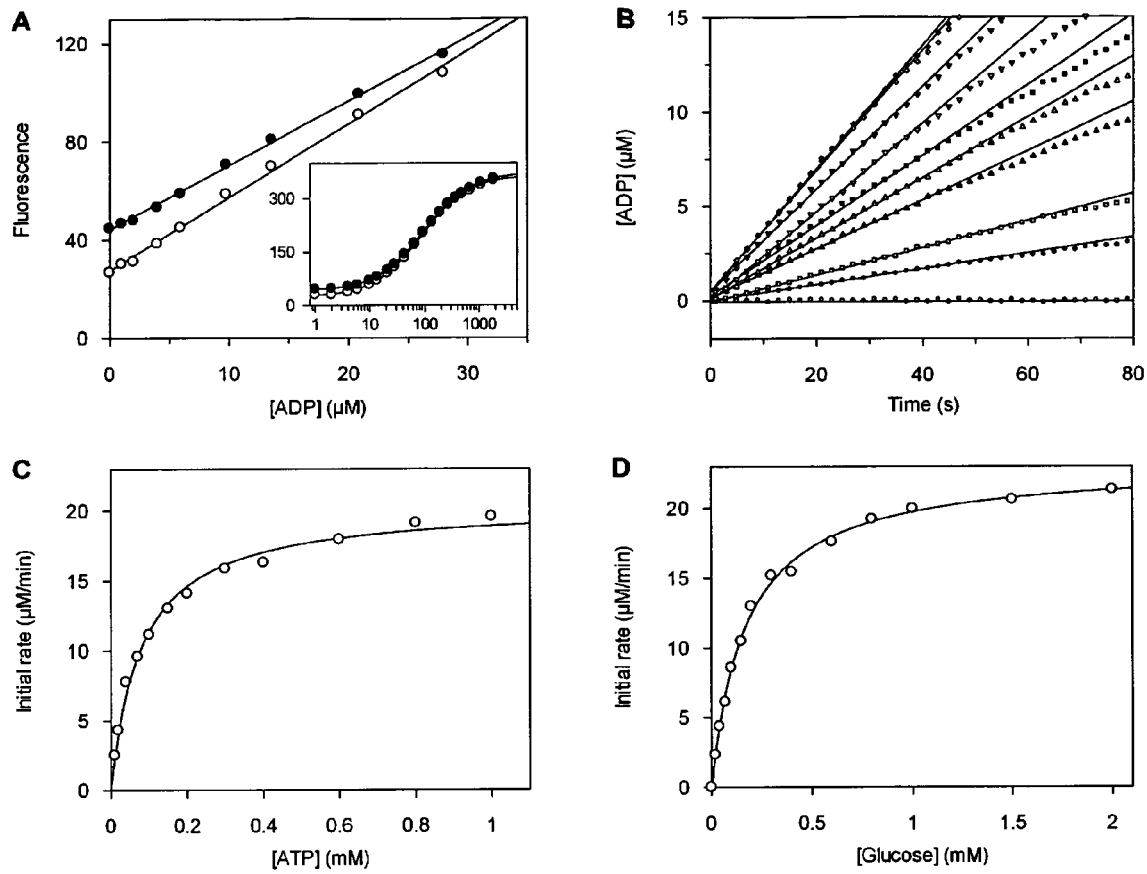

FIG. 18: Steady-State Assay of Hexokinase Activity Using a Rhodamine-ParM ADP Biosensor Phosphorylation of D(+)-glucose by hexokinase was measured by monitoring ADP generation with the fluorescent biosensor 5-ATR ParM (His$_6$/D63C/T174A/T175N/D224C/C287A). Measurements were carried out with 0.02 units/ml hexokinase and 0.5 µM 5-ATR-ParM in 50 mM Tris HCl pH 7.5, 25 mM KCl, 10 mM MgCl$_2$ and 5 µM BSA at 20° C. (A) Calibration of the fluorescence signal. 0.5 µM 5-ATR-ParM was titrated with ADP in the absence (open circles) and in presence of 1 mM ATP. In the concentration range up to 30 µM ADP the fluorescence signal is nearly linear dependent on ADP concentration. The slopes of linear regression analysis of data with 0 and 1 mM ATP are 2.9 µM$^{-1}$ and 2.6 µM$^{-1}$, respectively. The slope in presence of ATP was used for the assay calibration. The inset shows the complete titration curves on a logarithmic scale, the dissociation constants under these conditions were 86 µM and 95 µM. (B) Time courses of ADP generation upon phosphorylation of 2 mM D-glucose by hexokinase at ATP concentrations of 0, 0.01, 0.02, 0.04, 0.07, 0.1, 0.2, 0.4, 0.8, 1 mM (from bottom to top). Solid lines show the linear fits yielding the initial rates. (C) Plot of the initial rates versus ATP concentration. Curve fitting according to the Michaelis-Menten equation results in the parameters $K_M$, 80 µM and $v_{max}$, 20 µM min$^{-1}$. (D) Plot of the initial rates versus D-glucose concentration. Data were measured at constant 1 mM ATP. The Michaelis-Menten parameters from the fitted curve are $K_M$, 170 µM and $v_{max}$, 23 µM min$^{-1}$.

SEQUENCES

See Accompanying WIPO ST.25 Sequence Listing

```
SEQ ID NO: 1 ParM reference sequence
ParM wild-type:
Accession number P11904
The full-length sequence comprises residues 1 to 320
   1 mlvfiddgst niklqwqesd gtikqhispn sfkrewavsf gdkkvfnytl ngeqysfdpi 61 spdavvttni awqysdvnvv avhhalltsg lpvsevdivc tlplteyydr nnqpntenie 121 rkkanfrkki tlnggdtfti kdvkvmpesi pagyevlqel deldslliid lggttldisq 181 vmgklsgisk iygdsslgvs lvtsavkdal slartkgssy laddiiihrk dnnylkqrin 241 denkisivte amnealrkle qrvlntlnef sgythvmvig ggaelicdav kkhtqirder
```

```
301 ffktnnsqyd lvngmylign

SEQ ID NO: 2
MDCC-ParM
ParM (His6/I27C/T174A/T175N/C287A) (variant for MDCC-labelling)
   1 mlvfiddgst niklqwqesd gtikqhcspn sfkrewaysf gdkkvfnytl ngeqysfdpi 61 spdavvttni awqysdvnvv avhhalltsg lpvsevdivc tlplteyydr nnqpntenie 121 rkkanfrkki tlnggdtfti kdvkvmpesi pagyevlqel deldslliid lgganldisq 181 vmgklsgisk iygdsslgvs lvtsavkdal slartkgssy laddiiihrk dnnylkqrin 241 denkisivte amnealrkle qrvlntlnef sgythvmvig ggaeliadav kkhtqirder 301 ffktnnsqyd lvngmylign qsgshhhhhh SEQ ID NO: 3
6-ATR-ParM
ParM (D63C/D224C/C287A) (variant 1 for double rhodamine-labelling)
   1 mlvfiddgst niklqwqesd gtikqhispn sfkrewavsf gdkkvfnytl ngeqysfdpi 61 spcavvttni awqysdvnvv avhhalltsg lpvsevdivc tlplteyydr nnqpntenie 121 rkkanfrkki tlnggdtfti kdvkvmpesi pagyevlqel deldslliid lggttldisq 181 vmgklsgisk iygdsslgvs lvtsavkdal slartkgssy ladciiihrk dnnylkqrin 241 denkisivte amnealrkle qrvlntlnef sgythvmvig ggaeliadav kkhtqirder 301 ffktnnsqyd lvngmylign SEQ ID NO: 4
ParM (D63C/K216C/C287A) (variant 2 for double rhodamine-labelling)
   1 mlvfiddgst niklqwqesd gtikqhispn sfkrewavsf gdkkvfnytl ngeqysfdpi 61 spcavvttni awqysdvnvv avhhalltsg lpvsevdivc tlplteyydr nnqpntenie 121 rkkanfrkki tlnggdtfti kdvkvmpesi pagyevlqel deldslliid lggttldisq 181 vmgklsgisk iygdsslgvs lvtsavkdal slartcgssy laddiiihrk dnnylkqrin 241 denkisivte amnealrkle qrvlntlnef sgythvmvig ggaeliadav kkhtqirder 301 ffktnnsqyd lvngmylign SEQ ID NO: 5-preferred ParM variant for MDCC-labeling (with K33A)
ParM (His6/I27C/K33A/T174A/T175N/C287A)
   1 mlvfiddgst niklqwqesd gtikqhcspn sfarewavsf gdkkvfnytl ngeqysfdpi 61 spdavvttni awqysdvnvv avhhalltsg lpvsevdivc tlplteyydr nnqpntenie 121 rkkanfrkki tlnggdtfti kdvkvmpesi pagyevlqel deldslliid lgganldisq 181 vmgklsgisk iygdsslgvs lvtsavkdal slartkgssy laddiiihrk dnnylkqrin 241 denkisivte amnealrkle qrvlntlnef sgythvmvig ggaeliadav kkhtqirder 301 ffktnnsqyd lvngmylign qsgshhhhhh SEQ ID NO: 6-preferred ParM variant for double rhodamine labelling (K33 WT)
ParM (His6/D63C/T174A/T175N/D224C/C287A)
   1 mlvfiddgst niklqwqesd gtikqhispn sfkrewavsf gdkkvfnytl ngeqysfdpi 61 spcavvttni awqysdvnvv avhhalltsg lpvsevdivc tlplteyydr nnqpntenie 121 rkkanfrkki tlnggdtfti kdvkvmpesi pagyevlqel deldslliid lgganldisq 181 vmgklsgisk iygdsslgvs lvtsavkdal slartkgssy laddiiihrk dnnylkqrin 241 denkisivte amnealrkle qrvlntlnef sgythvmvig ggaeliadav kkhtqirder 301 ffktnnsqyd lvngmylign qsgshhhhhh SEQ ID NO: 7-
preferred ParM variant for double rhodamine labelling with K33A
ParM (His6/K33A/D63C/T174A/T175N/D224C/C287A)
   1 mlvfiddgst niklqwqesd gtikqhispn sfarewavsf gdkkvfnytl ngeqysfdpi 61 spcavvttni awqysdvnvv avhhalltsg lpvsevdivc tlplteyydr nnqpntenie
```

-continued

```
121 rkkanfrkki tlnggdtfti kdvkvmpesi pagyevlqel deldslliid lgganldisq 181 vmgklsgisk iygdsslgvs lvtsavkdal slartkgssy ladciiihrk dnnylkqrin 241 denkisivte amnealrkle qrvlntlnef sgythvmvig ggaeliadav kkhtqirder 301 ffktnnsqyd lvngmylign qsgshhhhhh
```

The invention is now described by way of example. These examples are intended to be illustrative, and are not intended to limit the appended claims.

EXAMPLES

General Methods

Plasmids

Plasmid pJSC1 for recombinant synthesis of ParM wild-type was provided by J. Löwe (MRC Laboratory of Molecular Biology, Cambridge, U.K.) (Salje, Embo, 2008). Point mutations in ParM were introduced by QuikChange site-directed mutagenesis (Stratagene) using pJSC1 as template. ParM variants with a C-terminal His$_6$-tag were constructed by site-directed mutagenesis using the oligonucleotides 5'-GTATCT-CATAGGTAATCAATCAGGATCCCATCAT-CATCATCATG3' and 5'-GATGATGGGATCCTGATTGATTACCTAT-GAGATACATACCG3'. The mutagenic PCR changes the two stop codons after the ParM gene on pJSC1 to codons for Gln and Gly, followed by a one base deletion, so that the vector-encoded His$_6$-tag is expressed. The preferred ADP binding molecule polypeptide ParM (His$_6$) construct contain the 10 amino acid extension QSGSHHHHHH at the C-terminus.

Protein Expression and Purification

ParM variants were synthesized in *E. coli* BL21-AI cells (Invitrogen). ParM expression cultures were grown from freshly transformed BL21-AI cells in 2×TY medium containing 100 μg/ml ampicillin. 3 ml medium were inoculated with cells from the agar plate and incubated at 37° C. for 3 hrs. Cultures were diluted to 25 ml with fresh medium and cells were grown at 37° C. for another 2-3 hrs (OD$^{600}$=1.2 to 1.4). For the main culture 1 or 2×500 ml medium were inoculated with 10 ml of the starter culture. Cells were grown at 30° C. until the OD$^{600}$ had reached between 0.4 and 0.6, when over-expression was induced by addition of 0.0002% arabinose. Cells were harvested 16 his after induction, resuspended in lysis buffer (30 mM Tris-HCl pH 7.5, 25 mM KCl, 1 mM MgCl$_2$, 0.1% Triton X-100) and stored at −80° C. For ParM variants without His6-tag 1 mM DTT was included in the lysis buffer.

ParM variants without His6-tag were purified as described (van den Ent et al., 2002) with the following modification: The final size exclusion chromatography was performed on a HiLoad Superdex 75 column (GE Healthcare) in 30 mM Tris-HCl pH 7.5, 25 mM KCl and 1 mM EDTA. This procedure completely removes DTT and nucleotide present in the preceding polymerisation step. Proteins were concentrated in a Vivaspin 20 centrifugal concentrator with PES membrane (Vivascience) to 30-100 mg/ml. ParM concentrations were determined from the absorbance at 280 nm using the extinction coefficient 34380 M$^{-1}$ cm$^{-1}$ calculated from the primary sequence (Pace et al., 1995). Aliquots were shock-frozen in liquid nitrogen and stored at −80° C.

ParM (His$_6$) mutants were purified by Ni-chelate chromatography: Cleared cell extracts were supplemented with 500 mM NaCl and filtered through a 0.45 μM syringe filter (Satorius). The lysate was loaded onto a 5 ml HisTrap HP column (GE Healthcare) equilibrated with buffer A (30 mM Tris-HCl pH 8.0, 500 mM NaCl). The column was washed with buffer A until the absorbance at 280 nm reached the baseline, followed by 10 column volumes buffer B (30 mM Tris-HCl pH 8.0, 25 mM KCl). ParM was eluted with a linear gradient of 0-500 mM imidazole in buffer B over 20 column volumes. ParM containing fractions were pooled and 10 mM DTT was added. Protein solutions were concentrated using a Vivaspin 20 centrifugal concentrator (Vivascience) prior to loading on a gel filtration column. Size exclusion chromatography was performed as described above.

Labelling of ParM mutants

In order to screen for a fluorescence change upon ADP binding, labeling was performed on a scale of 2-3 mg ParM. ParM mutants (100-150 μM) and 2-fold (maleimides) or 4-fold (iodacetamides) excess of fluorophore over cysteines were incubated in 30 mM Tris-HCl pH 7.5, 25 mM KCl and 1 mM EDTA, end-over-end mixing at 22° C. After 45 min (maleimides) or 90 min (iodacetamides) 2 mM MESNA was added and the solutions were incubated for another 15 min. Reaction mixtures were centrifuged (15000 g, 10 min, 4° C.) and the supernatant was then filtered through a 0.2 μM Acrodisc filter (Pall Corporation). Free fluorophore was removed by two successive PD10 columns (GE Healthcare) using the same buffer as for labelling.

ParM (His$_6$/I27C/T174A/T175N/C287A) was labeled with MDCC on a larger scale (120 mg ParM). The labeling reactions contained 150 μM ParM and 250 μM MDCC in 30 mM Tris-HCl pH 7.5. The reaction mixture was incubated for 35 min, end-over-end mixing at 22° C. 2 mM MESNA was added and incubation was continued for 15 min. The solution was filtered through a 0.2 μM Acrodisc filter (Pall Corporation) and loaded onto a 5 ml HiTrap Q column (GE Healthcare) equilibrated with 30 mM Tris-HCl pH 7.5. The column was washed with the same buffer until the 280 nm absorbance reached baseline. A linear gradient of 0-400 mM KCl over 40 column volumes was applied. The main peak of labelled ParM, eluting at ~130 mM KCl, was pooled and MDCC-ParM was concentrated as described above. The concentration of labelled ParM was determined using the extinction coefficients for MDCC coupled to dithiothreitol, $\square_{430}$=46800 M$^{-1}$ cm$^{-1}$ and $\square_{280}$=7470 M$^{-1}$ cm$^{-1}$ (Brune et al., 1994) and the extinction coefficient of ParM given above.

Nucleotides

ADP and ATP were purchased from Sigma at the highest purity available. The purity of the nucleotides was analysed by HPLC using a Partisphere SAX column, 125×4.5 mm (Whatman). Nucleotide separation was performed isocratic with 0.3 M (NH$_4$)$_2$HPO$_4$ buffer pH 4.0, 25% MeOH, and the absorbance at 260 nm was monitored. The purchased ATP, which was used for the helicase and kinase assays, contained between 0.6 and 0.8% ADP. For determination of the ATP affinity of labeled ParM mutants, the ATP was further purified on a DEAE cellulose column using a linear gradient of 10 mM to 600 mM triethylammonium bicarbonate buffer pH 7.4 over 20 column volumes. This procedure yielded ATP, which contained between 0.02 and 0.03% ADP.

Fluorescence Measurements

Fluorescence spectra, titrations and steady-state activity of PcrA and PknB were measured using a Carry Eclipse fluorescence spectrophotometer (Varian). Assay conditions are given in the respective figure legends. Titration data were analysed using a quadratic binding curve, $$F = F_{min} - (F_{max} - F_{min})\frac{K_d + [P] + [L] - \sqrt{(K_d + [P] + [L])^2 - 4[P][L]}}{2[P]}$$

where [P] and [L] are the total concentrations of protein and ligand, respectively, $K_d$ is the dissociation constant and $F_{min}$ and $F_{max}$ are the fluorescence intensities of the free and ligand bound protein.

Dynamics of ADP binding to MDCC-labelled ParM mutants were measured using a HiTech SF61 DX2 stopped-flow instrument equipped with a Xe/Hg lamp (TgK Scientific, U.K.). Association kinetics were measured under pseudo-first order conditions with at least 10-fold excess of ADP over ParM. In displacement experiments to determine the dissociation rate constants the preformed complex of MDCC-ParM and ADP was mixed with a 50 to 200-fold excess of unlabelled ParM.

All fluorescence measurements were carried out at 20° C.

Example 1

Screening Mutant/Fluorophore Combinations for a Fluorescence Response to ADP

Wild-type ParM contains two cysteine residues: C100 is buried in a hydrophobic core and probably inaccessible to labeling, while C287 is solvent exposed and so likely to be accessible for labeling. As C287 is located in the vicinity of the nucleotide binding sites fluorescent probes attached to this position might report ADP binding. Therefore, the wild-type protein was labeled with a series of different fluorophores and the change in fluorescence upon ADP binding was measured (Table 1).

nocoumarin-3-carboxamide; MIANS, 2-(4'-maleimidylanilino)naphthalene-6-sulfonic acid; MPrCC, N-[3-(1-maleimidyl)-1-propyl]-7-diethylaminocoumarin-3-carboxamide.

For three of the modified proteins, single labeling was confirmed by mass spectrometry, indicating that only one cysteine is modified. All the proteins showed a fluorescence intensity decrease on addition of ADP.

In order to create new sites for specific labeling, first the exposed cysteine was mutated to alanine and then new cysteine residues were introduced by site-directed mutagenesis. In the work below, all ParM proteins include this C287A mutation. Two different strategies are demonstrated to generate a ParM variant with a fluorescence increase upon ADP binding.

The first approach relies on single cysteine mutants for attachment of single fluorophores, which experience a change in environment when the target molecule binds. Following examination of the structure of ParM and the nucleotide induced conformation change, six different mutant ParM proteins were prepared that each had a single reactive cysteine residue. These were positioned on the surface of subdomains IA, IB and IIB, where the two lobes approach upon ADP-triggered cleft closure. The mutants were labeled with different probes and fluorescence spectra were recorded in the absence and presence of ADP. Only ParM (I27C) responded to ADP with an increase in fluorescence intensity, whereas all other mutants showed a signal decrease (Table 1). The largest response was obtained with the coumarin derivative, MDCC, which gave a three-fold fluorescence increase (FIG. 1). This adduct, MDCC-ParM (I27C/C287A), was chosen for further study and development.

The second labeling approach takes advantage of the large difference in rhodamine fluorescence depending on whether the fluorophore is in a monomeric or dimeric state, as outlined in the Introduction. To implement this strategy with ParM, two double cysteine mutants were generated, D63C/D224C and D63C/K216C. D224 and K216 are located on helix 8 in subdomain IIB. D63 is situated in a loop on the opposing subdomain, which moves away from helix 8 upon ADP bind-

TABLE 1

Fluorescence changes for a variety of ParM mutants labeled with different fluorophores.

|  | WT | I27C | D58C | D63C | S204C | T215C | K216C | D224C | D63C/K216C | D63C/D224C |
|---|---|---|---|---|---|---|---|---|---|---|
| MDCC | 0.27 | 3.0 | 0.82 | 0.48 | 0.68 | 0.74 | 0.67 | 0.69 | | |
| MPrCC | | 1.1 | | | | 0.78 | | 0.75 | | |
| IDCC | 0.34 | 1.5 | 0.93 | 0.53 | 0.80 | 0.74 | 0.76 | 0.67 | | |
| CPM | | 0.62 | | | 0.62 | 0.76 | | 0.71 | | |
| 5-IATR | 0.74 | 1.3 | 0.83 | 0.80 | | | 0.80 | | 3.2 | 4.4 |
| 6-IATR | 0.70 | | | | | | | | 1.4 | 9.7 |
| Alexa 488 | | 0.78 | | | | | | | | |
| Cy3 | | 1.2 | | | | | | | | |
| Cy3b | | 0.83 | | | | | | | | |
| MIANS | 0.50 | 0.72 | | | 0.91 | | | | | |
| Acrylodan | 0.59 | | | | | | | | | |

The fluorescence change is expressed as ratio of the intensity in presence of 1 mM ADP to that in the absence of ADP.

Figure 2B:
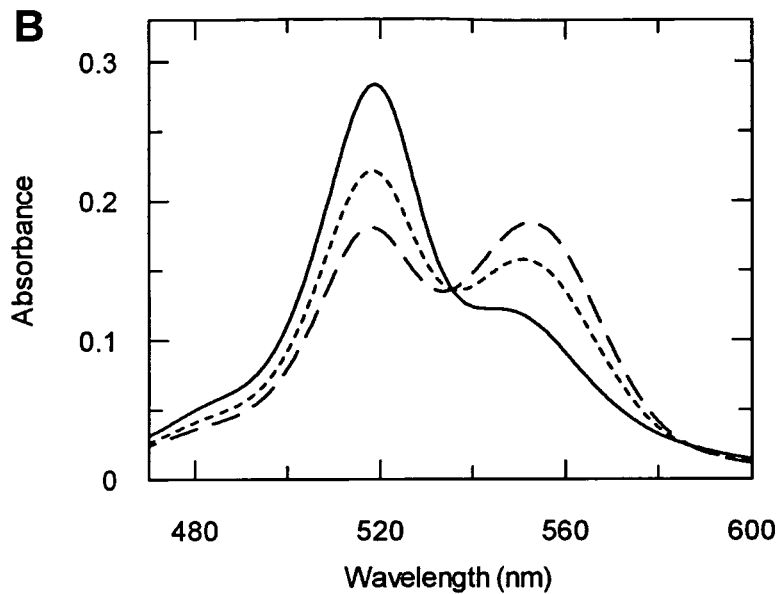

Fluorescent labels were: Acrylodan: 6-acryloyl-2-dimethylaminonaphthalene; Alexa488, AlexaFluor-488-maleimide; CPM, 7-diethylamino-3-[4'-(1-maleimidyl)phenyl]-4-methylcoumarin; Cy3, Cy3-maleimide; Cy3B, Cy3B-maleimide; 5-IATR and 6-IATR, 5- and 6-iodoacetamidotetramethylrhodamine; IDCC, N-[2-(iodoacetamido)ethyl]-7-diethylaminocoumarin-3-carboxamide); MDCC, N-[2-(1-maleimidyl)ethyl]-7-diethylamiing. Consideration of distances between labeling sites was based on the structure of the rhodamine stacking and previous work with rhodamine labeling of phosphate binding protein (30). In the nucleotide-free conformation a rhodamine pair attached to these positions should potentially be able to stack and this interaction may be disrupted when ADP binding induces domain movement. Test labeling of the two double mutants was done with two different rhodamine isomers, 5-IATR and 6-IATR, and the fluorescence response to ADP binding was investigated (Table 1). The labeling stoichiometry is 2:1 as confirmed by mass spectrometry. All four combinations showed an increase in fluorescence as expected for the disruption of rhodamine dimers. Three combinations revealed a relative change>3-fold. The largest signal change (10-fold) was observed with 6-IATR and D63C/D224C mutations (FIG. 2). FIG. 2b shows the absorbance spectra of this labeled ParM variant in the absence and presence of ADP. The spectrum of 6-ATR ParM is indicative of rhodamine dimers with maximum absorbance at 519 nm and a shoulder around 550 nm. Binding of ADP causes an absorbance decrease at 519 nm and a concomitant increase in absorbance at 553 nm.

Example 2

ADP Binding Affinity

The sensitivity of ADP detection depends in part on the size of the fluorescence change, but more importantly on the ADP affinity. To determine the ADP dissociation constants, the four ParM variants with 3-fold or higher signal change were titrated with ADP (FIG. 3). The highest affinity was found for MDCC-ParM (I27C) ($K_d$=0.31 μM), which allows detection of submicromolar concentrations of ADP. In contrast, the dissociation constants of the rhodamine-labeled variants 5-ATR-ParM (D63C/K216C), 5-ATR- and 6-ATR-ParM (D63C/D224C) are much higher (4.2 μM, 80 μM and 141 μM, respectively) and thus the sensitivity (in terms of ADP affinity) is reduced by the presence of the two rhodamines. Of course, such rhodamine embodiments are still useful since the attachment of two fluorophores may be desirable in some applications, and the presence of two fluorophores may contribute a stronger signal despite the lower ADP affinity as noted above.

Based on the advantageously lower ADP affinity, further development is focussed on the MDCC-ParM (I27C) to achieve a tight binding variant.

Example 3

Active Site Mutations to Enhance Selectivity for ADP

A challenge in the development of any ADP-specific biosensor that is based on binding, is to achieve good discrimination against ATP. Titration of MDCC-ParM (I27C) with ATP yielded a dissociation constant of 18.7 μM, 60-fold higher than the dissociation constant of the ADP complex. The size of the fluorescence change was similar to that obtained with ADP. This weaker binding result was surprising, since wild-type ParM binds the fluorescent analogue ethenoATP with 60-fold higher affinity than ethenoADP. However, the ATP affinity of MDCC-ParM is still too high for some applications: at 18 μM ATP as substrate, the fluorescence would be already half the maximum obtainable.

By examination of the active site structure; a mutation strategy that might weaken ATP binding without changing the ADP affinity was designed. First, the ParM expression plasmid was modified so that it was expressed with a C-terminal hexahistidine tag to simplify purification. On the background of ParM (His$_6$/I27C), ten different active site mutants were generated (Table 2).

TABLE 2

Fluorescence change and affinities of ADP and ATP of various MDCC-ParM mutants.

| ParM mutation in addition to I27C | ADP | | ATP | | $K_d$ ratio ATP/ADP |
|---|---|---|---|---|---|
| | $F_{+ADP}/F_{-ADP}$ | $K_d$ (μM) | $F_{+ATP}/F_{-ATP}$ | $K_d$ (μM) | |
| E148R | <1.1 | n.d. | <1.1 | n.d. | |
| T175H | 3.2 | 0.40 | 3.9 | 0.16 | 0.4 |
| T175F | 2.5 | 4.7 | 2.5 | 137 | 29 |
| S9A | 3.1 | 2.5 | 2.9 | 98 | 39 |
| S9Q | 3.2 | 1.66 | 2.8 | 66 | 40 |
| (I27C only) | 3.0 | 0.31 | 3.1 | 18.7 | 60 |
| T174A | 2.9 | 0.39 | 3.1 | 64 | 164 |
| T175A | 3.3 | 0.37 | 3.3 | 62 | 168 |
| T175N | 3.4 | 0.60 | 3.2 | 184 | 307 |
| T174A T175A | 3.3 | 0.33 | 3.2 | 107 | 324 |
| T175L | 1.9 | 1.57 | 2.3 | 507 | 324 |
| T174A T175N | 3.4 | 0.57 | 3.1 | 208 | 365 |

Data were obtained from fluorescence titrations at 20° C. as described in FIG. 3. ATP titrations were performed with highly purified ATP, containing only 0.03% ADP. I27C only denotes MDCC-ParM (I27C/C287A). All other mutants are based on MDCC-ParM (His$_6$/I27C/C287A) with the additional mutations shown in the table.

Firstly, the side chains of S9, T174 and T175 form hydrogen bonds to the ☐-phosphate in the ParM.GMPPNP structure (21), but none of them is within hydrogen bonding distance to the diphosphate (15). Removing their hydroxyl groups by mutation to alanine may therefore selectively weaken triphosphate binding.

Secondly, blocking the ☐-phosphate binding site sterically by introducing more bulky amino acids at position 9, 148 and 175 was investigated.

The ParM mutants were labelled with MDCC and analyzed for ADP and ATP binding affinity (Table 2 and FIG. 4). The four best mutants in terms of ADP selectivity are T175N, T175L, T174A/T175A and T174A/T175N, binding ATP>300-fold weaker than ADP. The ratio of the dissociation constants for ATP and ADP is similar for these proteins, but they differ in the absolute affinities. While T174A/T175A retains the ADP affinity of the original ParM I27C mutant, the $K_d$ values are increased by the other three mutations T175N, T174A/T175N and T175L.

Example 4

Kinetics of ADP Binding

To assess the suitability of MDCC-ParM for real-time measurements, the dynamics of ADP binding was investigated for MDCC-ParM (I27C) and four active-site mutants with the strongest discrimination against ATP (see example 3—enhanced selectivity substitutions). For this example, these enhanced selectivity substitutions are used in combination with the fluorphore attachment substitution I27C i.e. the polypeptide of this example comprises I27C as well as the particular enhanced selectivity substitutions discussed.

Figure 5B:
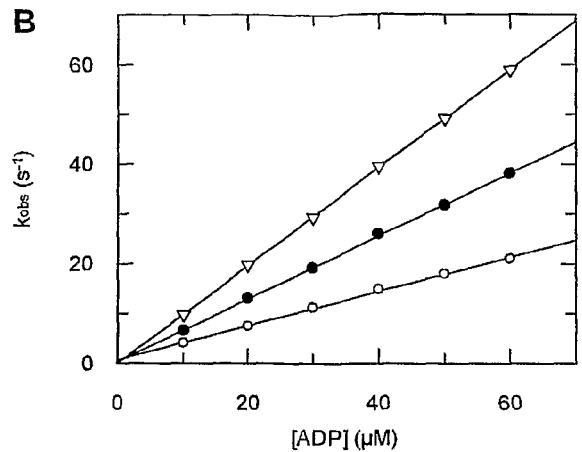
Figure 5C:
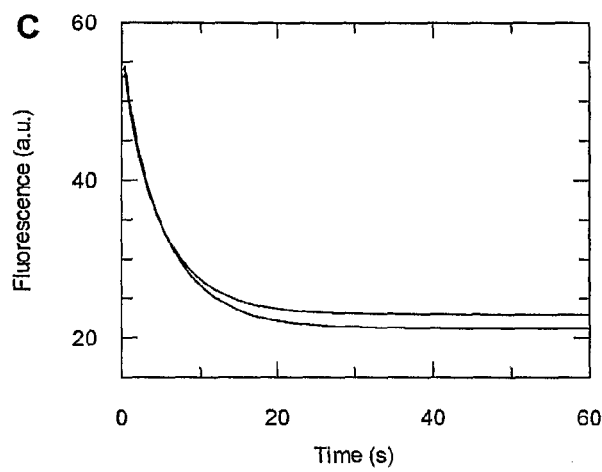

Association kinetics were measured under pseudo-first-order conditions with an excess of ADP. A single exponential increase in fluorescence was observed after mixing ParM and ADP in the stopped-flow apparatus (FIG. 5). The observed rate constants show a linear dependence on ADP concentrations up to at least 60 μM ADP, from which the association rate constants were extracted (FIG. 5b). Since the dissociation rate constants are small and values cannot be determined accurately from the intercept, they were measured more directly in displacement experiments (FIG. 5c). The kinetic constants for ADP binding to the different ParM mutants as well as well as the equilibrium dissociation constants deduced are summarized in Table 3.

TABLE 3

Kinetic parameters for association of ADP with various MDCC-ParM mutants.

| ParM mutation in addition to I27C | $k_{on}$ (µM$^{-1}$s$^{-1}$) | $k_{off}$ (s$^{-1}$) | $K_d$ (µM) |
|---|---|---|---|
| (I27C only) | 0.98 | 0.22 | 0.22 |
| T174A T175A | 0.98 | 0.22 | 0.22 |
| T175L | 0.34 | 0.28 | 0.81 |
| T175N | 0.64 | 0.27 | 0.42 |
| T174A T175N | 0.63 | 0.19 | 0.30 |

Association and dissociation rate constants ($k_{on}$ and $k_{off}$) were measured in stopped-flow experiments as shown in FIG. 5. The equilibrium dissociation constant $K_d$ was calculated as $k_{off}/k_{on}$.

The $K_d$ values determined from the kinetic experiments are slightly lower than those from equilibrium titrations (Table 2) but the order in binding affinity of the different mutants is the same. The difference in ADP affinities is mainly caused by different association rate constants, which range from 0.34 to 0.98 µM$^{-1}$ s$^{-1}$, while the dissociation rate constants are rather similar.

MDCC-ParM (His$_6$/I27C/T174A/T175N/C287A) may be the best variant, since it shows a slightly larger discrimination against ATP than the other mutants, and has a high fluorescence change (FIG. 1). Therefore this variant is a most preferred ADP binding molecule of the invention, hereafter referred to as MDCC-ParM. For this mutant the kinetics of ADP binding was also measured at higher ADP concentrations. The linearity of the observed rate constant with ADP concentration extends to ~200 µM ADP, where it is 120 s$^{-1}$.

Example 5

Linearity of the Fluorescence Response

Active site titrations with ADP were performed at 20 µM MDCC-ParM, 35-fold above the dissociation constant (FIG. 6a). A four-fold fluorescence change was obtained at saturation. The break point of this titration gives a value of 19.3 µM for the concentration of active sites, which is in very good agreement with the ParM concentration, determined from absorbance spectra.

In many applications of the sensor, ADP will be measured as a product from ATP substrate, either for an ATPase or kinase and so ATP will be present in the assay solutions. Therefore, the fluorescence response to ADP was investigated in the presence of ATP (FIG. 6b) in order to demonstrate the applicability of the invention in this context.

The fluorescence intensity of MDCC-ParM was measured at a constant nucleotide concentration of 10 µM (ATP+ADP), while the ADP content was increased. Importantly, a linear increase in fluorescence was observed as in the absence of ATP. The slope is ~7% lower due to a higher starting fluorescence, which is expected from some ATP binding to the sensor. However, the ATP solution used contained 0.6% ADP, which also contributes to a higher starting level.

Thus it is demonstrated that the invention provides a robust ADP sensor molecule which performs both in the presence and absence of ATP.

Example 6

ATP Hydrolysis Assay

The invention finds application as a reporter for assays having ADP as a substrate or product. By measuring ADP concentrations according to the present invention, the assay(s) may be advantageously monitored. In this example, the assay comprises steady state ATP hydrolysis by PcrA helicase.

PcrA is a DNA helicase from *Bacillus stearothermophilus* involved in plasmid replication. It unwinds double stranded DNA by translocating on one strand in the 3'- to 5'-direction. PcrA also moves rapidly along short single stranded oligonucleotides hydrolyzing one ATP molecule per base pair unwound (31). In a steady-state assay the hydrolysis rate of PcrA is measured in the presence of a short single-stranded oligonucleotide, d116, using MDCC-ParM. The kinetics of ADP generation are monitored at two different PcrA concentrations (1 and 2 nM) and in the absence of PcrA as a control (FIG. 7). In this assay, the response is linear only initially, because of ATP depletion near its $K_m$ value. ADP concentrations were calculated from the fluorescence signal using a calibration with constant nucleotide concentration ([ATP]+[ADP]) and increasing ADP content as shown in FIG. 6. The initial rates were determined by linear regression to the data points where less than 10% of the ATP was turned over. In the absence of PcrA a very slow fluorescence increase was observed, 16-fold slower than in presence of 1 nM PcrA, which might reflect slow ATP hydrolysis catalyzed by ParM. The initial rates were therefore corrected by subtracting the background rate. The steady state hydrolysis activity of PcrA obtained in these measurements is 6.8 s$^{-1}$. For comparison, the same experiment was carried out using the well characterized phosphate biosensor MDCC-PBP. The hydrolysis activity of 7.2 s$^{-1}$ confirms the result obtained with the ADP sensor of the invention.

Example 7

Kinase Assay

Kinases are key targets in drug discovery. Kinase action involves generation of ADP as ATP is used during phosphorylation of the substrate. ADP is therefore an indicator of kinase activity in this type of assay.

Application of the invention to readout of kinase assays is demonstrated. In this example, steady state activity of the protein kinase PknB is used to illustrate this type of application of the invention.

*Mycobacterium tuberculosis* contains eleven different Ser/Thr kinases (32). Three of them, including PknB, are essential for mycobacterial growth and therefore have received some interest as possible drug targets (33-35). Regulation of cell growth and division by these kinases is not well understood. Physiological substrates of PknB have been identified only recently, including the FHA (Forkhead associated) domain found in protein Rv1827, also called GarA (36). The kinetics of Rv1827 phosphorylation by the PknB kinase domain has been measured previously using radiolabeled ATP, which showed that phosphorylation occurs at a rate of 9.6 min$^{-1}$ at 30° C. (36). However, the $K_M$-value for this substrate has not been determined. We have investigated this phosphorylation reaction using MDCC-ParM, providing a considerably faster way of assaying kinase activity. Steady-state kinetics of ADP release during phosphorylation was measured at constant ATP and increasing concentrations of the substrate Rv1827 (FIG. 7). The calibration was performed analogous to the PcrA assay described above. The dependence of the initial rate on Rv1827 concentration was analyzed using the Michaelis-Menten equation, yielding a $K_M$ value of 22 µM and a maximal rate of 1.2 µM min$^{-1}$. This maximal rate may be an underestimate because we have not determined the $K_M$-value for ATP and so the ATP concentration used may not be saturating. Nevertheless, the specific activity of the PknB kinase domain was calculated for 40 µM ATP as 5.9 s$^{-1}$, very similar to the published result.

These data validate the application of ADP binding molecules according to the present invention as sensor proteins to report on kinase assays. Thus the invention provides simple fluorimetric assay systems for monitoring kinase assays in real time whilst advantageously avoiding radiolabelling and other expensive, hazardous or time consuming techniques.

Example 8

Characterisation and Application of Coumarin Biosensor

In this example, the coumarin version, MDCC ParM is used. Figures referred to in this example show data with K33A mutation i.e. relate to characterisation of a preferred coumarin coupled ADP sensor, MDCC-ParM (His6/I27C/K33A/T174A/T175N/C287A).

In particular we show nucleotide affinity, kinetics, filament formation assay, and ATPase activity.

In addition we demonstrate application of the invention in real-time assays using the above sensor, including DNA helicase PcrA; protein kinase PknB; and SufBC, an ATPase involved in Fe—S cluster assembly.

The MDCC-ParM sensor of this example is MDCC-ParM (His6/I27C/K33A/T174A/T175N/C287A), the exemplary sequence is given as SEQ ID NO:5. The same method of purification and labelling described for the MDCC-ParM variant in the earlier examples also applies to this K33A sensor variant unless otherwise mentioned below.

Filament Formation

MDCC-ParM (His6/I27C/T174A/T175N/C287A) was analysed for filament formation and indeed was shown to polymerise, albeit slowly and at high ATP concentrations. Therefore an additional mutation was introduced, K33A, which completely abolished filament formation under all conditions tested (max. 120 µM ParM, 4 mM ATP, 4 hours). The preferred sensor is therefore MDCC-ParM (His6/I27C/K33A/T174A/T175N/C287A).

Characterisation of the K33A coumarin sensor, MDCC-ParM (His6/I27C/K33A/T174A/T175N/C287A), showed similar ADP affinity (Kd=0.46 µM), similar discrimination against ATP (Kd=212 µM) and similar ADP binding kinetics (kon=0.65 µM-1 s-1, koff=0.19 s-1) compared to the version in earlier examples (without the K33A mutation).

We also demonstrate the following applications of the biosensor of the invention, using the K33A variant MDCC-ParM (His6/I27C/K33A/T174A/T175N/C287A) in this example, in real-time measurements of ADP generation by ATPases or kinases: First, steady-state assay on the DNA helicase PcrA, determination of the KM value for ATP. Second, steady-state assay on the protein kinase PknB, determination of the KM values for ATP and the protein substrate Rv1827. Third, transient kinetics of ADP release in the ATPase cycle of SufBC, an ATPase involved in Fe—S cluster assembly.

Overview

Nearly every cellular process requires the presence of ATP. This is reflected in the vast number of enzymes like kinases or ATP hydrolases, which both cleave the terminal phosphate from ATP, thereby releasing ADP. Despite the fact that ATP hydrolysis is one of the most fundamental reactions in biological systems there are only few methods available for direct measurements of enzymatic driven ATP conversion. Here we describe the development of a reagentless biosensor for ADP, the common product of all ATPases and kinases, that allows the real-time detection of ADP, produced enzymatically. The biosensor is derived from a bacterial actin homologue, ParM, as protein framework. A single fluorophore (a diethylaminocoumarin), attached to ParM at the edge of the nucleotide binding site, couples ADP binding to a >3.5-fold increase in fluorescence intensity. The labeled ParM variant has high affinity for ADP (0.46 µM) and a fast signal response, controlled by the rate of ADP binding to the sensor (0.65 µM$^{-1}$ s$^{-1}$). Amino acids in the active site were mutated to reduce ATP affinity and achieve >400-fold discrimination against triphosphate binding. A further mutation (at K33) ensures that the sensor did not form filaments and, as a consequence, has extremely low ATPase activity. The broad applicability of MDCC-ParM as a sensitive probe for ADP is demonstrated in real-time kinetic assays on two different ATPases and a protein kinase.

Labeling of ParM with MDCC

Labeling of the sensor variant ParM (His$_6$/I27C/K33A/T174A/T175N/C287A) was typically carried out on a scale of ~100 mg protein. Labeling reactions contained 150 µM ParM and 250 µM MDCC in 30 mM Tris.HCl pH 7.5, 25 mM KCl. The reaction mixture was incubated for 35 min, end-over-end mixing at 22° C. 2 mM sodium 2-mercaptoethane-sulfonate was added and incubation was continued for 15 min. The solution was filtered through a 0.2 µm Acrodisc filter (Pall Corporation) and loaded onto a 5 ml HiTrap Q column (GE Healthcare) equilibrated with 30 mM Tris.HCl pH 7.5, 25 mM KCl. The column was washed with the same buffer until the 280 nm absorbance reached baseline. A 200 mL linear gradient of 25-400 mM KCl was applied. The main peak of labeled ParM, eluting at ~130 mM KCl, was pooled and MDCC-ParM was concentrated as described above. The concentration of labeled ParM was determined using the extinction coefficients for MDCC coupled to dithiothreitol (7), $\epsilon_{430}$=46800 M$^{-1}$ cm$^{-1}$ and $\epsilon_{280}$=7470 M$^{-1}$ cm$^{-1}$, and the extinction coefficient of ParM, given above. The identity of the labeled ParM variant was confirmed by electrospray-ionization mass spectrometry. The measured molecular weight was 37,214.8 Da conforming to the theoretical mass of the ParM construct labeled with a single MDCC, 37,214.5 Da. (The only difference to the previous examples is that 30 mM Tris+25 mM KCl instead of only Tris is used for the labelling and Q column.)

Assays and Applications

Steady-state activity measurements of PcrA helicase and PknB kinase were performed with the ADP biosensor MDCC-ParM (His$_6$/I27C/K33A/T174A/T175N/C287A). The helicase assay was carried out in 50 mM Tris.HCl pH 7.5, 150 mM NaCl, 3 mM MgCl$_2$; for the kinase assay 30 mM Tris.HCl pH 7.5, 150 mM NaCl, 3 mM MgCl$_2$ and 2 mM DTT was used. MDCC fluorescence was measured at excitation and emission wavelengths of 431 nm and 474 nm, respectively. The concentrations used in the experiments are given in the respective figure legends. For calibration of the sensor response, MDCC-ParM, at the concentration used in the assay, was titrated with ADP and the fluorescence was recorded. To account for the different fluorescence responses when ATP is present, these titrations were carried out at a series of different, initial ATP concentrations (see FIG. 8D). Thereby, the total nucleotide concentration, ATP+ADP, was held constant during the titrations and only the ADP content was changed. This was achieved by incubating MDCC-ParM plus a particular ATP concentration in the cuvette and then titrating with an ADP solution of the same concentration as ATP in the cuvette and also containing MDCC-ParM at the cuvette concentration. By linear regression a gradient was obtained for each initial ATP concentration, corresponding to the change in fluorescence intensity per micromolar ADP. Instead of performing such a calibration for each initial ATP concentration used in the helicase or kinase assay, the titrations were performed at only four different total nucleotide concentrations. The calibrations for the other concentrations were then obtained by interpolation. Titrations were measured at 3, 6, 10 and 15 μM initial ATP for the PcrA assay and 10, 20, 30 and 40 μM for the PknB assay, as well as in the absence of ATP. The gradients obtained in these titrations were plotted versus the initial ATP concentration. For each initial ATP concentration a gradient for calibration was then calculated by linear interpolation and these were used to calculate the ADP concentrations from the fluorescence signal.

Phosphate and ADP release kinetics during a single turnover of ATP hydrolysis by SufBC from *Thermotoga maritima* were measured with the phosphate biosensor MDCC-PBP (19) and the ADP sensor MDCC-ParM, respectively. Measurements were carried out in 50 mM Tris.HCl pH 7.5, 100 mM KCl, 5 mM MgCl$_2$ and 2 mM DTT. A solution of 13 μM SufBC containing the respective biosensor (20 μM MDCC-PBP or 80 μM MDCC-ParM) was rapidly mixed with a 4 μM ATP solution. P$_i$ release data were analyzed by single exponential curve fitting using Grafit software. ADP release kinetics could be described by assuming two successive irreversible steps, where ADP is released in the second step. Curve fits were carried out with Grafit, using the following equation:

$$F=A(1+(k_2/(k_1-k_2))\exp(-k_1t)+(k_1/(k_2-k_1))\exp(k_2t)+F_0 \qquad \text{Eq. 2}$$

where $F_0$ is the fluorescence at time point zero, A is the total fluorescence change and $k_1$ and $k_2$ are the rate constants of the two first order reactions. To measure ADP dissociation kinetics from the SufBC complex, 13 μM SufBC and 4 μM ADP was preincubated in one syringe before rapidly mixing with 80 μM or 160 μM MDCC-ParM. Data were analyzed by single exponential curve fitting using the HiTech software. The rate constant was only 10% different between the measurements with 80 and 160 μM MDCC-ParM.

Mutations to Inhibit Filament Formation

Wild-type ParM forms actin-like filaments, which are essential for its function in plasmid segregation (21) but could disturb the sensor function of ParM. Filament formation may interfere with the fluorescence signal and the ATPase activity of ParM is strongly enhanced in the filament (20,21). The polymerization of MDCC-ParM (His$_6$/I27C/T174A/T175N/C287A) was investigated using light scattering. At 10-40 μM, this variant formed filaments when ATP was added but not with ADP or in the absence of nucleotide (FIG. 13A). The nucleation and polymerization kinetics were much slower than for wild-type ParM, but the critical concentration, 2.5 μM, was very similar to wild-type ParM (20). Therefore, further mutations were introduced to block filament formation. Among others the two point mutations K33A and R34A have been shown to inhibit filament formation (16) and these residues participate in interactions between protomers in a model of the ParM filament (15). We have introduced each mutation into ParM (His$_6$/I27C/T174A/T175N/C287A) and analysed the labeled proteins for polymerization. Light scattering assays showed that the K33A mutation blocks filament formation more efficiently: no increase in light scattering was detected over a period of four hours, even at very high (120 μM) concentration of the sensor (FIG. 13B). Thus, the ParM variant containing the K33A mutation, MDCC-ParM (His$_6$/I27C/K33A/T174A/T175N/C287A), was chosen as the preferred ADP biosensor, hereafter referred to as MDCC-ParM.

As mentioned above, filament formation is related to an acceleration of ATP hydrolysis and therefore the K33A mutation is expected to decrease ATPase activity. The ATPase rate of MDCC-ParM was measured, using a phosphate biosensor, Rhodamine-PBP (22). ATP hydrolysis was very slow with a rate constant<0.001 min$^d$, which is >10-fold lower than MDCC-ParM without the K33A mutation. Thus, the K33A mutation not only blocks filament formation, but thereby also inhibits ATPase activity.

Characterization of the Preferred ADP Sensor, MDCC-ParM

Titrations of MDCC-ParM with ADP and ATP showed that the K33A mutation did not alter ADP affinity and discrimination against ATP (FIG. 8B and Table Z).

TABLE Z

Dissociation constants and fluorescence changes for binding of ADP and ATP to MDCC-ParM mutants at different stages of the sensor development.

| | ADP | | ATP | | K$_d$ ratio |
|---|---|---|---|---|---|
| ParM mutant | F$_{+ADP}$/F$_{-ADP}$ | K$_d$ (μM) | F$_{+ATP}$/F$_{-ATP}$ | K$_d$ (μM) | ATP/ADP |
| I27C C287A | 3.0 | 0.31 | 3.1 | 18.7 | 60 |
| I27C T174A T175N C287A | 3.5 | 0.51 | 3.3 | 203 | 398 |
| I27C K33A T174A T175N C287A | 3.5 | 0.46 | 3.2 | 212 | 460 |

The fluorescence change upon ADP and ATP binding (F+/F−) and the dissociation constants (K$_d$) were obtained from fluorescence titrations at 20° C. in 30 mM Tris buffer pH 7.5, 25 mM KCl, 3 mM MgCl$_2$ and 5 μM BSA. ATP titrations were performed with highly purified ATP containing <0.1% ADP. All ParM variants exept the initial double mutant I27C C287A additionally contain a C-terminal His$_6$-tag. In four different batches of labeled ParM (His$_6$/I27C/K33A/T174A/T175N/C287A) the ADP affinity varied between 0.38 and 0.52 μM and the signal change was between 3.3 and 4.1-fold.

Thus, the preferred sensor retains submicromolar ADP sensitivity and high selectivity for the diphosphate. While all data described so far were obtained in buffer containing low salt concentration (25 mM KCl), the influence of physiological ionic strength was tested, using 150 mM KCl or NaCl (Table S3).

TABLE S3

ADP and ATP binding to the MDCC-ParM biosensor under different salt conditions.

| | ADP | | ATP | | K$_d$ ratio |
|---|---|---|---|---|---|
| Salt condition | F$_{+ADP}$/F$_{-ADP}$ | K$_d$ (μM) | F$_{+ATP}$/F$_{-ATP}$ | K$_d$ (μM) | ATP/ADP |
| no additional salt | 3.4 | 4.11 | 3.5 | 378 | 94 |
| 25 mM KCl | 3.5 | 0.46 | 3.2 | 212 | 460 |
| 150 mM KCl | 3.4 | 0.20 | 3.5 | 73 | 370 |
| 25 mM NaCl | 3.5 | 1.36 | 3.5 | 214 | 160 |
| 150 mM NaCl | 3.4 | 1.34 | 3.2 | 244 | 180 |

Dissociation constants (K$_d$) and fluorescence changes upon nucleotide binding (F$_+$/F$_-$) to the preferred biosensor, MDCC-ParM (His$_6$/I27C/K33A/T174A/T175N/C287A) were determined by fluorescence titrations as described. Titrations were carried out at 20° C. in 30 mM Tris•HCl pH 7.5, 3 mM MgCl$_2$, μM BSA plus the salt indicated.

The fluorescence response to ADP did not significantly vary but there were small changes (maximal threefold) in nucleotide affinity. However, the ADP affinity was significantly lower (4.1 μM) in the absence of KCl or NaCl (Table S3).

Accurate measurement of ADP concentrations using MDCC-ParM requires calibration of the fluorescence signal under the same conditions. Active site titrations of MDCC-ParM showed a linear fluorescence increase up to at least half saturation of the sensor (FIG. 8C). At 20 μM MDCC-ParM the fluorescence change is 3.8-fold and the concentration of active sites is 19.8 µM, in very good agreement with the concentration determined from its absorbance spectrum. In most applications of the sensor, ADP is likely to be measured as a product from ATP substrate, and so ATP will be present in the assay solutions. Therefore, calibration curves were determined in the presence of different ATP concentrations, but at constant total nucleotide concentration, ATP+ADP (FIG. 8D). A linear relationship between fluorescence intensity and ADP concentration was observed, but the slope decreased with increasing concentrations of ATP.

To assess the suitability of MDCC-ParM for real-time measurements, the kinetics of ADP binding and dissociation were investigated in stopped-flow experiments. A single exponential increase in fluorescence was observed after mixing MDCC-ParM and ADP (FIG. 9A). The observed rate constants showed a linear dependence on ADP concentrations, the slope gave the association rate constant, $0.65\ \mu M^{-1}\ s^{-1}$. This linear dependence indicates that the rate of the signal response is controlled by ADP binding and not by a conformational change. The dissociation rate constant was measured by displacement experiments starting from a complex of MDCC-ParM.ADP and trapping dissociated ADP with a large excess of unlabeled ParM (FIG. 9B). A value of $0.19\ s^{-1}$ was obtained, yielding the dissociation constant, 0.30 µM, in good agreement with data from equilibrium titrations (Table Z).

Prokaryotic and archeabacterial homologues of actin, including ParM, MreB, FtsA and Ta0583, show a rather low specificity for the base (23-25). In addition to adenine nucleotides, ParM has been reported to bind the guanine nucleotides GDP and GTP (15), but the binding affinity was not determined. Addition of GDP to MDCC-ParM resulted in only a small, 1.2-fold, increase in fluorescence. However, competitive titrations showed that GDP can displace ADP from MDCC-ParM and the dissociation constant for GDP, 4.4 µM, was only ten-fold higher than that for ADP. In conclusion, GDP binds to the sensor but does not induce a large change in MDCC fluorescence. GDP competes with ADP for the MDCC-ParM binding site and therefore its presence might interfere with ADP detection.

Competitive Titrations

Binding of GDP to the MDCC-ParM biosensor does not result in a large fluorescence change; therefore GDP affinity was determined by competitive titrations. These were measured at 20° C. using a Cary Eclipse spectrofluorimeter (Varian). Titrations were carried out in 30 mM Tris.HCl pH 7.5, 25 mM KCl, 3 mM MgCl$_2$ and 5 µM BSA. A mixture of 1 µM ADP and 0.1 µM MDCC-ParM was titrated with GDP solutions, containing the same concentration of ADP and MDCC-ParM. The displacement of ADP from MDCC-ParM by GDP was detected as a decrease in MDCC fluorescence, exciting at 431 nm and detecting fluorescence emission at 474 nm. Data were analyzed using the program Scientist (Micromath, Saint Louis, Mo.) as described (Alexandrov, K., Scheidig, A. J., and Goody, R. S. (2001) Fluorescence methods for monitoring interactions of rab proteins with nucleotides, rab escort protein, and geranylgeranyltransferase. In: Balch, W. E., Der, C. J., and Hall, A. (eds). *Methods Enzymol.*, Academic Press). In the competitive titration model, the $K_d$ value for ADP was fixed to the value determined by direct titration. Values for the dissociation constant of GDP binding and the fluorescence coefficients of MDCC-ParM alone and in complex with ADP were allowed to vary during the fitting procedure.

ATP Hydrolysis of MDCC-ParM

The rate of ATP hydrolysis by MDCC-labeled ParM variants was measured using the phosphate biosensor Rhodamine-PBP (Okoh, M. P., Hunter, J. L., Corrie, J. E. T., and Webb, M. R. (2006) *Biochemistry* 45, 14764-14771). 10 µM Rhodamine-PBP and 10 µM MDCC-ParM in 30 mM Tris buffer pH 7.5, 25 mM KCl, 3 mM MgCl$_2$ were pre-incubated at 20° C. for 3 min before 500 µM ATP was added. The time course of the reaction was measured by recording the fluorescence change of Rhodamine-PBP using a Cary Eclipse spectrofluorimeter (Varian). The fluorescence was excited at 553 nm and emission was detected at 578 nm. As a control, the experiment was repeated in the absence of MDCC-ParM. The fluorescence signal was calibrated by titrating Rhodamine-PBP with a phosphate standard solution. To determine the ATP hydrolysis rate of MDCC-ParM data were corrected by subtracting the control experiment in the absence of ParM.

Light Scattering Measurements

Polymerization kinetics of different ParM variants were measured by monitoring right angle light scattering at 340 nm in a Cary Eclipse spectrofluorimeter (Varian). ParM solutions were centrifuged in a TLA120.1 rotor (Beckman) at 100,000 rpm for 15 min prior to the scattering experiments. Solutions of ParM variants in 30 mM Tris.HCl pH 7.5, 25 mM KCl, 3 mM MgCl$_2$ were incubated in the cuvette at 20° C. for 5 min, before ATP, ADP or only buffer were added. Scattering intensities were corrected by subtracting the intensity measured before addition of nucleotide. To determine the critical concentration in presence of ATP, the maximal scattering intensities were plotted versus ParM concentration. Critical concentrations were obtained by linear extrapolation to zero scattering intensity.

(See also van den Ent, F., Moller-Jensen, J., Amos, L. A., Gerdes, K., and Lowe, J. (2002) *EMBO J.* 21, 6935-6943)

Steady-State Measurements of ATPase and Kinase Activity

A DNA helicase, PcrA, was used as an ATPase system to demonstrate application of MDCC-ParM in a real-time assay. PcrA, from *Bacillus stearothermophilus*, is involved in plasmid replication (26), and moves rapidly along short single-stranded oligonucleotides hydrolyzing one ATP per base translocated (27,28). In a steady-state assay, the hydrolysis rate of PcrA was measured in the presence of a short oligonucleotide (dT$_{20}$), using the MDCC-ParM biosensor. The kinetics of ADP generation was monitored at different ATP concentrations (FIG. 10). A set of calibration curves, which accounts for different fluorescence responses at different ATP concentrations, was used to calculate the ADP concentrations from the fluorescence signal. A plot of the initial rates versus ATP concentration gave $K_M$ as 1.6 µM and $k_{cat}$ as $13.7\ s^{-1}$ (FIG. 10). However, very similar results were obtained, when a single calibration was used for all the measurements at different ATP concentrations. In this case, the Michaelis-Menten constant is calculated as 1.4 µM (17% lower). Using the calibration at 15 µM total nucleotide concentration (maximal ATP concentration used), $k_{cat}$ was calculated as $14.0\ s^{-1}$ (2% higher). Alternatively, using the calibration in the absence of ATP yielded $k_{cat}$, $12.2\ s^{-1}$ (11% lower). For comparison, the experiment was repeated under the same conditions, but using the well characterized phosphate biosensor, MDCC-PBP (19). The parameters obtained are $K_M$, 1.7 µM and $k_{cat}$, $11.5\ s^{-1}$, supporting the results from the experiments using the ADP biosensor MDCC-ParM.

The protein kinase PknB from *Mycobacterium tuberculosis* was used as a second example of applying the ADP biosensor. PknB is a Ser/Thr kinase, essential for mycobacterial growth (29). A recently identified substrate of PknB is the FHA (Forkhead-associated) domain of Rv1827 (30), which is involved in regulation of glutamate metabolism (31). The steady-state kinetics of Rv1827 phosphorylation by the PknB kinase domain (PknB$^{1-279}$) was monitored by following the accompanying ADP generation with the biosensor MDCC-ParM (FIG. 11). The Michaelis-Menten parameters of both substrates were determined. For the protein substrate Rv1827 the values K$_M$, 20 µM, and k$_{cat}$ 4.7 min$^{-1}$ were obtained (FIG. 11A). The results from data at different initial ATP concentrations were K$_M$ 7.5 µM, and k$_{cat}$, 4.9 min$^{-1}$ (FIG. 11B).

P$_i$ and ADP Release During ATP Hydrolysis of SufBC

SufC is an ATPase involved in Fe—S cluster assembly under stress conditions (32,33). SufC and the associated protein SufB are found in bacteria, including human pathogens (e.g. *Yersinia pestis, Mycobacterium tuberculosis*), archea and the plastid organelle of algae and plants (32). The kinetic mechanism of the SufBC complex has been studied using fluorescent nucleotide analogues, mantATP and mantADP (34,35). Here, both the ADP biosensor (MDCC-ParM) and a P$_i$ biosensor (MDCC-PBP (19)), were used to study ADP and P$_i$ release during a single turnover of ATP hydrolysis by SufBC (FIG. 12). P$_i$ is released first at 0.070 s$^{-1}$, most likely controlled by ATP cleavage, as the rate constant is very similar to that of mantATP cleavage (34). The fluorescence trace of MDCC-ParM showed a marked lag phase, characterized by a very similar rate constant to P$_i$-release, 0.058 s$^{-1}$, before ADP dissociation occurs at 0.050 s$^{-1}$, comparable to the mantADP dissociation rate constant 0.038 s$^{-1}$ (34). Direct dissociation of ADP from the SufBC complex was also measured, by mixing the pre-incubated SufBC.ADP complex with MDCC-ParM. Fluorescence traces were single exponentials with a rate constant of 0.046 s$^{-1}$, conforming to the rate constant of ADP release during ATP hydrolysis. These measurements with unlabeled ATP and ADP confirm the studies using mant nucleotides (34), indicating that the mant group does not have a large effect on the SufBC/nucleotide interactions.

Example 9

Characterisation and Application of Rhodamine Biosensor

The preferred rhodamine version of the biosensor is characterised.

Suitably this biosensor comprises a C-terminal hexahistidine-tag for purification.

Suitably this biosensor comprises mutations to suppress ATP binding: T174A T175N Suitably this biosensor comprises a mutation to inhibit filament formation: K33A Particularly suitable versions or variants include: ParM (His6/D63C/T174A/T175N/D224C/C287A) with and without K33A mutation; each such molecule labelled with 5-IATR or 6-IATR (i.e. four variants). We have taken the variant, 5-ATR-ParM (His6/D63C/T174A/T175N/D224C/C287A), as the preferred example and demonstrate this in an assay of hexokinase.

Characterisation of these variants including affinities, kinetics, filament formation assay, real-time assays with 5-ATR-ParM (His6/D63C/T174A/T175N/D224C/C287A) in the context of hexokinase are each presented below.

A C-terminal hexahistidine tag for purification by Ni-chelate chromatography was introduced into the two preferred ParM variants for rhodamine labeling, yielding ParM (His6/D63C/D224C/C287A) and ParM (His6/D63C/K216C/C287A).

Different combinations of active site mutations were added to the new constructs in order to increase selectivity for ADP versus ATP. These were (T174A/T175A) or (T174A/T175N) or (T174A/T175L), which have been shown to improve discrimination against ATP in the MDCC-labeled ParM variant (see above). The best version in terms of signal change and ADP selectivity was ParM (His6/D63C/T174A/T175N/D224C/C287A) labeled either with 5-IATR or with 6-IATR.

Filament formation was analysed for 5-ATR and 6-ATR-ParM (His6/D63C/T174A/T175N/D224C/C287A). Both were shown to form filaments but since the rhodamine-ParM sensors are likely to be used below the critical concentration this is unlikely to present any problem. Nevertheless, the K33A mutation, which efficiently blocks filament formation in the coumarin-labelled sensor variant was also introduced into the construct for rhodamine labeling to yield ParM (His6/K33A/D63C/T174A/T175N/D224C/C287A). The mutation completely abolished filament formation under the conditions tested.

Characterisation of 5-ATR and 6-ATR-ParM (His6/D63C/T174A/T175N/D224C/C287A) with and without K33A mutation is presented. The ADP and ATP affinities were measured for all four ParM variants (see table Y below). The ADP dissociation constants are in the range of 30-100 µM, where the mutants containing K33A have slightly higher affinity. ATP binds much weaker in all cases with a dissociation constant >5 mM. All four variants are also similar in the ADP binding kinetics (see table Y). However, while the maximal signal change upon ADP binding is 20-fold increase for the ParM variants without K33A mutation (both 5- and 6-IATR labeled), the fluorescence change was lower (max. 12-fold) for the variants containing K33A. Therefore, the ParM variant without K33A may be the preferred rhodamine labelled biosensor, whilst retaining the option of including K33A if desired, for example in case high concentrations of the sensor have to be used.

As an application of the rhodamine biosensor, 5-ATR-ParM (His6/D63C/T174A/T175N/D224C/C287A) has been used to measure the steady-state kinetics of yeast hexokinase. The KM values for D-glucose and ATP were determined.

By applying the two-rhodamine strategy to ParM, we have developed a new ADP biosensor variant with different characteristics to MDCC-ParM. The doubly rhodamine-labeled ParM variants binds ADP with relatively weak affinity (dissociation constant 30-100 µM) but responds to ADP binding with a very large, up to 20-fold, signal change. Both the active site mutations and the polymerization mutation described for MDCC-ParM also worked for the rhodamine-labeled version, weakening ATP binding affinity to >5 mM and abolishing filament formation. These rhodamine-based ADP biosensors extend the application range of ParM-based sensors towards measurements of high K$_M$ values and might be better suited for high throughput screening assays.

Labeling of ParM Mutants with 5- and 6-IATR

For double rhodamine-labeling of ParM mutants 100 µM ParM and 400 µM 5- or 6-ATR in 30 mM Tris HCl pH 7.5, 25 mM KCl (degassed) were incubated at 22° C., end-over-end stirring for 90 min. 2 mM sodium 2-mercaptoethanesulfonate was added and stirring was continued for another 15 min. Reaction mixtures were centrifuged (14.000 g, 10 min, 4° C.) and the supernatant was filtered through a 0.2 µm syringe filter (Acrodisc, Pall Corporation). Excess fluorophore and sodium 2-mercaptoethanesulfonate were removed on a PD10 column (GE Healthcare) using the same buffer as for labeling. The eluate was loaded on a HiTrap Q HP column (GE Healthcare) equilibrated with labeling buffer. The column was washed with the same buffer and the labeled ParM was eluted by applying a linear gradient of 25-200 mM KCl over 20 column volumes. Fractions were analyzed for the fluorescence change upon ADP addition ($\lambda_{ex}$=553 nm, $\lambda_{em}$=578 nm). Fractions showing the highest signal change were pooled and the labeled protein was concentrated in an Amicon Ultra centrifugal filter device (Millipore corporation, USA) to ~10 mg/ml. Aliquots were shock-frozen in liquid nitrogen and stored at −80° C. Double labeling was confirmed by electrospray-ionization mass spectrometry. The measured masses differed by less than 0.5 Da from the theoretical values for the doubly labeled proteins. Concentration of doubly rhodamine-labeled ParM mutants were determined from the absorbance spectra using the extinction coefficient of a small molecule thiol adduct of 6-IATR at its isosbestic point, $\epsilon_{528}$=52.000 M$^{-1}$ cm$^{-1}$ (18).

Fluorescence Measurements

Fluorescence spectra and titrations were measured in a Cary Eclipse spectrofluorimeter (Varian). Excitation and emission spectra were recorded with 5 nm slit width at emission and excitation wavelength of 576 nm and 553 nm, respectively. In titration experiments rhodamine fluorescence was measured at the same excitation/emission wavelength. Titration data were analyzed with a quadratic binding curve using the program Grafit 5.0 (7).

Stopped-flow experiments were performed using a HiTech SF61 DX2 instrument equipped with a Xe/Hg lamp (TgK Scientific, U.K.). Association kinetics of rhodamine-labeled ParM and ADP was measured under pseudo-first order conditions by mixing 0.2 µM labeled ParM with increasing concentrations of ADP. Rhodamine fluorescence was excited at 553 nm and fluorescence emission was detected after filtering scattered light through a 570 nm cut-off filter. Data were analyzed by single exponential curve fitting using the HiTech software.

All fluorescence measurements were carried out in 30 mM Tris.HCl pH 7.5, 25 mM KCl, 3 mM MgCl$_2$ and 5 µM BSA at 20° C.

Steady-State Assays of Hexokinase Activity

Michaelis-Menten kinetics of phosphorylation of D(+)-glucose by hexokinase from *S. cerevisiae* (Sigma-Aldrich) were monitored with the ADP biosensor 5-ATR-ParM (His$_6$/D63C/T174A/T175N/D224C/C287A) using a Cary Eclipse spectrofluorimeter (Varian). Measurements were carried out in 50 mM Tris.HCl pH 7.5, 25 mM KCl, 10 mM MgCl$_2$ and 5 µM BSA at 20° C. Reactions were set up with 0.5 µM 5-ATR-ParM, 0.02 unit ml$^{-1}$ hexokinase (1.3 nM monomers) and at constant 1 mM ATP and varying concentrations of glucose (20-2000 µM) or at constant 2 mM glucose and increasing ATP concentrations. The reaction was started by the addition of hexokinase. Rhodamine fluorescence was excited at 553 nm and emission was detected at 578 nm. For calibration of the fluorescence signal 0.5 µM 5-ATR-ParM was titrated with ADP in the presence of 1 mM ATP (maximal concentration used). In the range of 0-30 µM ADP the data can be approximated by a linear dependence (FIG. 18A) and the slope from a linear regression analysis of these data was used to calculate the ADP concentrations for all time courses. The slight variation of the calibration curve, when lower ATP concentrations are used, was neglected. In contrast to ATP, 2 mM glucose did not significantly alter calibration curves.

Test labeling of the two double mutants was done with two different rhodamine isomers, 5-IATR and 6-IATR, and the fluorescence response to ADP binding was investigated. The labeling stoichiometry was 2:1 as confirmed by mass spectrometry. All four combinations showed an increase in fluorescence as expected for the disruption of rhodamine dimers. The larger signal change was observed for ParM (D63C/D224C/C287A) with a 10-fold fluorescence increase when labelled with 6-IATR (Table Y).

TABLE Y

Nucleotide binding affinities and dynamics and fluorescence change of rhodamine-labeled ParM mutants.

| Mutations in addition to D63C D224C C287A | Fluorescence Titration | | | | | Stopped-flow | | |
|---|---|---|---|---|---|---|---|---|
| | ADP | | ATP | | | ADP | | |
| | $F_+/F_-$ | $K_d$ (µM) | $F_+/F_-$ | $K_d$ (µM) | $K_d$ ratio ATP/ADP | $k_{on}$ (µM$^{-1}$s$^{-1}$) | $k_{off}$ (s$^{-1}$) | $K_d$ (µM) |
| 5-IATR | | | | | | | | |
| no additional mutation | 4.1 | 76 | 1.7 | 1200 | 16 | n.d. | n.d. | n.d. |
| T174A T175N | 19 | 63 | >6.0 | >5000 | >80 | 0.066 | 4.5 | 68 |
| K33A T174A T175N | 12 | 31 | >5.0 | >5000 | >160 | 0.105 | 3.0 | 29 |
| 6-IATR | | | | | | | | |
| no additional mutation | 10 | 147 | 3.7 | 1100 | 7.5 | n.d. | n.d. | n.d. |
| T174A T175N | 19 | 103 | >7.0 | >5000 | >50 | 0.056 | 6.4 | 114 |
| K33A T174A T175N | 10 | 39 | >4.0 | >5000 | >130 | 0.076 | 3.4 | 44 |

Equilibrium dissociation constants ($K_d$) and fluorescence change ($F_+/F_-$) upon ADP and ATP binding were determined by fluorescence titration as described in FIG. 15. Association ($k_{on}$) and dissociation ($k_{off}$) rate constants for ADP binding were measured in stopped-flow experiments (FIG. 16) and the dissociation constants were calculated from $k_{off}/k_{on}$ to compare with the values from equilibrium titrations. While the dissociation constants were very reproducible between different batches of a labeled ParM mutant (<20% deviation), the fluorescence change varied between different batches of labeled protein. Values given in the table represent the maximum fluorescence change observed. All data were obtained in 30 mM Tris-HCl pH 7.5, 25 mM KCl, 3 mM MgCl$_2$ and 5 µM BSA at 20° C.

In contrast, the fluorescence change obtained with ParM (D63C/K216C/C287A) was <3-fold with both rhodamine isomers and this could not be improved by further purification of the labeled proteins. Therefore ParM (D63C/D224C/C287A) was chosen for further work.

The fluorescence increase upon ADP binding and the absorbance spectra of rhodamine-labeled ParM indicate dimer formation of the rhodamines on nucleotide-free ParM, which is disturbed by ADP binding (FIG. 14). The absorbance spectrum of 6-ATR-ParM in the absence of ADP is indicative of rhodamine dimers with maximum absorbance at 519 nm and a shoulder around 550 nm (FIG. 14A). Binding of ADP causes an absorbance decrease at 519 nm and a concomitant increase in absorbance at 553 nm. The absorbance spectra show an isosbestic point at 536 nm. 5-IATR-labeled ParM mutants show different absorbance spectra with a higher absorbance at 553 nm and lower absorbance at 519 nm than 6-IATR-labeled ParM (FIG. 14B). Upon ADP additions the absorbance at 553 nm is further increased and decreased at 519 nm. The isosbestic point lies at 532 nm. The difference in absorbance spectra of ParM, labeled either with 5- or 6-IATR, suggests that the exact structural arrangement and interaction of the two rhodamine isomers is slightly different. In contrast to the absorbance spectra, fluorescence spectra of the two isomers on ParM are almost identical with maximal excitation and emission wavelengths of 553 nm and 578 nm (FIG. 14C).

ADP and ATP Affinities

Fluorescence titrations of 5-ATR and 6-ATR ParM (D63C/D224C/C287A) showed that the ADP affinities are 76 μM and 147 μM, respectively (FIG. 15, Table 1). These affinities are orders of magnitude lower than with wild-type ParM (2.4 μM (19)) or the MDCC-ParM (0.46 μM (7)). On one hand this reduces sensitivity of ADP detection, but it also enables use of the sensor at lower concentrations to detect an excess of ADP and therefore to save material. Binding of ATP was weaker than ADP binding in both cases, $K_d$~1 mM, and the fluorescence change upon triphosphate binding was lower (FIG. 15, Table 1).

In order to further improve ADP selectivity two active site mutations, T174A and T175N, were introduced into the ParM variant for rhodamine labeling. The same mutations had been successful in increasing discrimination against ATP in the MDCC-ParM biosensor (7). The new ParM mutant ($His_6$/D63C/T174A/T175N/D224C/C287A), either labeled with 5-IATR and 6-IATR, had slightly increased ADP affinity but the mutations weakened ATP binding to >5 mM, thus improving ADP selectivity (Table 1). After optimizing labeling conditions and purification of the labeled proteins by anion-exchange chromatography, a signal change of ~20-fold was achieved.

An additional mutation, K33A, was introduced into ParM ($His_6$/D63C/T174A/T175N/D224C/C287A), which abolished filament formation in the MDCC-ParM biosensor (7). Beside the effect on filament formation (see below) the resulting ParM variants, 5-ATR and 6-ATR-ParM ($His_6$/K33A/D63C/T174A/T175N/D224C/C287A), showed a further increase in ADP affinity (FIG. 15, Table 1). However, the maximal signal change of 12-fold was not as high as for the rhodamine-labeled ParM variants without. K33A mutation.

ADP Binding Dynamics

Kinetics of ADP binding to different doubly rhodamine-labeled ParM variants were investigated in stopped-flow experiments taking advantage of the rhodamine signal change. Association kinetics were measured under pseudo-first order conditions with an excess of ADP. The fluorescence curves were well fit by single exponentials and the resulting rate constants, $k_{obs}$ were linearly dependent on ADP concentration (FIG. 16), indicating that the speed of the signal change is controlled by the bimolecular binding step in the concentration range examined. Association and dissociation rate constants, calculated from the slope and intercept of linear regression, are summarized in Table 1. The rate constants are similar for the different rhodamine-labeled ParM variants. The dissociation constant obtained from the rate constants is in very good agreement with the values determined in equilibrium titrations. Comparison with the ADP binding kinetics of MDCC-ParM (7) shows that the strongly reduced ADP affinity in rhodamine-labeled ParM (about two orders of magnitude) is due to a combination of an order of magnitude reduction in the association rate constant and a similar size increase in the dissociation rate constant. The maximum response time of the rhodamine biosensors is defined by the dissociation rate constants, $1/k_{off}$, which is <0.33 for the slowest variant. Thus, the rhodamine-based ParM biosensors are well suited for real-time kinetic measurements of ATPase and kinase activity.

Filament Formation

The rhodamine-ParM variants would most likely be used at concentrations<1 μM (see below), which is below the critical, concentration of filament formation of wild-type ParM (19). Hence, filament formation might be less problematic here than with the MDCC-ParM variant, which is likely to be used in at least tenfold higher concentration. Nevertheless, the K33A mutation, known to inhibit filament formation (16), was introduced into the ParM variant for rhodamine-labeling. Polymerization of the rhodamine-labeled ParM variants with and without K33A mutation was investigated by right-angle light scattering (FIG. 17). 5-IATR-labeled ParM ($His_6$/D63C/T174A/T175N/D224C/C287A) formed filaments in presence of high concentrations of ATP (4 mM), albeit much slower than the wild-type protein (FIG. 17A), (19, 20). The critical concentration for the labeled ParM in presence of ATP was determined to be 0.8 μM, even lower than for wild-type ParM, 2.5 μM, under the same conditions (FIG. 17B). However, the error on the critical concentration is relatively high. In contrast to wild-type ParM, where filaments rapidly depolymerize due to ATP hydrolysis, 5-AIR ParM filaments were stable over a period of at least four hours (FIG. 17A). This could mean that ATP hydrolysis and/or $P_i$-release is very slow or that it does not lead to depolymerization. The latter seems more likely since 5-ATR-ParM also polymerized in presence of ADP (FIG. 17A).

The 6-IATR labeled ParM ($His_6$/D63C/T174A/T175N/D224C/C287A) showed similar polymerization kinetics to the 5-IATR labeled variant, but the critical concentration was significantly higher, 14 μM (FIG. 17B) and no filament formation was observed in the presence of ADP. Whereas 5-ATR-ParM and wild-type ParM showed very similar scattering intensities, the light scattering signal was much weaker for 6-IATR labeled ParM (FIG. 17B). This is possibly an indication for 6-ATR-ParM filaments having a different structure (see discussion).

ParM ($His_6$/K33A/D63C/T174A/T175N/D224C/C287A) containing the K33A mutation did not show any change in light scattering under the conditions above, when labeled with 5- or 6-IATR (FIG. 17a). Thus, as in the previously described biosensor, the K33A mutation effectively blocks filament formation.

Application Example

Steady-State Kinetics of Hexokinase

As an example of kinetic measurements using the rhodamine-ParM biosensors, the phosphorylation reaction of D-glucose catalyzed by hexokinase from S. cerevisiae was examined (FIG. 18). Steady-state kinetics of the phosphorylation reaction was measured by monitoring ADP generation with the rhodamine-ParM biosensor 5-ATR-ParM ($His_6$/D63C/T174A/T175N/D224C/C287A). The sensor was used at lower concentration than ADP, so that the fractional saturation of rhodamine-ParM changes with ADP concentration in a broad range about the dissociation constant. Although this yields a non-linear relationship between fluorescence signal and ADP, at low ADP concentration (<30 μM) the sensor response is approximately linear (FIG. 18A). While glucose, at the maximum concentration used in the assay (2 mM), did not significantly alter the sensor response, the presence of 1 mM ATP (max. concentration used) increased the background level and so decreased the slope of the calibration curve, albeit by only 12% (FIG. 18A). The slope of the calibration curve in presence of 1 mM ATP was used to calculate the ADP concentrations in all experiments. Time courses of ADP generation were monitored either at constant glucose concentration and varying ATP (FIG. 18B) or at constant ATP and increasing glucose concentration. From Michaelis-Menten plots (FIGS. 18C and 18D) the parameters $K_M^{ATP}$, 80 μM and $V_{max}$, 20 μM min$^{-1}$, were obtained from variation of ATP and $K_M^{glucose}$, 170 μM, and $V_{max}$, 23 μM min$^{-1}$ for variation of the D-glucose concentration. The $V_{max}$-values yield an activity of 1.08 μmol min$^{-1}$ per unit of hexokinase, which is in very good agreement with the unit definition of the supplier, 1 μM min$^{-1}$ unit$^{-1}$, under similar experimental conditions (pH 7.6, 25° C.).

DISCUSSION

The dissociation constants of ADP binding to all rhodamine-labeled variants are in the range of 30-100 μM, which are much higher than that of MDCC-ParM (0.5 μM) (7). This reduced affinity could be due to the larger size of the rhodamines, along with the two cysteine mutations affecting the binding. Alternatively the binding of ADP requires the cleft closure and hence the disruption of the rhodamine stacking interaction. A second rhodamine labeled double mutant (D63C/K216C) has more than tenfold higher ADP affinity than the (D63C/D224C) mutants suggesting that weakened ADP binding is at least in part due to the mutation D224C. In a previous use of rhodamine stacking sensing a protein conformation change with the phosphate binding protein, the rhodamine had little effect on the affinity for inorganic phosphate (15), suggesting that the rhodamine stacking per se may not necessarily have a significant effect on the energetics. However, in the case of two rhodamines attached to the same polypeptide of a folded protein, the ability of rhodamines to stack and the stacking arrangement itself may be much more restricted than in the situation, where rhodamines are relatively free to find the optimal configuration, either in free solution or attached to a flexible peptide (14). Thus the energetics of the stacking may vary between proteins. Indeed, the spectral data with the phosphate binding protein (15), suggests such differences do occur. The low affinity makes the rhodamine versions less sensitive in comparison to the MDCC sensor, but more suitable for high ATP concentrations.

For labeling of ParM the pure rhodamine isomers 5-IATR and 6-IATR were used. Although a very similar fluorescence change was observed with each isomer, the absolute fluorescence signal was lower for the 6-IATR and the absorbance spectra showed large differences in the intensity ratio of the bands at 519/550 nm. This indicates that the two rhodamine isomers have a different structural arrangement when attached to the cysteines on ParM. The 6-ATR molecules seem to form a stronger stacking interaction on ParM, as the absorbance ratio at 519 nm/550 nm is higher and the fluorescence intensity is lower. Since an isomer mixture of 5- and 6-IATR is easier to synthesize, it may be desirable to use this, (and simply test whether a similar signal change can also be obtained using the mixture for labeling ParM before deploying the sensor).

In addition to the fluorescence and absorbance differences, also the different behaviour in filament formation of ParM (His$_6$/D63C/T174A/T175N/D224C/C287A), labeled with either 5-IATR or 6-IATR, suggests that the rhodamine isomers adopt a different conformation. In contrast to 5-ATR-ParM, the 6-ATR-ParM does not form filaments with ADP, has a higher critical concentration in presence for ATP and the scattering intensity, very similar between 5-ATR-ParM and wild-type, is strongly reduced. An explanation for the lower light scattering could be a different structure of the filaments (length, thickness, less bundle formation), which causes less light scattering. In this context it is interesting that Popp et al. (21) found that the interaction of D63 with R262 is important in interstrand contacts of the ParM filament and ParM carrying the R262D mutation forms only single-stranded protofilaments. The rhodamines on ParM might therefore interfere with the interstrand contacts and inhibit formation of double-stranded filaments. However, it is difficult to explain why the 6-isomer, but not the 5-isomer, would block such interstrand interaction.

From the four preferred different doubly rhodamine labeled ParM variants that have been characterized, we consider 5-ATR-ParM (His$_6$/D63C/T174A/T175N/D224C/C287A) as the generally most suitable ADP sensor for the following reasons. Although this ParM variant still forms filaments at higher concentrations, assays are likely to be carried out at concentrations, well below the critical concentration, and in practice polymerization does not seem to cause problems, as shown in the hexokinase assay (FIG. 18). The K33A mutation effectively blocked filament formation but also decreased the signal change upon ADP binding. Only maximal 12-fold fluorescence increase was obtained compared to a 20-fold increase for the ParM variants without K33A. However, the signal change may be improved by optimization. In comparison to the 6-IATR-labeled ParM (His$_6$/D63C/T174A/T175N/D224C/C287A) the version with 5-IATR has higher ADP affinity (63 μM versus 103 μM) and so has a lower detection limit.

The rhodamine-labeled biosensor may be used in a different manner than MDCC-ParM, that is at lower concentration than the ADP to be detected. Because of the weak binding, the degree of saturation and thus the fluorescence will vary with ADP in a wide range around the dissociation constant. While this method of measurement is inherently less sensitive than quantitative capture of ADP by a high affinity sensor, it has the large advantage of requiring only low concentration of the sensor in the assay solution. High concentrations of proteins are not only more likely to interfere with the assay, for example interacting with some component or introducing inner filter effects, but is also more expensive in terms of material used. In practice, the concentration of sensor protein would be determined mainly by the sensitivity of the optical detection system and the accuracy required by the skilled user. As we show in the hexokinase assay submicromolar concentrations of the sensor can, be easily used. In addition, the rhodamine-labeled sensor extends the potential use to higher ATP concentrations and means that ADP contamination in ATP is less problematic than with MDCC-ParM. Finally, rhodamine is generally more photostable than coumarin and the fluorescence is excited and detected at higher wavelengths. These properties are likely to make rhodamine-ParM more suitable for applications like high throughput assays.

REFERENCES TO EXAMPLE 9

1. Itaya, K., and Ui, M. (1966) A new micromethod for the colorimetric determination of inorganic phosphate, *Clinica Chimica Acta* 14, 361-366.
2. Charter, N. W., Kauffman, L., Singh, R., and Eglen, R. M. (2006) A generic, homogenous method for measuring kinase and inhibitor activity via adenosine 5'-diphosphate accumulation, *J. Biomol. Screen.* 11, 390-399.
3. Srinivasan, J., Cload, S. T., Hamaguchi, N., Kurz, J., Keene, S., Kurz, M., Boomer, R. M., Blanchard, J., Epstein, D., Wilson, C., and Diener, J. L. (2004) ADP-specific sensors enable universal assay of protein kinase activity, *Chemistry & Biology* 11, 499-508.
4. Kleman-Leyer, K. M., Klink, T. A., Kopp, A. L., Westermeyer, T. A., Koeff, M. D., Larson, B. R., Worzella, T. J., Pinchard, C. A., van de Kar, S. A., Zaman, G. J., Hornberg, J. J., and Lowery, R. G. (2009) Characterization and optimization of a red-shifted fluorescence polarization ADP detection assay, *Assay and drug development technologies*.
5. Hong, L., Quinn, C. M., and Jia, Y. (2009) Evaluating the utility of the HTRF®Transcreener™ ADP assay technology: A comparison with the standard HTRF®assay technology, *Anal. Biochem.* 391, 31-38.
6. Lowery, R. G., and Kleman-Leyer, K. (2006) Transcreener: screening enzymes involved in covalent regulation, *Expert opinion on therapeutic targets* 10, 179-90.
7. Kunzelmann, S., and Webb, M. R. (2009) A biosensor for fluorescent determination of ADP with high time resolution, submitted.
8. van den Ent, F., Moller-Jensen, J., Amos, L. A., Gerdes, K., and Lowe, J. (2002) F-actin-like filaments formed by plasmid segregation protein ParM, *EMBO J.* 21, 6935-43.
9. Kasha, M. (1963) Energy transfer mechanisms and the molecular exciton model for molecular aggregates, *Radiat. Res.* 20, 55-70.
10. Kasha, M., Rawls, H. R., and Ashraf El-Bayoumi, M. (1965) The exciton model in molecular spectroscopy, *Pure Appl. Chem.* 11, 371-392.
11. Scholes, G. D., and Ghiggino, K. P. (1994) Electronic interactions and interchromophore electron transfer, *J. Phys. Chem.* 98, 4580-4590.
12. Packard, B. Z., Toptygin, D. D., Komoriya, A., and Brand, L. (1996) Profluorescent protease substrates: intramolecular dimers described by the exciton model, *Proc. Natl. Acad. Sci. U.S.A.* 93, 11640-11645.
13. Packard, B. Z., Toptygin, D. D., Komoriya, A., and Brand, L. (1997) Design of profluorescent protease substrates guided by exciton theory, *Methods Enzymol* 278, 15-23.
14. Blackman, M. J., Corrie, J. E. T., Croney, J. C., Kelly, G., Eccleston, J. F., and Jameson, D. M. (2002) Structural and biochemical characterization of a fluorogenic rhodamine-labeled malarial protease substrate, *Biochemistry* 41, 12244-12252.
15. Okoh, M. P., Hunter, J. L., Corrie, J. E. T., and Webb, M. R. (2006) A biosensor for inorganic phosphate using a rhodamine-labeled phosphate binding protein, *Biochemistry* 45, 14764-14771.
16. Salje, J., and Lowe, J. (2008) Bacterial actin: architecture of the ParMRC plasmid DNA partitioning complex, *EMBO J.* 27, 2230-2238.
17. Pace, C. N., Vajdos, F., Fee, L., Grimsley, G., and Gray, T. (1995) How to measure and predict the molar absorption coefficient of a protein, *Protein Sci* 4, 2411-2423.
18. Corrie, J. E. T., and Craik, J. S. (1994) Synthesis and characterisation of pure isomers of iodoacetamidotetramethylrhodamine, *J. Chem. Soc. Perkin Trans. I*, 2967-2974.
19. Garner, E. C., Campbell, C. S., and Mullins, R. D. (2004) Dynamic instability in a DNA-segregating prokaryotic actin homolog, *Science* 306, 1021-5.
20. Popp, D., Yamamoto, A., Iwasa, M., Narita, A., Maeda, K., and Maeda, Y. (2007) Concerning the dynamic instability of actin homolog ParM, *Biochem. Biophys. Res. Commun.* 353, 109-14.
21. Popp, D., Iwasa, M., Maeda, K., Narita, A., Oda, T., and Maeda, Y. (2009) Protofilament Formation of ParM Mutants, *J. Mol. Biol.* 388, 209-217.

REFERENCES

1. Charter, N. W., Kauffman, L., Singh, R., and Eglen, R. M. (2006) A Generic, Homogenous Method for Measuring Kinase and Inhibitor Activity via Adenosine 5'-Diphosphate Accumulation, *J. Biomol. Screen.* 11, 390-399.
2. Srinivasan, J., Cload, S. T., Hamaguchi, N., Kurz, J., Keene, S., Kurz, M., Boomer, R. M., Blanchard, J., Epstein, D., Wilson, C., and Diener, J. L. (2004) ADP-Specific Sensors Enable Universal Assay of Protein Kinase Activity, *Chemistry & Biology* 11, 499-508.
3. Gilardi, G., Zhou, L. Q., Hibbert, L., and Cass, A. E. G. (1994) Engineering the maltose binding protein for reagentless fluorescence sensing, *Anal. Chem.* 66, 3840-3847.
4. Brune, M., Hunter, J. L., Corrie, J. E. T., and Webb, M. R. (1994) Direct, real-time measurement of rapid inorganic phosphate release using a novel fluorescent probe and its application to actomyosin subfragment 1 ATPase, *Biochemistry* 33, 8262-8271.
5. Salins, L. L., Ware, R. A., Ensor, C. M., and Daunert, S. (2001) A novel reagentless sensing system for measuring glucose based on the galactose/glucose-binding protein, *Anal Biochem* 294, 19-26.
6. Dattelbaum, J. D., and Lakowicz, J. R. (2001) Optical determination of glutamine using a genetically engineered protein, *Anal. Biochem.* 291, 89-95.
7. De Lorimier, R. M., Smith, J. J., Dwyer, M. A., Looger, L. L., Sali, K. M., Paavola, C. D., Rizk, S. S., Sadigov, S., Conrad, D. W., Loew, L., and Helling a, H. W. (2002) Construction of a fluorescent biosensor family, *Protein Sci.* 11, 2655-2675.
8. Brune, M., Corrie, J. E. T., and Webb, M. R. (2001) A fluorescent sensor of the phosphorylation state of nucleoside diphosphate kinase and its use to monitor nucleoside diphosphate concentrations in real time, *Biochemistry* 40, 5087-5094.
9. Ebersbach, G., and Gerdes, K. (2005) Plasmid segregation mechanisms, *Annual review of genetics* 39, 453-79.
10. Dam, M., and Gerdes, K. (1994) Partitioning of plasmid R1. Ten direct repeats flanking the parA promoter constitute a centromere-like partition site parC, that expresses incompatibility, *J Mol Biol* 236, 1289-98.
11. Gerdes, K., and Molin, S. (1986) Partitioning of plasmid R1. Structural and functional analysis of the parA locus, *J Mol Biol* 190, 269-79.
12. Jensen, R. B., Dam, M., and Gerdes, K. (1994) Partitioning of plasmid R1. The parA operon is autoregulated by ParR and its transcription is highly stimulated by a downstream activating element, *J Mol Biol* 236, 1299-309.
13. Jensen, R. B., Lurz, R., and Gerdes, K. (1998) Mechanism of DNA segregation in prokaryotes: replicon pairing by parC of plasmid R1, *Proceedings of the National Academy of Sciences of the United States of America* 95, 8550-5.

14. Orlova, A., Garner, E. C., Galkin, V. E., Heuser, J., Mullins, R. D., and Egelman, E. H. (2007) The structure of bacterial ParM filaments, *Nat Struct Mol Biol* 14, 921-6.
15. van den Ent, F., Moller-Jensen, J., Amos, L. A., Gerdes, K., and Lowe, J. (2002) F-actin-like filaments formed by plasmid segregation protein ParM, *EMBO J.* 21, 6935-43.
16. Moller-Jensen, J., Jensen, R. B., Lowe, J., and Gerdes, K. (2002) Prokaryotic DNA segregation by an actin-like filament, *The EMBO journal* 21, 3119-27.
17. Moller-Jensen, J., Borch, J., Dam, M., Jensen, R. B., Roepstorff, P., and Gerdes, K. (2003) Bacterial mitosis: ParM of plasmid R1 moves plasmid DNA by an actin-like insertional polymerization mechanism, *Mol Cell* 12, 1477-87.
18. Garner, E. C., Campbell, C. S., Weibel, D. B., and Mullins, R. D. (2007) Reconstitution of DNA segregation driven by assembly of a prokaryotic actin homolog, *Science* 315, 1270-4.
19. Garner, E. C., Campbell, C. S., and Mullins, R. D. (2004) Dynamic instability in a DNA-segregating prokaryotic actin homolog, *Science* 306, 1021-5.
20. Moller-Jensen, J., Ringgaard, S., Mercogliano, C. P., Gerdes, K., and Lowe, J. (2007) Structural analysis of the ParR/parC plasmid partition complex, *The EMBO journal* 26, 4413-22.
21. Popp, D., Akihiro Narita, A., Oda, T., Fujisawa, T., Matsuo, H., Nitanai, Y., Iwasa, M., Maeda, K., Onishi, H., and Maeda, Y. (2008) Molecular structure of the ParM polymer and the mechanism leading to its nucleotide-driven dynamic instability, *EMBO J.* 27, 570-579.
22. Popp, D., Yamamoto, A., Iwasa, M., Narita, A., Maeda, K., and Maeda, Y. (2007) Concerning the dynamic instability of actin homolog ParM, *Biochem Biophys Res Commun* 353, 109-14.
23. Campbell, C. S., and Mullins, R. D. (2007) In vivo visualization of type II plasmid segregation: bacterial actin filaments pushing plasmids, *The Journal of cell biology* 179, 1059-66.
24. Kasha, M. (1963) Energy transfer mechanisms and the molecular exciton model for molecular aggregates, *Radiat. Res.* 20, 55-70.
25. Kasha, M., Rawls, H. R., and Ashraf El-Bayoumi, M. (1965) The exciton model in molecular spectroscopy, *Pure Appl. Chem.* 11, 371-392.
26. Scholes, G. D., and Ghiggino, K. P. (1994) Electronic interactions and interchromophore electron transfer, *J. Phys. Chem.* 98, 4580-4590.
27. Packard, B. Z., Toptygin, D. D., Komoriya, A., and Brand, L. (1996) Profluorescent protease substrates: intramolecular dimers described by the exciton model, *Proc. Natl. Acad. Sci. U.S.A.* 93, 11640-11645.
28. Packard, B. Z., Toptygin, D. D., Komoriya, A., and Brand, L. (1997) Design of profluorescent protease substrates guided by exciton theory, *Methods Enzymol* 278, 15-23.
29. Blackman, M. J., Corrie, J. E. T., Croney, J. C., Kelly, G., Eccleston, J. F., and Jameson, D. M. (2002) Structural and biochemical characterization of a fluorogenic rhodamine-labeled malarial protease substrate, *Biochemistry* 41, 12244-12252.
30. Okoh, M. P., Hunter, J. L., Corrie, J. E. T., and Webb, M. R. (2006) A biosensor for inorganic phosphate using a rhodamine-labeled phosphate binding protein, *Biochemistry* 45, 14764-14771.
31. Dillingham, M. S., Wigley, D. B., and Webb, M. R. (2002) Direct measurement of single stranded DNA translocation by PcrA helicase using the fluorescent base analogue 2-aminopurine, *Biochemistry* 41, 643-651.
32. Av-Gay, Y., and Everett, M. (2000) The eukaryotic-like Ser/Thr protein kinases of *Mycobacterium tuberculosis*, *Trends in microbiology* 8, 238-44.
33. Fernandez, P., Saint-Joanis, B., Baritone, N., Jackson, M., Gicquel, B., Cole, S. T., and Alzari, P. M. (2006) The Ser/Thr protein kinase PknB is essential for sustaining mycobacterial growth, *J Bacteriol* 188, 7778-84.
34. Wehenkel, A., Fernandez, P., Bellinzoni, M., Catherinot, V., Barilone, N., Labesse, G., Jackson, M., and Alzari, P. M. (2006) The structure of PknB in complex with mitoxantrone, an ATP-competitive inhibitor, suggests a mode of protein kinase regulation in mycobacteria, *FEBS Lett* 580, 3018-22.
35. Szekely, R., Waczek, F., Szabadkai, I., Nemeth, G., Hegymegi-Barakonyi, B., Eros, D., Szokol, B., Pato, J., Hafenbradl, D., Satchell, J., Saint-Joanis, B., Cole, S. T., Orfi, L., Klebl, B. M., and Keri, G. (2008) A novel drug discovery concept for tuberculosis: inhibition of bacterial and host cell signalling, *Immunology letters* 116, 225-31.
36. Villarino, A., Duran, R., Wehenkel, A., Fernandez, P., England, P., Brodin, P., Cole, S. T., Zimny-Arndt, U., Jungblut, P. R., Cervenansky, C., and Alzari, P. M. (2005) Proteomic identification of *M. tuberculosis* protein kinase substrates: PknB recruits GarA, a FHA domain-containing protein, through activation loop-mediated interactions, *J Mol Biol* 350, 953-63.
37. Van den Ent, F., Amos, L. A., and Lowe, J. (2001) Prokaryotic origin of the actin cytoskeleton, *Nature* 413, 39-44.
38. Esue, O., Wirtz, D., and Tseng, Y. (2006) GTPase activity, structure, and mechanical properties of filaments assembled from bacterial cytoskeleton protein MreB, *J Bacteriol* 188, 968-76.
39. Lara, B., Rico, A. I., Petruzzelli, S., Santona, A., Dumas, J., Biton, J., Vicente, M., Mingorance, J., and Massidda, O. (2005) Cell division in cocci: localization and properties of the *Streptococcus pneumoniae* FtsA protein, *Mol Microbiol* 55, 699-711.
40. Roeben, A., Kofler, C., Nagy, I., Nickell, S., Hartl, F. U., and Bracher, A. (2006) Crystal structure of an archaeal actin homolog, *J Mol Biol* 358, 145-56.
41. Nara, F., Yamashiro, K., Nemoto, N., Ohta, Y., Yokobori, S., Yasunaga, T., Hisanaga, S., and Yamagishi, A. (2007) An actin homolog of the archaeon *Thermoplasma acidophilum* that retains the ancient characteristics of eukaryotic actin, *J Bacteriol* 189, 2039-45.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. An ADP binding molecule comprising a polypeptide, said polypeptide comprising an amino acid sequence corresponding to at least amino acids 11 to 310 of SEQ ID NO:1, wherein said polypeptide comprises:
   (a) a C287A substitution relative to SEQ ID NO: 1;
   (b) a cysteine residue for attachment of at least one reporter moiety wherein said polypeptide comprises a substitution or substitutions selected from the group consisting of: (i) I27C; (ii) D63C and K16C; and (iii) D63C and D224C;
   (c) substituting or substitutions selected from the group consisting of: (iv) T175N; (v) T174A and T175A; (vi) T174A and T175 and (vii) T175L; and
   (d) a residue selected from K or A at position 33.

2. An ADP binding molecule according to claim 1, wherein said polypeptide comprises a further substitution or substitutions selected from the group consisting of:
   (iv) T175N;
   (v) T174A and T175A; and
   (vi) T174A and T175N.

3. An ADP binding molecule according to claim 1, wherein said polypeptide comprises a substitution of K33A.

4. An ADP binding molecule according to claim 1 further comprising at least one fluorophore attached thereto, wherein said fluorophore is attached at a position on the polypeptide such that conformational change of the polypeptide upon ADP binding causes a corresponding change in fluorescence of said fluorophore.

5. An ADP binding molecule according to claim 4 wherein each fluorophore is attached to the polypeptide via an amino acid residue corresponding to one or more of I27C, D63C, K216C or D224C.

6. An ADP binding molecule according to claim 1, said molecule further comprising at least one N-[2-(1-maleimidyl)ethyl]-7-diethylaminocoumarin-3-carboxamide (MDCC) moiety attached thereto.

7. An ADP binding molecule according to claim 1, said molecule further comprising at least two 5-iodoacetamidotetramethylrhodamine (5-IATR) moieties attached thereto.

8. An ADP binding molecule according to claim 1, said molecule comprising the amino acid sequence of SEQ ID NO:5.

9. An ADP binding molecule according to claim 1, said molecule comprising the amino acid sequence of SEQ ID NO:6 or SEQ ID NO:7.

10. A nucleic acid having a nucleotide sequence encoding the polypeptide portion of an ADP binding molecule according to claim 1.

11. A method for monitoring changes in ADP concentration in a sample comprising contacting said sample with an ADP binding molecule according to claim 1 and determining changes in conformation of said ADP binding molecule, wherein changes in conformation of said ADP binding molecule indicate changes in the concentration of ADP in said sample.

12. A method according to claim 11 wherein the conformation of said APP binding molecule is monitored by measurement of changes in fluorescence of a fluorophore comprised by said ADP binding molecule.

13. A method according to claim 11 wherein the sample comprises an ATPase.

14. A method according to claim 13 wherein the sample comprises a helicase.

15. A method according to claim 13 wherein the sample comprises a kinase.

* * * * *

SEQUENCE LISTING

<160> NUMBER OF SEQ ID NOS: 7

<210> SEQ ID NO 1
<211> LENGTH: 320
<212> TYPE: PRT
<213> ORGANISM: Escherichia coli

<400> SEQUENCE: 1

Met Leu Val Phe Ile Asp Asp Gly Ser Thr Asn Ile Lys Leu Gln Trp
1               5                   10                  15

Gln Glu Ser Asp Gly Thr Ile Lys Gln His Ile Ser Pro Asn Ser Phe
            20                  25                  30

Lys Arg Glu Trp Ala Val Ser Phe Gly Asp Lys Lys Val Phe Asn Tyr
        35                  40                  45

Thr Leu Asn Gly Glu Gln Tyr Ser Phe Asp Pro Ile Ser Pro Asp Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

Gln Pro Asn Thr Glu Asn Ile Glu Arg Lys Lys Ala Asn Phe Arg Lys
        115                 120                 125

Lys Ile Thr Leu Asn Gly Gly Asp Thr Phe Thr Ile Lys Asp Val Lys
    130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Thr Thr Leu
                165                 170                 175

Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Asp
    210                 215                 220

Ile Ile Ile His Arg Lys Asp Asn Asn Tyr Leu Lys Gln Arg Ile Asn
225                 230                 235                 240

Asp Glu Asn Lys Ile Ser Ile Val Thr Glu Ala Met Asn Glu Ala Leu
                245                 250                 255

Arg Lys Leu Glu Gln Arg Val Leu Asn Thr Leu Asn Glu Phe Ser Gly
            260                 265                 270

Tyr Thr His Val Met Val Ile Gly Gly Gly Ala Glu Leu Ile Cys Asp
        275                 280                 285

Ala Val Lys Lys His Thr Gln Ile Arg Asp Glu Arg Phe Phe Lys Thr
    290                 295                 300

Asn Asn Ser Gln Tyr Asp Leu Val Asn Gly Met Tyr Leu Ile Gly Asn
305                 310                 315                 320

<210> SEQ ID NO 2
<211> LENGTH: 330
<212> TYPE: PRT
<213> ORGANISM: Escherichia coli

<400> SEQUENCE: 2

```
Met Leu Val Phe Ile Asp Asp Gly Ser Thr Asn Ile Lys Leu Gln Trp
1               5                   10                  15

Gln Glu Ser Asp Gly Thr Ile Lys Gln His Cys Ser Pro Asn Ser Phe
            20                  25                  30

Lys Arg Glu Trp Ala Val Ser Phe Gly Asp Lys Val Phe Asn Tyr
        35                  40                  45

Thr Leu Asn Gly Glu Gln Tyr Ser Phe Asp Pro Ile Ser Pro Asp Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
                100                 105                 110

Gln Pro Asn Thr Glu Asn Ile Glu Arg Lys Lys Ala Asn Phe Arg Lys
            115                 120                 125

Lys Ile Thr Leu Asn Gly Gly Asp Thr Phe Thr Ile Lys Asp Val Lys
        130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Ala Asn Leu
                165                 170                 175

Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Asp
210                 215                 220

Ile Ile Ile His Arg Lys Asp Asn Tyr Leu Lys Gln Arg Ile Asn
225                 230                 235                 240

Asp Glu Asn Lys Ile Ser Ile Val Thr Glu Ala Met Asn Glu Ala Leu
            245                 250                 255

Arg Lys Leu Glu Gln Arg Val Leu Asn Thr Leu Asn Glu Phe Ser Gly
        260                 265                 270

Tyr Thr His Val Met Val Ile Gly Gly Gly Ala Glu Leu Ile Ala Asp
    275                 280                 285

Ala Val Lys Lys His Thr Gln Ile Arg Asp Glu Arg Phe Phe Lys Thr
290                 295                 300

Asn Asn Ser Gln Tyr Asp Leu Val Asn Gly Met Tyr Leu Ile Gly Asn
305                 310                 315                 320

Gln Ser Gly Ser His His His His His
                325                 330

<210> SEQ ID NO 3
<211> LENGTH: 320
<212> TYPE: PRT
<213> ORGANISM: Escherichia coli

<400> SEQUENCE: 3

Met Leu Val Phe Ile Asp Asp Gly Ser Thr Asn Ile Lys Leu Gln Trp
1               5                   10                  15

Gln Glu Ser Asp Gly Thr Ile Lys Gln His Ile Ser Pro Asn Ser Phe
            20                  25                  30

Lys Arg Glu Trp Ala Val Ser Phe Gly Asp Lys Val Phe Asn Tyr
        35                  40                  45
```

Thr Leu Asn Gly Glu Gln Tyr Ser Phe Asp Pro Ile Ser Pro Cys Ala
            50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

Gln Pro Asn Thr Glu Asn Ile Glu Arg Lys Ala Asn Phe Arg Lys
            115                 120                 125

Lys Ile Thr Leu Asn Gly Gly Asp Thr Phe Thr Ile Lys Asp Val Lys
130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Thr Thr Leu
                165                 170                 175

Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Cys
210                 215                 220

Ile Ile Ile His Arg Lys Asp Asn Asn Tyr Leu Lys Gln Arg Ile Asn
225                 230                 235                 240

Asp Glu Asn Lys Ile Ser Ile Val Thr Glu Ala Met Asn Glu Ala Leu
                245                 250                 255

Arg Lys Leu Glu Gln Arg Val Leu Asn Thr Leu Asn Glu Phe Ser Gly
            260                 265                 270

Tyr Thr His Val Met Val Ile Gly Gly Gly Ala Glu Leu Ile Ala Asp
        275                 280                 285

Ala Val Lys Lys His Thr Gln Ile Arg Asp Glu Arg Phe Phe Lys Thr
290                 295                 300

Asn Asn Ser Gln Tyr Asp Leu Val Asn Gly Met Tyr Leu Ile Gly Asn
305                 310                 315                 320

<210> SEQ ID NO 4
<211> LENGTH: 320
<212> TYPE: PRT
<213> ORGANISM: Escherichia coli

<400> SEQUENCE: 4

Met Leu Val Phe Ile Asp Asp Gly Ser Thr Asn Ile Lys Leu Gln Trp
1               5                   10                  15

Gln Glu Ser Asp Gly Thr Ile Lys Gln His Ile Ser Pro Asn Ser Phe
            20                  25                  30

Lys Arg Glu Trp Ala Val Ser Phe Gly Asp Lys Lys Val Phe Asn Tyr
        35                  40                  45

Thr Leu Asn Gly Glu Gln Tyr Ser Phe Asp Pro Ile Ser Pro Cys Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

```
Gln Pro Asn Thr Glu Asn Ile Glu Arg Lys Lys Ala Asn Phe Arg Lys
            115                 120                 125

Lys Ile Thr Leu Asn Gly Gly Asp Thr Phe Thr Ile Lys Asp Val Lys
        130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Thr Thr Leu
                165                 170                 175

Asp Ile Ser Gln Val Met Gly Lys Leu Ser Gly Ile Ser Lys Ile Tyr
                180                 185                 190

Gly Asp Ser Ser Leu Gly Val Ser Leu Val Thr Ser Ala Val Lys Asp
            195                 200                 205

Ala Leu Ser Leu Ala Arg Thr Cys Gly Ser Ser Tyr Leu Ala Asp Asp
        210                 215                 220

Ile Ile Ile His Arg Lys Asp Asn Asn Tyr Leu Lys Gln Arg Ile Asn
225                 230                 235                 240

Asp Glu Asn Lys Ile Ser Ile Val Thr Glu Ala Met Asn Glu Ala Leu
                245                 250                 255

Arg Lys Leu Glu Gln Arg Val Leu Asn Thr Leu Asn Glu Phe Ser Gly
            260                 265                 270

Tyr Thr His Val Met Val Ile Gly Gly Gly Ala Glu Leu Ile Ala Asp
        275                 280                 285

Ala Val Lys Lys His Thr Gln Ile Arg Asp Glu Arg Phe Phe Lys Thr
290                 295                 300

Asn Asn Ser Gln Tyr Asp Leu Val Asn Gly Met Tyr Leu Ile Gly Asn
305                 310                 315                 320

<210> SEQ ID NO 5
<211> LENGTH: 330
<212> TYPE: PRT
<213> ORGANISM: Escherichia coli

<400> SEQUENCE: 5

Met Leu Val Phe Ile Asp Asp Gly Ser Thr Asn Ile Lys Leu Gln Trp
1               5                   10                  15

Gln Glu Ser Asp Gly Thr Ile Lys Gln His Cys Ser Pro Asn Ser Phe
            20                  25                  30

Ala Arg Glu Trp Ala Val Ser Phe Gly Asp Lys Lys Val Phe Asn Tyr
        35                  40                  45

Thr Leu Asn Gly Glu Gln Tyr Ser Phe Asp Pro Ile Ser Pro Asp Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

Gln Pro Asn Thr Glu Asn Ile Glu Arg Lys Lys Ala Asn Phe Arg Lys
        115                 120                 125

Lys Ile Thr Leu Asn Gly Gly Asp Thr Phe Thr Ile Lys Asp Val Lys
    130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Ala Asn Leu
                165                 170                 175
```

```
Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Asp
    210                 215                 220

Ile Ile Ile His Arg Lys Asp Asn Tyr Leu Lys Gln Arg Ile Asn
225                 230                 235                 240

Asp Glu Asn Lys Ile Ser Ile Val Thr Glu Ala Met Asn Glu Ala Leu
                245                 250                 255

Arg Lys Leu Glu Gln Arg Val Leu Asn Thr Leu Asn Glu Phe Ser Gly
            260                 265                 270

Tyr Thr His Val Met Val Ile Gly Gly Gly Ala Glu Leu Ile Ala Asp
        275                 280                 285

Ala Val Lys Lys His Thr Gln Ile Arg Asp Glu Arg Phe Phe Lys Thr
    290                 295                 300

Asn Asn Ser Gln Tyr Asp Leu Val Asn Gly Met Tyr Leu Ile Gly Asn
305                 310                 315                 320

Gln Ser Gly Ser His His His His His
                325                 330

<210> SEQ ID NO 6
<211> LENGTH: 330
<212> TYPE: PRT
<213> ORGANISM: Escherichia coli

<400> SEQUENCE: 6

Met Leu Val Phe Ile Asp Asp Gly Ser Thr Asn Ile Lys Leu Gln Trp
1               5                   10                  15

Gln Glu Ser Asp Gly Thr Ile Lys Gln His Ile Ser Pro Asn Ser Phe
            20                  25                  30

Lys Arg Glu Trp Ala Val Ser Phe Gly Asp Lys Lys Val Phe Asn Tyr
        35                  40                  45

Thr Leu Asn Gly Glu Gln Tyr Ser Phe Asp Pro Ile Ser Pro Cys Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

Gln Pro Asn Thr Glu Asn Ile Glu Arg Lys Lys Ala Asn Phe Arg Lys
        115                 120                 125

Lys Ile Thr Leu Asn Gly Gly Asp Thr Phe Thr Ile Lys Asp Val Lys
    130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Ala Asn Leu
                165                 170                 175

Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Cys
    210                 215                 220
```

Ile Ile Ile His Arg Lys Asp Asn Asn Tyr Leu Lys Gln Arg Ile Asn
225                 230                 235                 240

Asp Glu Asn Lys Ile Ser Ile Val Thr Glu Ala Met Asn Glu Ala Leu
            245                 250                 255

Arg Lys Leu Glu Gln Arg Val Leu Asn Thr Leu Asn Glu Phe Ser Gly
        260                 265                 270

Tyr Thr His Val Met Val Ile Gly Gly Ala Glu Leu Ile Ala Asp
        275                 280                 285

Ala Val Lys Lys His Thr Gln Ile Arg Asp Glu Arg Phe Phe Lys Thr
290                 295                 300

Asn Asn Ser Gln Tyr Asp Leu Val Asn Gly Met Tyr Leu Ile Gly Asn
305                 310                 315                 320

Gln Ser Gly Ser His His His His His His
            325                 330

<210> SEQ ID NO 7
<211> LENGTH: 330
<212> TYPE: PRT
<213> ORGANISM: Escherichia coli

<400> SEQUENCE: 7

Met Leu Val Phe Ile Asp Asp Gly Ser Thr Asn Ile Lys Leu Gln Trp
1               5                   10                  15

Gln Glu Ser Asp Gly Thr Ile Lys Gln His Ile Ser Pro Asn Ser Phe
            20                  25                  30

Ala Arg Glu Trp Ala Val Ser Phe Gly Asp Lys Lys Val Phe Asn Tyr
        35                  40                  45

Thr Leu Asn Gly Glu Gln Tyr Ser Phe Asp Pro Ile Ser Pro Cys Ala
    50                  55                  60

Val Val Thr Thr Asn Ile Ala Trp Gln Tyr Ser Asp Val Asn Val Val
65                  70                  75                  80

Ala Val His His Ala Leu Leu Thr Ser Gly Leu Pro Val Ser Glu Val
                85                  90                  95

Asp Ile Val Cys Thr Leu Pro Leu Thr Glu Tyr Tyr Asp Arg Asn Asn
            100                 105                 110

Gln Pro Asn Thr Glu Asn Ile Glu Arg Lys Lys Ala Asn Phe Arg Lys
        115                 120                 125

Lys Ile Thr Leu Asn Gly Gly Asp Thr Phe Thr Ile Lys Asp Val Lys
    130                 135                 140

Val Met Pro Glu Ser Ile Pro Ala Gly Tyr Glu Val Leu Gln Glu Leu
145                 150                 155                 160

Asp Glu Leu Asp Ser Leu Leu Ile Ile Asp Leu Gly Gly Ala Asn Leu
                165                 170                 175

Asp Ile Ser Gln Val Met Gly Lys Leu Ser Gly Ile Ser Lys Ile Tyr
            180                 185                 190

Gly Asp Ser Ser Leu Gly Val Ser Leu Val Thr Ser Ala Val Lys Asp
        195                 200                 205

Ala Leu Ser Leu Ala Arg Thr Lys Gly Ser Ser Tyr Leu Ala Asp Cys
    210                 215                 220

Ile Ile Ile His Arg Lys Asp Asn Asn Tyr Leu Lys Gln Arg Ile Asn
225                 230                 235                 240

Asp Glu Asn Lys Ile Ser Ile Val Thr Glu Ala Met Asn Glu Ala Leu
                245                 250                 255

Arg Lys Leu Glu Gln Arg Val Leu Asn Thr Leu Asn Glu Phe Ser Gly
            260                 265                 270

```
Tyr Thr His Val Met Val Ile Gly Gly Gly Ala Glu Leu Ile Ala Asp
        275             280                 285

Ala Val Lys Lys His Thr Gln Ile Arg Asp Glu Arg Phe Phe Lys Thr
        290             295                 300

Asn Asn Ser Gln Tyr Asp Leu Val Asn Gly Met Tyr Leu Ile Gly Asn
305                 310                 315                 320

Gln Ser Gly Ser His His His His His His
                325             330
```